(12) United States Patent
Jayakody et al.

(10) Patent No.: US 10,829,731 B2
(45) Date of Patent: Nov. 10, 2020

(54) BIOCATALYSTS FOR CONVERSION OF THERMOCHEMICAL WASTE STREAMS

(71) Applicant: Alliance for Sustainable Energy, LLC, Golden, CO (US)

(72) Inventors: Thelhawadigedara Lahiru Niroshan Jayakody, Wheat Ridge, CO (US); Gregg Tyler Beckham, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/258,255

(22) Filed: Jan. 25, 2019

(65) Prior Publication Data
US 2019/0225933 A1 Jul. 25, 2019

Related U.S. Application Data

(60) Provisional application No. 62/621,891, filed on Jan. 25, 2018.

(51) Int. Cl.
*C12N 9/10* (2006.01)
*C12N 9/88* (2006.01)
*C12N 15/00* (2006.01)
*C12N 1/20* (2006.01)
*C07K 14/195* (2006.01)
*C07K 14/21* (2006.01)
*C02F 3/34* (2006.01)

(52) U.S. Cl.
CPC .............. *C12N 1/20* (2013.01); *C02F 3/34* (2013.01); *C07K 14/195* (2013.01); *C07K 14/21* (2013.01)

(58) Field of Classification Search
CPC . C12N 15/70; C12N 9/88; C12N 1/20; C12N 15/78; C12N 2330/50; C12P 7/10; C12P 7/00; C12P 7/02; C12P 7/22
USPC ........ 435/7.1, 69.7, 105, 165, 252.34, 320.1
See application file for complete search history.

(56) References Cited

U.S. PATENT DOCUMENTS

| 4,952,501 A | 8/1990 | Jasin et al. |
| 6,960,465 B1 | 11/2005 | Papoutsakis et al. |
| 2012/0064560 A1 | 3/2012 | Smith et al. |
| 2015/0376654 A1 | 12/2015 | Koepke et al. |

FOREIGN PATENT DOCUMENTS

WO 2003/057897 A2 7/2003

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Jayakody et al., "Thermochemical wastewater valorization via enhanced microbial toxicity tolerance", Energy & Environmental Science, 2018, vol. 11, pp. 1625-1638.
Johnson et al., "Aromatic catabolic pathway selection for optimal production of pyruvate and lactate from lignin", Metabolic Engineering, 2015, vol. 28, pp. 240-247.
Luan et al., "Engineering cellular robustness of microbes by introducing the GroESL chaperonins from extremophilic bacteria", Journal of Biotechnology, May 2014, vol. 178, pp. 38-40.
Zingaro et al., "Toward a Semisynthetic Stress Response System to Engineer Microbial Solvent Tolerance", mBio, Sep./Oct. 2012, vol. 3, No. 5, pp. 1-5.

* cited by examiner

*Primary Examiner* — Robert B Mondesi
*Assistant Examiner* — Mohammad Y Meah
(74) *Attorney, Agent, or Firm* — Sam J. Barkley

(57) ABSTRACT

Disclosed herein are microorganisms that have enhanced tolerance to toxic compounds found in thermochemical waste streams. Methods of utilizing carbon found in waste streams are also disclosed. Also presented herein are methods for detoxifying waste streams and methods of bioconversion of toxic waste stream materials into useful products.

5 Claims, 25 Drawing Sheets

Specification includes a Sequence Listing.

1A
ATGCGAATAGACCGTTAACCAGCAAGCTTCAATTGCAATATCCGATGCCCAGTCTTTGGCCTTGCACCTTGGCATGGACCACCCTGCCATCGAGCCCGTGCACCTGTTACAGGCGCTGCTGTCTGAACAGCAGGGGCGCTCCATC
AAACCGTCTGATGCAGGTAGGCTTCGACATGTCAATGGCCTTGCTGGCCGAAGAGCTGAAATACAGAAGCTGCCAAATACAGAAACCTACCGGCGACGTGAACATGTCAGGCACTGGCACGTCTGCTTA
ACCAGGCAGAGCCCTGGCACTGCAGAAGGGCGACCAGTTCATTTCCAGTGAACTGGTTCTGCTGGCCGCCATGGACCACCCTGCCATCGAGCCCGTGCACCTGCTGCAGGCGCTGCTGGAGCAGCAGGG
GAAAATGCCATCAACAACCTGCGTGGCGGCGCTACCGTGCAGTGAATGACGCCGTAGTCAGCCCAGCCGCCATCGACGTCAAGCTGATCTGACCTAAAACCGCGACCCAAGGCCTGCCCAGGCATCAATGGTG
GCCCTGACGATGAAATCCGCGATGGCCTCAAAGGCCTCAGTGCGTACCGTGCAGCTGGCGCTGATCGGTGCAAGGTTGAAGAGCCTGTCTGCCCAGGCGAGCTGCATTGCTGAACGAACTGTCAAGCAGGAAGGCC
AAGTCCCGACGACGTCTCAAAGGCCAAGCTGCACCATGACCGCCCGAACATGTCCAAGCCGTGGAGTTCAAGAGACGTACCGGTGAGTTCAAGAAGCCTGTGAAAAGCTGCTGAACTCGTCAAGCAGGAGGCCGAA
AGATCATCTGTTCATCGACGCGGTGCAATCACCGGCGCGCTTCATCGAAAAGGACGACATCGCCGTCTGCTGCCGCCTGATCAGGGCGTGTGTGAGGAAGGCCATTGACTGTGAAGAGCGCATCTCGTGAAGAGCGTGACCGAGAACTGCTGAAC
CGAGTACCGCCAGTTCATCGAGAAAAGGACGACATCGCCGTCTGCTGCCGCCTGATCAGGGCGTGTGTGAGGAAGGCCATTGACTGAAAGAGAGCGCATCTCGTGAAGAGCGTGACCGAGAACTGCTGAAC
GGTGGCCATCACCGACGCCTGCAATCTGGTCCGGTGAAAATCGAGGCTTCGACTCGAGTGCGATCCGGAGACTGGTGGCACTCTGGTAGCGAAAGGCCGCGCTGTCGGTATCG
AGCGCGGCGAACTGCACTGCGTGGAATCCCGGAGAAGGCGGGTGATGTCCTGTGAAGGGCTGGGCCAAGTGTTGCCTGGCACACCGCGAGAGTCTGTTGGGCCAAGAGCCGTGAGCCGAGTTCCTGAAGAGCCGGAAGATGCCTGGTGTGCTGGA
GCGTGGTGAATTGCAGAGCCCGGATTGTTCAACGTGGGTACGGAGGCACAGTGCCGATGATGTCTGGAAAGGCCACGGTCCGTCCGAATTCATCAACGACAAGCTTGATTGCCGTGGGATGTGCCGTGGGTATGCCGTGGGCTCG
CGAGATTCAGGAACTGGGTGACCGGAAATCAGCTCGGCGGTGACGATCGGCGCCTGCTGAGCGGACAGTCGTGTGAGGCGGAACTGCTGTTGAGGCGCCTGAGGCCTGGAAAATGGCCCAGGCGTTGAGGACAGACCCGGAGCTTGGAGCCTTTGAGCCTTGGCGGCGAG
CAGATTGCCGGTATTACAGAAATCAGCTGCGGTGACGATCGGCGCCTGCTGAGCGGACAGTCGTGTGAGGCGGAACTGCTGTTGAGGCGCCTGAGGCCTGGAAAATGGCCCAGGCGTTGAGGACAGACCCGGAGCTTGGAGCCTTTGAGCCTTGGCGGCGAG
GGCCGCTGAAGCTGTGATCCAGGAGCCTGCTGAAGCTGTGATCCAGCGTCCGCGATCGAGAACCCGTCTGCCGCAGTTCCTGCCGCAGTTCAAGAGATCTTGGCCGGATGAACCCGCAAGGTGGAAGGCGACGAAATCGTCTTTGGC

1B
MRIDRLTSKLQLAISDAQSLAVGMDHPAIEPVHLLQALLEQQGGSIKPLLMQVGFDINGLRQGLVKELDQLPKIQNPTGDVNMSQDLARLLNQADRLAQ
QKGDQFISSELVLLAAMDENSKLGKILLSQGVSKKALENAINNLRGGAAVNDANAEESRQALDKYTVDLTKRAEEGKLDPVIGRDDEIRRTVQVLQRRTK
NNPVLIGEPGVGKTAIAEGLAQRIINGEVPDGLKGKRLLALDMGALIAGAKYRGEFEERLKSLLNELSKQEGQIILFIDELHTMVGAGKGEGAMDAGNMLK
PALARGELHCVGATTLNEYRQFIEKDAALERRFQKVLVEEPSEEDTIAILRGLKERYEVHHKVAITDGAIIAAKLSHRYITDRQLPDKAIDLIDEAASRIRME
IDSKPEVIDRLDRRLIQLKVESQALKKEEDEAAKKRLEKLTEEIERLEREYSDLEEIWASEKAEVQGSAQIQQKIEQSRQELEAARRKGDLNRMAELQYGVIP
DLERSLQMVDQHGKTDNQLLRNKVTEEIAEVVSKWTGIPVAKMLEGEREKLLKMEELLHQRVIGQSEAVTAVANAVRRSRAGLSDPNRPSGSFFLFGPT
GVGKTELCKALAEFLFDTEEAMVRIDMSEFMEKHSVARLIGAPPGYVGYEEGGYLTEAVRRKPYSVVLLDEVEKAHPDVFNVLLQVLEDGRLITDSHGRTV
DFRNTVIVMTSNLGSAQIQELVGDREAQRAAVMDAVGAHFRPEFINRIDEVVFEPLGREQIAGITEIQLGRLRSRLLERELSLSLSPEALDKLIAVGYDPV
YGARPLKRAIQRWIENPLAQLILAGKFLPGTAITAKVEGDEIVFG

ATGAAAACCACAATTTGGGAGAGATCGACAATGAAACTTGTCCTCGCAGCGAAGAAGAATCGAAAACCGTTGGGCGTATCGTCCTGCGGGTTCGGCCGC
TGAAAACCAAACCGCGGGCGAAGTTGTAGCCGTGCACCGGTCCTGGACAACGGCGAAGTTCGCGCCGTGAAGTTGGTTTCGGCCGCGTACTCGGGCAGC
AACACCGTGAAAGTCGATGGGCGAAGACCTGCTGCTGGTCATGGCCGAGAACGAAATCCTCGCCGTTGTCGAAGGC

2B

MKTTIWERSTMKLRPLHDRVVIRRSEEESKTAGGIVLPGSAAEKPNRGEVVAVGTGRVLDNGEVRALAV
KVGDKVVFGPYSGSNTVKVDGEDLLVMAENEILAVVEG

ATGGCTGCTAAAGACGTAAAATTTGGTGATTCCGCTCGTAAGAAAATGCTGGTTGGTGTCAACGTTCTGGCTGACGCGGTAAAAGGCGACCCTGGGCTGTAACGTGGTACTGGCCA
AGAGCTTCGGCGTGACCATCACCAAGGACGGCGTTTCCGTCGCAAAGAAATCGAGGTAGCGCTTTCGAAACATGGGCGCCCAGTGGTCAGTGGTCTTCCAAGGAAGTTGCTTCAAGGCCAACGA
CGCTGCCGGTGACGGCACCGACCTGTTCGGCTCAGGCCATGCTAACCTGTCAAGGCCATGAACCTCGACAACTCCATCGCCGGTATCGAAGCGCGGTATCGAACGCGAAGCGCACTG
CTGCCGTCGTTGCCGAACTGTGAAGAACCTGTCAAGGACGTAGGTACCATCTGCCGCCAGTGGTACCAACTGTCGTCGTAGAAGCATGGAAACGAACGAACTCCGTGAAATCATCGCCGAAGCCATGG
AAAAGTCGGTCAAGGTGGTAGCTGGAAGCCGCTGTCGATCACCGTTGAAGAAGGCGTGATCACCGTTGAAGAAGGCTGGGCGTCCGAGTGTCGATCACCGTTGAAGAAGGCGACCTGTTGCCGAAGGCCATGTCAACAAGCC
GGACACCGATGGTTGCCGAGCTGGAAGGTCAAGGCGTGACTGGTCGCGGCCCGCTGGTCGCTGCTGACAACATCCAACATCCGCGGCATGCTGCCAGTTCTGAAGGCCTCGAAGGCTGTTCCTCTGCCGGCCCGCCACTGTCGATCG
TTGCCGAAGACGTTGAAGGTGAAGCGTGGGCCAGTGCTGAGCGAAGTTGCTGACAACCTGGTCAGTGACGTACCGAAGTTGCTGACAACCTGGTAACGCTGTCTCCGAAGCCATGTGCCGCAAGGCCATGTCGAGGA
CATCGCTGTCCTGACTGGCGGCTGACACGGCCAGTGCATCTCCGAAGAATCGGCTGTCCTGGAAACCGTCATCTGCCTGGAAACCGTCATCTGCGGTAACGCCAAGCCGTCATCGTCGAGAGCGTCATCGTCGAGAGCGTCATCGTCGAGAGCGTCATCGTCGAGAGCGTCATCGTCGAGAGCGTCATCGAAGCCATCAT
CGACGGTCTGGGCGCTGACAGCGGCAGCGTCGGTGCCGGTGACAAGGTCGGTGACGATCGAAGCGAATCCGAAGCAGATCCAAGCAGATGAAGCAGATGAAAGCGCCGAGCTGTGAAGCGTGAAGCGTGCTGGCGGT
GGTGTTGCCCCTGGTGATGAGCCAAGCGTGGTGCTGCAAGCTGTCGACTGAAGCAAGGTTCGGGCAACCTGGAACCCGAGACACTCGGGCTACAACGCCGGTGAATACCGCTACGACCTGGAAGCAAGCCGGAACATGATGAGATCGAGATCACTGCGCC
GCCGGTGATGAGCCAAGCGTGGTTGCTGACAGCGTCGGCGGCTGCGTCGGCGGCGCCAAGCGTGGCGCTGATGCTGACAAGCCAGCCATGGTTGCCGAAGACAAGCCAGCCATGGTTGCCGAAGACAAGACAAGCCAGCCATGGTTGCCGAAGACAAGACAAGCCGAAGACAAGCCAGCCATGGTTGCCGAAGACAAGACAAGCCAGCCATGGTTGCCGAAGACAAGACAAGCCAGCCATGGTTGCCGAAGACAAGACAAGCCAGCCATGGTTGCCGAAGACAAGACAAGCCAGCCATGGTTGCCGAAGACAAGACAAGCCAGCATGGT
TCACTCGCTGGCGCTGCAAGCTGCTGCTTCGATCGGCGGTCGTCTGATGATCACCGGGCATGGGCGGGGGCATGATG
GGCATGGGCGGCATGATG

3B

MAAKDVKFGDSARKKMLVGVNVLADAVKATLGPKGRNVVLAKSFGAPTITKDGVSVAKEIELKDAFENMGAQLVKEVASKANDAAGDGT
TTATVLAQAIVNEGLKAVAAGMNPMDLKRGIDKATAAVVAELKNLSKPCADSKAIAQVGTISANSDNSIGEIIAEAMEKVGKEGVITVEEGS
GLENELSVVEGMQFDRGYLSPYFVNKPDTMVAELEGPLLLIVDKKISNIRELLPVLEAVAKAGRPLLIVAEDVEGEALATLVVNNMRGIVKV
AAVKAPGFGDRRKAMLQDIAVLTGGQVISEEIGLSLETATLEHLGNAKRVILSKENTTIIDGAGADTEIEARVKQIRAQIEETSSDYDREKLQE
RLAKLAGGVAVIKVGAGTEVEMKEKKARVEDAIHATRAAVEEGVVPGGVALVRALAAIIDLKGDNEDQNVGIALLRRAVESPLRQITANA
GDEPSVVADKVKQGSGNFGYNAATGEYGDMIEMGILDPAKVTRSALQAAASIGGLMITTEAMVADLPEDKPAAGMPDMGGMGGMG
GMM

```
GACACCATGCGCCATCCTGCGTGGCCTGAAAGAGAGCGGCTATGAAGTGCACCACCAAGGTGGCCATCACCGACGGTGCAATCATCGCTGCGGCCAAGCTCAGCCATCG
CTACATCACCGACCGCCAGCTGCCGGACAAGGCTGCCATTGACCTGATCGACGAAGCGGCCAGCCGCATCCGCATGGAGATCGACTCCAAGCCGAAGTGCTGACC
GCCTTGATCGCCGCCTGATCCAGCTGAGTATTCCGACTGTGAAGGTGGAGTCGCAGGCGCTGAAGAAATCGAAGTGCAGGCGCAAAAGCGGCGAAAAAGCGCTGACCGAGGAAA
TCGAGCGGCTGAGCGTGAGCGCGTGAGTATTCCGACTGTGAAGAAATCTGGGCTTCGGAGCGCAGATCGGCGCAGATCCAGCAAAGATCGAGCAGTC
TGCCCAGGAGCTGGAAGCGCAAGCGACAACCAGTTGCTGCCGCAACAAGGTCTGCGCAACAAGGGTGACTGAACCGGAACGACTGGGGGTGATCCGAGCTGCAGATCCAGCGCTGCAGATGGTC
GACCAGACACGCAAGACCAAGACCAGTTGCTGCTGAAGATGGAAGAGCTGCTGAAGAAATTGCCAGAGCGCGTAACCGGTAACCGCCGTAGCCAACGCCGTAC
TGCTCGAAGGCGAGCGTGAGAAGCTGTCGAACCGGCCAAGTGGTCTTCGACCGCCAAGTGGGCAAGACCGGTGTGGCCAGGCAAGTGCAAGGCGCTGGCC
GCCGCTCGCGTGCGGCGTGTCGAAACGGCGAAGAGGGCGGTTACCTGACGGCGTGCGGCGAGCGCCTGACAGCGCCGCGCCTGATCGGTGCACCACCAGGCTATGT
GAGTTCCTGTTCGACACCGAAGAGGGCGGTTACCTGACGGCGTGCGGCGAGCGCCTGACAGCGCCGCGCCTGATCGGTGCACCACCAGGCTATGT
AGGGTATGAAGAGGGCGGTTACCTGACGGCGTGCGGCGAGCGCCTGACAGCCGTGATCGTGTGAAAAGCCACCGGATGTGTTCAAC
GTGCTGTTGCAGGTGCTGGAAGAACTGGTGGGGTGACCGGTGAGGGCGAGTGGATCGGTCCGAATTCATCAACCGCATCGACGAA
GCAGATTCAGGAAGAACTGTGGGGTGACCGGAGGCAGAGCGTGCGGTATTGCCGGTATGCCGGTGACAGATTGCCGTGGGTTATGACCGGTGACAGGCGGATCAGGCGCTGAGATCGAGAACCCG
GTGGTGTGTTCGAGCCTTTGGGACAAGCTGATTGACACCAGTGCCGGCAGTGATACAGAAATCCAGTCGCCGCCTGCTGGAGCGGAACTGTCGTTGAG
CCTGAGCCAAGCGCGTGATTCGCCGGCAAGTTCCTGCCGGTACGGCGATCACCGCCAAGGTGGAAGGCGACGAAATCGTCTTTGGCTGATTGTTGCACCATGAG
CTGGCGCAGCTGATTCGCGGGGCTATGAAACGCGTCCTGCCGTATCGTCCTGCGGGTTCGGCGTAGTCGTCGCAGCGAAGAAGAATC
CCCGCGTTGCGCCGGCTATGAAACGCGTCCTGCCGTATCGTCCTGCGGGTTCGGCGTACTCGGCGAAGTTGTAGCCGTGCGTCGGACAACGGCGAA
GAAAACGCTGGCGCTGGCCGTGAAAGTGGGTGACAAGTGGTTTCGGCCGACTTCGGCCGTACTCGGGCAGCAACACCGTGAAAGTCGATGGCGAAGACCTGCTGGTCATGCCG
GTTCGCGCGCTGGCCGTGAAAGTGGGTGACAAGTGGTTTCGGCCGACTTCCCGACTTGATTTCCCGACTTCCCGTACTCGGGCAGCAACACCGTGAAAGTCGATGGCGAAGACCTGCTGGTCATGCCG
AGAACGAAATCCTGCCGTTGTCGAAGGCTGAATTTGGTGATTCCGCTCGTAAGAAAATGCTGGTTGTCAACGTTCCGTCGCCAAAGAACGATGAAGCGACCGTAAAGCGACCGGGCCCGAAAGCC
GGCTGCTAAAGACGTAAAATTTGGTGATTCCGCTCGTAAGAAAATGCTGGTTGTCAACGTTCCGTCGCCAAAGAAATGAGCTGAAAGACGCGTTTGAAAACATGGGC
GTAACGTGGTACTGGCCAAGAGCTTCGGCGCCGACGGCTTGCTTCAAGGAAGTTGCTTCAAGGAAAGTTGCTTCCAAGGAACCGATGAGCGCCATGTCTCGGCCTGCAGGTCAACGGCCATGCATGGCG
GCCAGCTGGTCAAGGAAGTTGCTTCAAGGAACCGATGAGCGCCATGCTGCCGAAGCGCGGTATCGACAAGGCCACTGGTATCGACAACCTGCTGCCGTCGTTGCCGAACTGAAGAACCTGTCCAAGCCATGCGCCG
AGCCGTGCTGCCGGACATGCCCAGGTAGGTAGCCCATCTCTGCCAACTCCGACAACTCCATCGTTGACAAGGCCACTGGTATCGACAACCTGCTGCCGTCGTTGCCGAACTGAAGAACCTGTCCAAGCCATGCGCCG
ACTCCAAGGCCATCGCCCAGGTAGGTAGCCCATCTCTGCCAACTCCGACAACTCCATCGTTGACAAGGCCACTGGTATCGACAACCTGCTGCCGTCGTTGCCGAACTGAAGAACCTGTCCAAGCCATGCGCCG
ATCACCGTTGAAAAGGCTCGGGCTGGAAAAGGCCTGAGAAAACGAACTGTCCGTCGTAGAAGGCATGCAGTTCGAGAAGCATGGAAGAAGCGGTAAAGAAGGCGTG
CACCATGGTTGCCGAGCTGGAAGGCCCGGCTGCCGAGCTGGAAGGCCCGGTCGGAAGGCCTGCCGAGCTGGAAGGCCCGGTCGGAAGCGCCGGA
GCCGCCACTGCTGATCGTTGCCCGAAGGCCATGCTGCCGAAGACGTTGAAGGTGAAGGCGCTACCCTGGTAGTCAACAACATGCCGGTAGTCAACAACATGCCGGCTAGTCAACAACATGCCGGCTAGTCAACAACATGCCGGTCAGTCAAGGCT
CCGGGGCTTCGGCGATCGCCCGCAAGGCCATGCGTGCCGAAGACGTTGAAGGTGAAGGCGCTACCCTGGTAGTCAACAACATGCCGGAAGAAATCGGCGTCGTCCCTGAAACCGCTAC
CTGGAGCACCTGGGTAACGCCAAGCGCGTCATCCTGTCCAAGGAAAACACCACCATCATGGAGCGCGCTGGCGTGCTGACCGGTGCTGAAGCGCGCGCGCGCGCAAGC
```

FIG. 4 (continued)

AGATCCGTGCCCAGATCGAAGAAACTTCCTGGACTACGACCGTGAGAAGAGCGTCTGGCCAAGCTGGCTGGTGTTGCCGTGATCAAGGTCGGT
GCCGGCACCGAAGTTGAAATGAAAGAAGAGAAAAGCCCGCGTTGAAGACGCCCTGACCCTGAAGCAGCCGTTGAAGAAGGCGTGGTGCTGGCGGTGGT
GTTGCCCTGGTTCGCGCCCTGGCAGCCATCATCGACCTGAAACGTGGTATCGCGCGCTGCGTGCGCTGTTGAATCCCGCT
GCGCCAGATCACTGCCAACGCCGGTGATGAGCCAAGGTGGTTGCTGACCAAGGTTCGGGCAACTTCGGTACAACGCCGTACCGGTGAATAC
GGCGACATGATCGAGATGGGTATCCTGGACCAAGCCAGCAGCCAGCTGCTGCTGCAAGCTGCTGATCGGCGGTCTGATGATCACCACCGAAGCCAT
GGTTGCCGACCTGCCGGAAGACAAGCCTCCGACCGAGGCTTTGACTGTTGCGTAAATCTTCCCAAAATGCATCCGTAAACACCTGATTCTATTGGGGTCGAAACGAACAA
ATCAAAATAGTCAAAAGCCCAATTCCGATGCGCCATATTTGCTTTAAGGCATTGATTAACTGGCGTCCCAGGCTTTGATGCGTAGAGCGTGTAG
AAAAGGCGCAATTCCGATGCGCCATATTTGCTTTAAGGCATTGATTAACTGGCGTCCCAGGCTTTGATGCGTAGAGCGTGTAG
GTCATTGTGTACATTGGGGTTGCAAGGATGTGTTCAAGCGACCAGACGCTGAAGCGTGAGAGGCTTCCTCCGGGAACGATCCTCGCGGGCCACGCCCGTGGCGC
CCCTGTTTATTGATCAGGATGTGTTCAAGCGACCAGACGCTGAAGCGCTGAAGCGGCTGGTGCGCCGTGTTGCTGTTCGGCTGTGCGCAGATCGAAGGCGTCTG
CAGGTTGAGCCAGAACTCAGGGTGGTGTCCAGGCAGATGAGCAGGGCGGCGTTCGGCGAAACTCTCCGCAGGATTCACCGAGGATGGATGGACGCATACCG
GGCGTTGCTACACCCAACGCCCTGCCAGAGCCGGGCGAAGCGCTGAAGCCCATTCTCTCCGCAGGATTCACCGAGGATGGATGGATTACACGGATACT
TTCTTGAGCATGATGCACCTCAGTGGTCACCTCAGTGATCGAACAATTTCAACGTTAACTGGCCTGTCCCTGTCTCCCAGTGAAGCACAACCGCCATTGGTCATTTACAGGATACT
GTGCTGGTCGGGCGGGTTGCCGCTCAGTGACTCAGTGAAGGCGATTGCCAGGTGGCACTAAGGTCTCGCAACTCTGTTGCCGCATCGAGCATGGCCAGCTTGCGCT
CCGCGACTGACTTGATATCGACCCGCTGATATCGACCCGGTGTCTTCCCGTTGTGAAGAGCGCTTCCGTGAGCAAGAGCCGTTAACAGTCGCAAGCTCGATCATGAGCTGAATCATGAGTCGAATGCTTAACGT
TATTCGTTAATTCGATTATACGACGGGATCTTCAAGTCTGTAGTTCAAGCCCGAACCGGTCGCGCCGCTAACATATTGTTCAATGGCGATGTTTCGCCTTGCTATCGTTCTGGTTC
CATATTCCCCGTCACCTGCGACTATCGTGCAGGCGCATCGTGCAGGCGCTAACATATTGTTCAATGGCGATGTTTCGCCTTGCTATCGTTCTGGTTC
ACAAAGGAAGCTTTCCCGGATGCAGTCGCTACACCGTTCTCATCGTCTGCTGACGCTGGTCAGCCTGTCGAAGCCTGTCGAACGCATGCAAGCTTGGCA
CTGGCCGTCGTTTACAACGTCGTGACGGAATGCCAGGAAGTCCGGCGAATTGCCAGGAATTGGGAATTGGAAGCCCTGCAAACAGGATGAGGATCGTTCGCATGATTG
AACAAGATGGATTGCACGCAGGTTCTCCGGCGCTTGGGTGGAGAGGCTATTCGGCTATGACTGGGCACAACAGACAATCGGCTGCTCTGATGCCGCCGTGTTC
CGGCTGTCAGGCAGGCGCAGGTTCCGCGCAGGTCCGGTCCGGTTCTTTTGTCAAGACCGACCTGTCCGGTGCCCTGAATGAACTGCAGGACGAGGCAGCGCGGCTATCGTGGCTGGCCAC
GACGGGCGTTCCTTGCGCAGCTGTGCTCGACGTTGTCACTGAAGCGGGAAGCGGTCGCTATTGGCGTTGGGAAGTTGCCGGGAATCCGTGTCATCTCACC
TTGCTCCTGCCGAGAAAGTGATTGCACGCAGGTTCTCCGGCCGCTTGATCGGTCGATGCAATGCGGCGGCTGCATACGCGTTGATCGGTGTCCCAGCCAAGCTCCAAGCGAAACATCGCATCG
AGCGAGCACGTACTCGGATGGAAGCCGGTCTTGTCGATCAGGATGATCTGGACGAAGAGCATCAGGGGCTCGCGCCAGCCGAACTGTTCGCCAGGCTCAAGGC
GCGGATGCCCGACGGCGAGGATCTCGTCGTGACCATGGCTGATGCAATGCGGCGGCTGCATACGCTTGATCCGGCTACCTGCCCATTCGACCACCAAGCGAAACATCGCATCG
GGCTGGGGTGTGCGGACCGCTATCAGGACATAGCGTTGGCTACCCGTGATATTGCTGAAGAGCTTGGCGGCGAATGGGCTGACCGCTTCCTCGTGCTTTACGGT
ATCGCCGCTCCCGATTCGCAGCGCATCGCCTTCTATCGCCTTCTTGACGAGTTCTTCTGAGCGGGACTCTGGGGTTCGAAACATCAAAAAGGTTGCAAACAACATCAAACAAGCAACAGTATTAA
CCTTTACTACCGCACTGCTGGCAGGAGGCGCAACTCAAGCGTTTGCGAAAGAACGAACCAAAGCCATATAAGGAAACATACGCCATATTCCCATATTACACGCC
ATGATATGCTGCAAATCCCTGAACAGACAGCAAAAATGAAAAATATCAAGTTTCGTCCACAATTTGATTCGTCCACAATTTGATTCGTGAATTTCGAATTTCTGCAAAGGCCTGGACGT

FIG. 4 (continued)

TTGGGACAGCTGGCCATTACAAAACGCTGACGGCACTGTCGCAAACTATCACGGCTACCACATGTCTTTGCATTAGCCGGAGATCCTAAAAATGCGGATGACAC
ATCGATTTACATGTTCTATCAAAAGTCGGCGAAACTTCTATTGACAGCTGGAAAAACGCTGGCCGGCGTCTTAAAGACAGGACAAATTCGATGCAAATGATTCT
ATCCTAAAAGACCAAACACAAGAATGTTCAGGTTCAGCCACATTACATCTGACGGAAAAATCCGTTATTCTACACTGATTTCTCCGTAAACATTACGGCAAAC
AAACACTGACAACTGCACAAGTTACGTATCAGCATCAGACAGCTCTTTGAACATCAACGGTGTAGAGGATTATAAATCAATCTTTGACGGTGACGGAAAAACGT
ATCAAAATGTACAGCAGTTCATCGATGAAGGCAACTACAGCTCAGGCGACAACCATACGCTGAGAGATCCTCACTACGTAGAAGATAAAGGCCACAAATACTTA
GTATTTGAAGCAACACTGGAACTGAAGATGGCTACCAAGGCGAAGAATCTTTATTTAACAAAGCATACTATGGCAAAAGCACATCATTCTTCCGTCAAGAAAGT
CAAAACTTCTGCAAAGCGATAAAAAACGCGATCAAGATGAAATTGAACGCGAACGTCTTTAAAATGAACGCAAATGGTACCTGTTCACTGACTCCCGCGATCAAAAAT
ACCGCTGATTGCATCTAACACAGTAACGATAACGATATTTACGATCTAACTGCTTGGTTATGTTTCTAATTCTTAACTGGCCCATACAACAATGTGCTGAACAAACTGGCCTTGTGTTAAAAA
GACGATTGACGGCATTACGCTAACGATGTAACGATATTTACGATCTAACTGCTTGGTTATGTTTCTAATTCTTAACTGGCCCATACAACAATGTCGTGATTACAAGCTATATGACAAACAGAGGATT
TGGATCTTGATCCTAACGATGTAACCTTTACTTACTCACACTTCGCTGTACCTCAAGCGAAAGGAAACAATGTCGTGATTACAAGCTATATGACAAACAGAGGATT
CTACGCAGACAACAATCAACGTTTGCGCCGAGCTTCCTGCTGAACATCAAAGGCAAGAAGAAAACATCGTTGTCAAGACAGCATCCTTGAACAAGGACAATTAAC
AGTTAACAAATAATCAGACCCCGTAGAAAAGATCAAAGGATCTTC

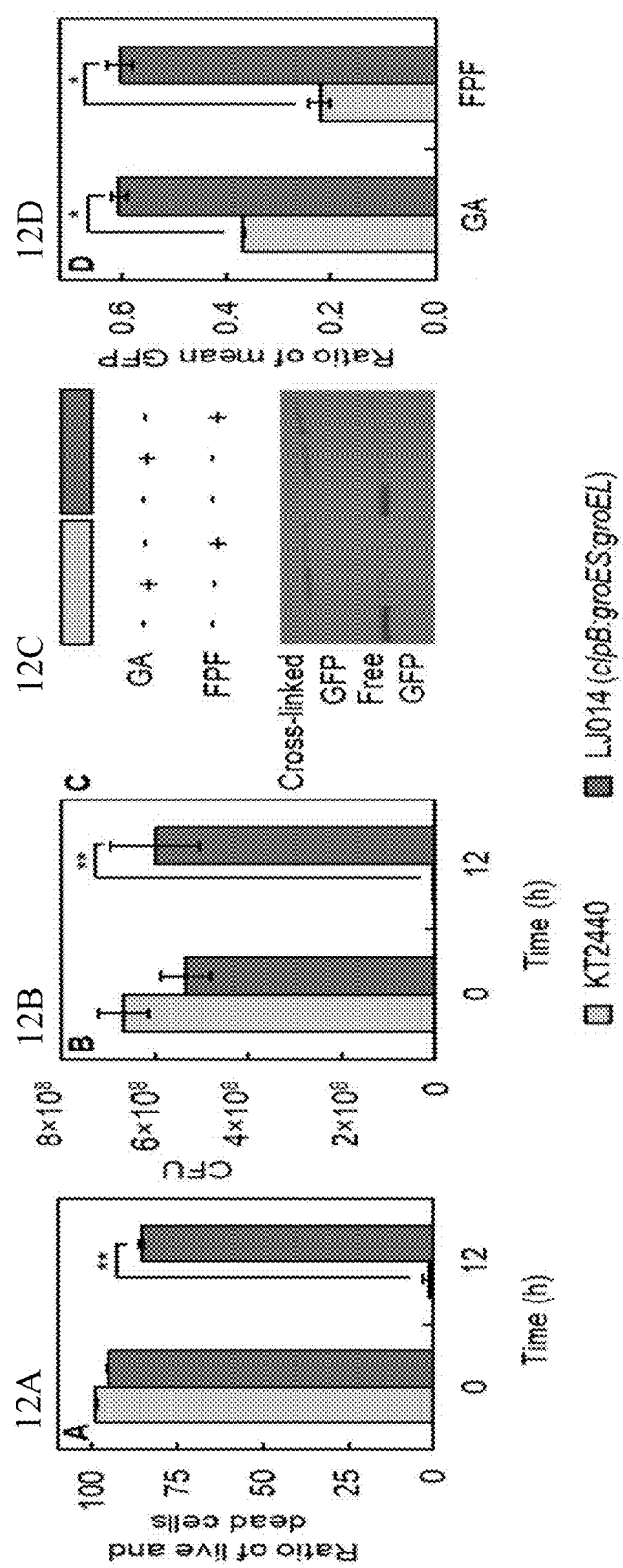
FIGs. 12A, 12B, 12C, and 12D

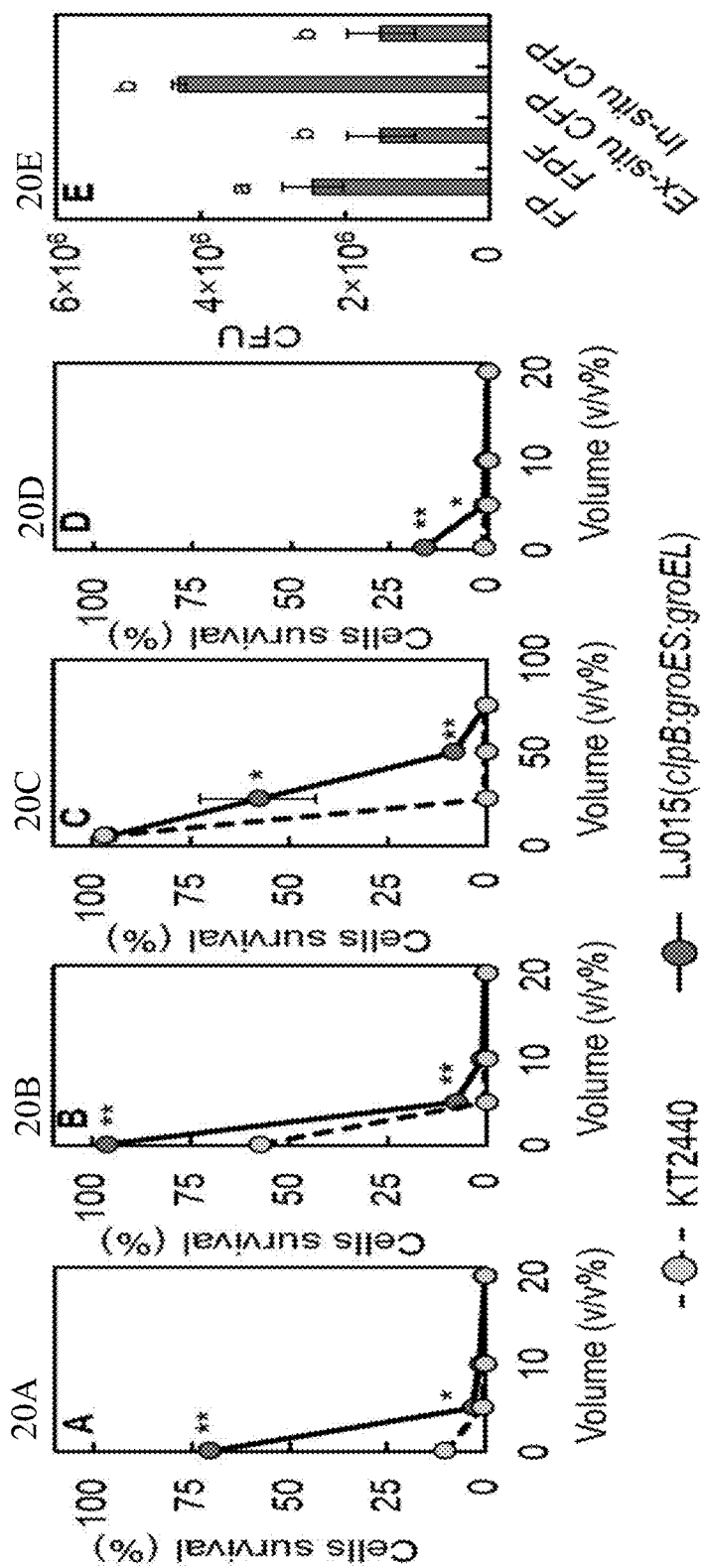
FIGs. 20A, 20B, 20C, 20D, and 20E

BIOCATALYSTS FOR CONVERSION OF THERMOCHEMICAL WASTE STREAMS

CROSS-REFERENCE TO RELATED APPLICATIONS

This application claims priority under 35 U.S.C. § 119 to U.S. Provisional Patent Application No. 62/621,891 filed on Jan. 25, 2018, the contents of which are hereby incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy, created on Jan. 25, 2019, is named NREL_18-36_seq_listing_25Jan2019_ST25.txt, and is 33 kilobytes in size.

BACKGROUND

Lignocellulosic biomass can enable the production of renewable fuels and chemicals and will be an essential resource to mitigate climate change. There currently exists a diverse portfolio of biomass conversion technologies at varying stages of development from laboratory and pilot-scale, to several demonstration and industrial-scale processes around the world. Biomass conversion generates wastewater containing dilute carbon and inorganic components, which typically are treated via standard wastewater approaches such as by combustion or oxidation to generate low-grade heat or anaerobic digestion to produce low-value biogas. These waste streams are both a cost and a loss of potential high-value products for a biorefinery.

SUMMARY

In an aspect disclosed is a non-naturally occurring *Pseudomonas* cell that overexpresses one or more genes encoding for chaperone polypeptides. In an embodiment, the cell has chaperone polypeptides that are GroES, GroEL and ClpB. In another embodiment, the cell has chaperone polypeptides that are HscB chaperone polypeptides. In an embodiment, the cell has genes that are incorporated into the genome of the *Pseudomonas* cell. In an embodiment, the cell has genes that are operably linked to a constitutive promoter. In an embodiment, the cell has a constitutive promoter that is the lac promoter. In another embodiment, the cell is capable of metabolizing at least 82% of the available carbon within 72 hours in a waste stream resulting from the pyrolysis of biomass. In an embodiment, the cell is capable of a 83 fold or greater survival rate in comparison to the naturally occurring *Pseudomonas* from which it is derived after 12 hours of growth in a waste stream from the pyrolysis of biomass. In another embodiment, the cell is able to grow in waste stream solutions containing concentrations of compounds that do not allow for the growth of the naturally occurring *Pseudomonas* from which it is derived from; the concentrations of compounds selected from the group consisting of greater than 7.5 times the concentration of aldehydes, 1.5 times the concentration of ketones, 3.5 times the concentration of acids, 3.5 times the concentration of phenolics, and 1.5 times the concentration of alcohols.

In another aspect, disclosed is a non-naturally occurring *Pseudomonas* genetically engineered to have increased intracellular levels of ATP when compared to the wild type *Pseudomonas* from which it is derived and wherein the non-naturally occurring *Pseudomonas* overexpresses one or more genes encoding for chaperone polypeptides. In an embodiment, the non-naturally occurring *Pseudomonas* is capable of growing in a 200 fold higher concentration of carbon compounds in waste water generated from the pyrolysis of biomass when compared to the wild type *Pseudomonas* from which it is derived. In an embodiment, the non-naturally occurring *Pseudomonas* is capable of metabolizing at least 12 g/L of the available carbon in a waste stream resulting from the pyrolysis of biomass. In an embodiment, the non-naturally occurring *Pseudomonas* has chaperone polypeptides that are at least GroES, GroEL and ClpB. In an embodiment, the non-naturally occurring *Pseudomonas* has chaperone polypeptides that are at least a HscB chaperone polypeptide. In an embodiment, the non-naturally occurring *Pseudomonas* has genes that are incorporated into the genome of the *Pseudomonas* cell. In another embodiment, the non-naturally occurring *Pseudomonas* of claim 10 has genes that are operably linked to a constitutive promoter. In an embodiment, the non-naturally occurring *Pseudomonas* is capable of metabolizing at least 82% of the available carbon within 72 hours in a waste stream resulting from the pyrolysis of biomass. In an embodiment, the non-naturally occurring *Pseudomonas* is capable of a 83 fold or greater survival rate in comparison to the naturally occurring *Pseudomonas* from which it is derived after 12 hours of growth in a waste stream from the pyrolysis of biomass. In another embodiment, the non-naturally occurring *Pseudomonas* is able to grow in waste stream solutions containing concentrations of compounds that do not allow for the growth of the naturally occurring *Pseudomonas* from which it is derived from; the concentrations of compounds selected from the group consisting of greater than 7.5 times the concentration of aldehydes, 1.5 times the concentration of ketones, 3.5 times the concentration of acids, 3.5 times the concentration of phenolics, and 1.5 times the concentration of alcohols.

In an aspect, disclosed is a method for metabolizing waste stream products from the pyrolysis of biomass comprising treating the waste stream products with a *Pseudomonas* genetically engineered to have increased intracellular levels of ATP when compared to the wild type *Pseudomonas* from which it is derived and wherein the non-naturally occurring *Pseudomonas* overexpresses one or more genes encoding for chaperone polypeptides.

The foregoing examples of the related art and limitations related therewith are intended to be illustrative and not exclusive. Other limitations of the related art will become apparent to those of skill in the art upon a reading of the specification and a study of the drawings.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1A depicts the nucleotide sequence (SEQ ID NO: 1) and FIG. 1B depicts the amino acid sequence (SEQ ID NO: 2) of ClpB.

FIG. 2A depicts the nucleotide sequence (SEQ ID NO: 3) and FIG. 2B depicts the amino acid sequence (SEQ ID NO: 4) of GroES.

FIG. 3A depicts the nucleotide sequence (SEQ ID NO: 5) and FIG. 3B depicts the amino acid sequence (SEQ ID NO: 6) of GroEL.

Figure 4:
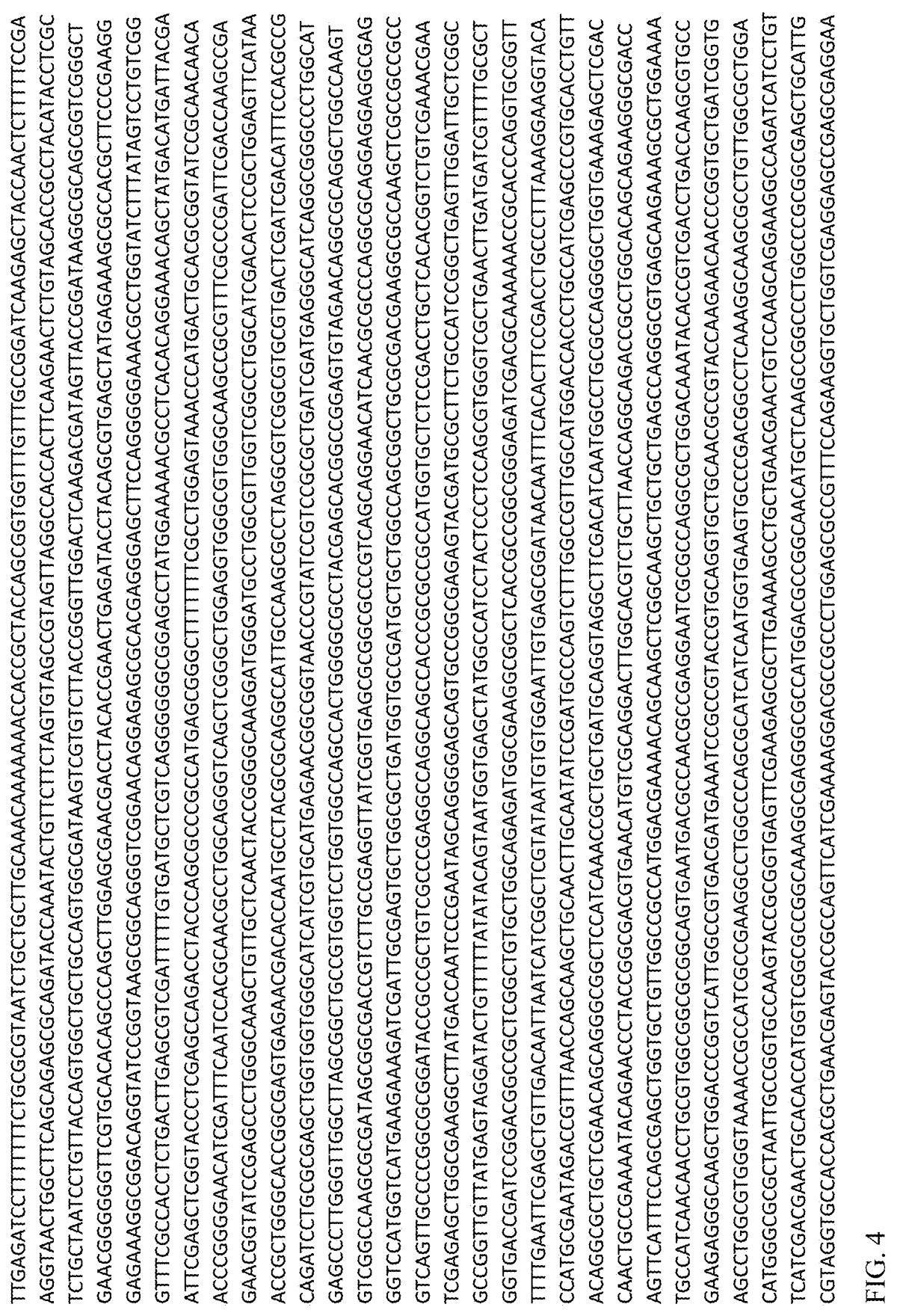

FIG. 4 depicts the nucleotide sequence (SEQ ID NO: 7) of integrated plasmid (pK18sB-PP_1584: Ptac-clpB-groES-groEL).

FIGS. 12a and 12b depicts cell viability of native *P. putida* KT2440 and non-naturally occurring *P. putida* strain LJ014 which includes clpB, groES and groEL genes capable of expressing additional chaperones. FIGS. 12c and 12d depict the expression of green fluorescent protein in *P. putida* KT2440 and non-naturally occurring *P. putida* strain LJ014 associated with the expression of the clpB, groES and groEL genes after exposure or non-exposure to (glycolaldehyde) GA and FPF.

FIG. 20 depicts cell survival of naturally occurring *P. putida* strain KT2440 and non-naturally occurring *P. putida* strain LJ015 at different concentrations of TC wastewater streams: (A) FP, (B) FPF, (C) in-situ CFC, (D) ex-situ CFP, and (E) CFU at maximum tolerable concentration (v/v %).

DETAILED DESCRIPTION

Figure 5:
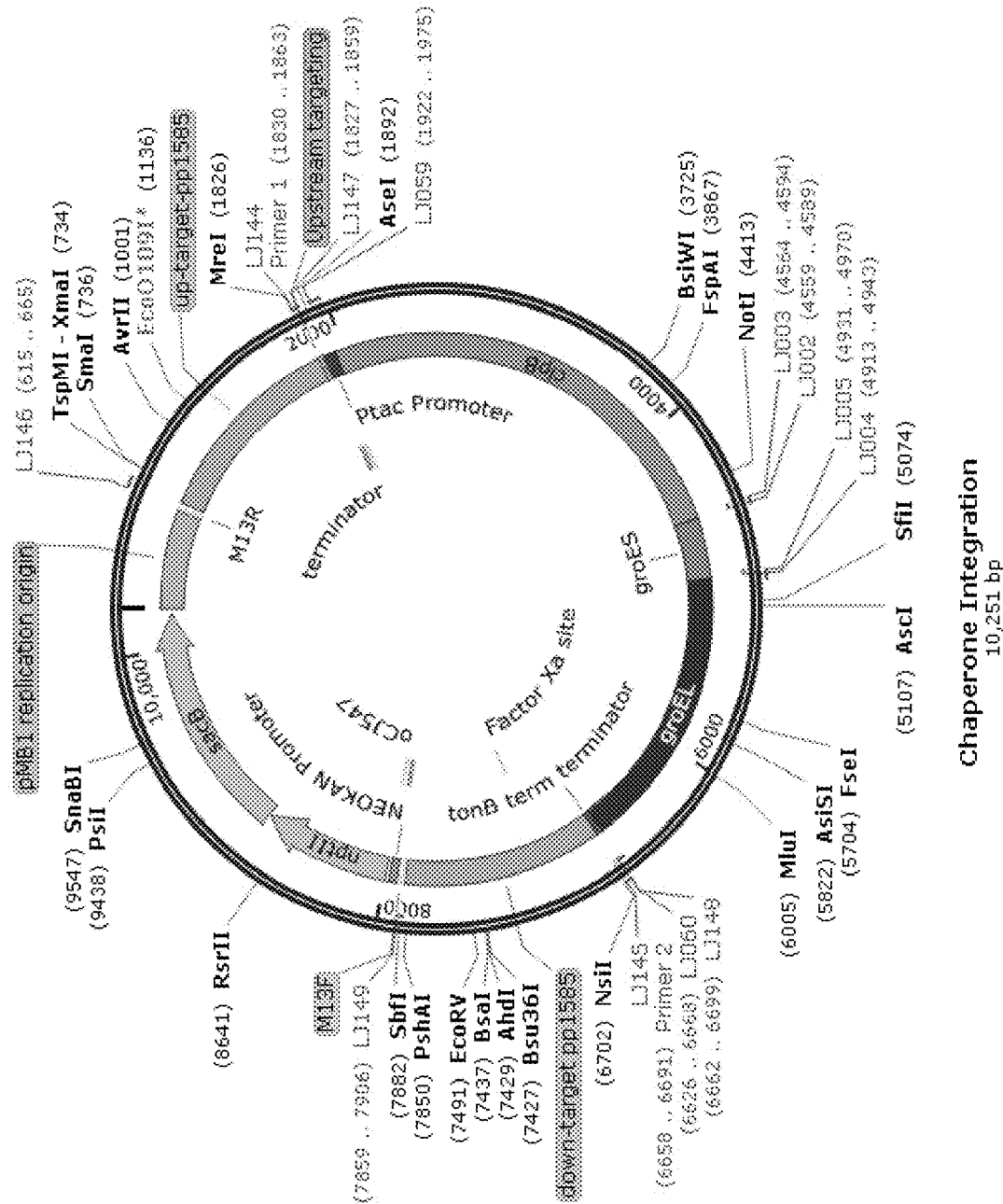
FIG. 5 is a map of the integrated plasmid pK18sB-PP_1584: Ptac-clpB-groES-groEL whose nucleotide sequence (SEQ ID NO: 7) is depicted in FIG. 4.

Disclosed herein are genes and modified microorganisms that can be used to overcome the acute chemical toxicity of TC wastewater streams. For example, the overexpression of chaperone genes such as clpB-groESL in the metabolically versatile bacterium *P. putida* allows the strain to be more tolerant to such toxic compounds and metabolize carbon found in waste streams. By overcoming a primary challenge in TC wastewater valorization, the potential for complete utilization of waste carbon present in TC wastewater streams to produce value-added chemicals and compounds of interest can be realized. Valorization of this waste carbon may provide an economic benefit to TC biorefineries.

Among TC conversion processes, fast pyrolysis (FP) and catalytic fast pyrolysis (CFP) are promising options for production of biofuels and aromatic chemicals. Pyrolysis relies on rapid heating of biomass in the absence of oxygen to generate either a bio-oil or vapor, both of which can be catalytically deoxygenated. Several pioneer and demonstration plants use pyrolysis, and research is being pursued to develop more robust catalysts and efficient processes to deoxygenate biomass-derived intermediates to fuels and aromatic compounds. Additionally, pyrolysis streams may also have potential for co-feeding into petroleum refineries. Given the oxygen content of biomass and the deoxygenation chemistry being pursued (which often uses dehydration), FP and CFP processes, like many processes that process organic chemicals, invariably generate wastewater containing un- or partially converted carbon that requires remediation via costly waste treatment processes.

Recent characterization of TC wastewater streams from FP and CFP show that the process configuration and conditions, biomass source, and catalyst impact the composition and carbon content of the resulting wastewater. Refractory C1-C3 compounds such as GA, acetate, and methanol along with partially deoxygenated aromatic compounds are prevalent, with total carbon content in some cases up to 350 g/L. Given the toxic nature of these compounds and their high concentrations in multiple pyrolysis wastewater streams, it is highly likely that anaerobic digestion (AD) units will not be able to tolerate these streams without considerable detoxification, supplementation with other biogenic carbon, and considerable dilution (>100-fold). Instead, most AD research focuses on applications to less toxic streams, such as municipal solid waste or food waste.

Most current approaches to waste utilization generally target the isolation of single substrates or narrow classes of compounds (e.g., levoglucosan) in streams that are extensively purified and detoxified. Using these separated, detoxified streams, downstream microbial conversion can be achieved. Separations and purification are often the most expensive steps in a bioprocess, and accordingly, being able to avoid detoxification and purification to narrow libraries of compounds would be ideal to combine the beneficial attributes of TC processing with microbial conversion.

Biocatalysts disclosed herein may be used to valorize the toxic, heterogeneous mixtures of organic compounds in pyrolysis wastewater to compounds of interest such as value-added co-products. To accomplish this task biologically without detoxification and fractionation requires microbes or designer communities engineered to exhibit unprecedented toxicity tolerance, very broad substrate specificity, and the ability to produce value-added compounds. A challenge to accomplish this objective is toxicity of wastewater streams which include compounds such as aldehydes, ketones, phenolics, and acids. These molecules often cause severe microbial toxicity via damage to biomolecules, membrane damage, disruption of metabolic circuits, creation of redox cofactor imbalances, and/or depletion of ATP generation. More broadly, organic-rich wastewater streams are produced from both biomass processing and organic chemical manufacturing, and microbial biotechnology solutions to valorize these streams are receiving more attention. To date, most solutions still rely on AD using a microbial consortium, which limits the product spectrum that can be targeted and sets an upper threshold on the stream toxicity, but the ability to use an engineered microbe or designer consortium with extremely high toxicity tolerance and substrate specificity allows the production of a range of valuable products.

Systems biology and high-throughput library screening may be used to identify genetic targets that enable in situ detoxification of multiple toxic compounds, and enzyme engineering, re-wiring metabolic circuits, and redox cofactor engineering can be used to further improve detoxification. In addition, membrane, efflux, transporter, and DNA repair machinery engineering have been identified as powerful targets to protect cells. Notably, engineering post-translational protein machineries of biocatalysts is a vital tool for enhancing tolerance of microorganisms. For instance, bacterial tolerance to high temperature and solvents may be achieved by engineering chaperones, or heat shock proteins (Hsp) that provide protein "quality control", including re-folding, ensuring correct functional confirmation, disaggregation of protein aggregates, protein trafficking, and degradation of misfolded or damaged proteins.

Chaperones execute their functions via allosteric machinery, energized by cycles of ATP binding and hydrolysis. Chaperones are typically categorized as Hsp10, Hsp20, Hsp40, Hsp60, Hsp70, Hsp90, and Hsp100, based on their molecular weights in kDa, and exhibit broad substrate specificity. For instance, the bacterial GroESL complex, consisting of the Hsp60 chaperonin, GroEL, and its Hsp10 co-chaperone, GroES, functions to refold numerous proteins. Like the GroESL complex, the Hsp70 chaperonin, DnaK, complexes with the co-chaperones Hsp40, DnaJ, and Hsp20, GrpE, to form DnaJKE, which is crucial for the survival of bacteria under stress conditions. The Hsp100 chaperone, including the bacterial ClpA, ClpB, and ClpX are referred to as unfoldases and disaggregases. ClpA and ClpX promote specific protein degradation via the ClpP protease, while ClpB disassembles protein aggregates and refolds them into functional proteins together with the DnaJKE and/or the GroESL system. In an embodiment, the above chaperones may be overexpressed in organisms of the present disclosure to increase tolerance to toxic compounds.

The soil bacterium *Pseudomonas putida* KT2440 was chosen as a model organism to overexpress chaperones, but other bacteria and microorganisms are suitable for use in the disclosed methods. Overexpression of the chaperone genes clpB, groES, and groEL (and others) enables *P. putida* KT2440 to overcome the acute toxicity of multiple TC wastewater streams from pilot-scale operations. The engineered, non-naturally occurring *P. putida* strains can metabolize a portion of the waste carbon at an industrially process-relevant substrate concentration as its sole source of carbon and energy. In an embodiment, the engineered, non-naturally occurring strains disclosed herein can be used for aerobic monoculture for TC wastewater valorization by overcoming substrate toxicity.

This disclosure provides the overexpression of the autologous chaperone genes clpB, groES, and groEL, which encode primary elements of stress defense, provides a solution to overcome the chemical stress of TC wastewater streams. The LJ015 strain described herein in exemplary embodiments, enables access to industrially-relevant levels of carbon in the four classes of TC wastewater streams tested. This represents a major step towards an industrially-relevant biological strategy to valorize TC wastewater without substantial previous detoxification. Specifically, this strain can enable production of high value products via metabolic engineering aimed at both expanding substrate utilization and improving and targeting product formation.

Conventional solutions to cleanup of organic-rich, highly-toxic wastewater streams from TC biorefineries, and more generally from organic chemical manufacturing, primarily use strategies such as catalytic hydrothermal gasification, which can produce methane and carbon dioxide. AD to produce methane is another commonly used strategy, but stream toxicity is a major barrier to its use, essentially precluding its utility for TC biorefineries. Given how little research has been done in this space, wastewater treatment has been identified as a major uncertainty in the development of TC processes. Designer biological systems that use aerobic catabolic pathways could potentially enable the production of higher-value compounds than methane.

In an embodiment, the increased tolerance of the non-naturally occurring strains disclosed herein toward a broader range of toxic compounds containing aldehyde, ketone, phenolic, and acid functional groups, as well as the combinatorial chemical toxicity found in TC wastewater streams is achieved by genetically engineering *P. putida* to create non-naturally occurring strains that overexpress the native *P. putida* GroESL-ClpB chaperone system. The TC wastewater compounds are often found in lignocellulosic hydrolysates and other industrial wastewater streams and are known to be quite toxic. Thus, the approach developed here could also be broadly utilized in different biorefinery scenarios as a strain engineering strategy to overcome substrate toxicity, which goes beyond the current applications of chaperones for improving tolerance of microbes toward end-product inhibition or temperature stress. Moreover, the GroESL-ClpB chaperone system may be further optimized by overexpressing partner chaperones such as hscB or novel candidate partner proteins identified in the global proteomics profile of the LJ014 strain. The expression level of the chaperones, appropriate to the stream toxicity, may be fine-tuned to increase the overall efficiency of this ATP utilizing system.

Protein damage is a key component of aldehyde toxicity. The extent of damage is closely related to the electrophilic activity (ω) and chemical structure of aldehydes. Short aliphatic aldehydes such as formaldehyde and acetaldehyde target neutrophilic lysine residues on proteins, and form carboxyl-methyl lysine (CML). Beyond the CML formation, the most toxic subclass of aldehyde, α-hydroxyaldehydes such as GA, cross-link proteins by targeting neutrophilic lysine residues and cysteine residues via the formation of Schiff-base and concurrent Amadori rearrangement, which leads to re-generation of the aldehyde carbonyl group after the first attack on a protein, forming a second covalent bond with a different protein. The remarkable ability of ClpB to rescue stress-damaged proteins via ATP-driven mechanical unfolding of aggregated proteins, suggest that the chaperone ClpB might be able to rescue the GA-mediated cross-linked proteins by breaking the cross-links in vivo.

Multi-omics analyses (Table 8) highlight additional engineering targets for enhanced *P. putida* tolerance to TC wastewater including the efflux pumps MexEF and OprN, the alcohol dehydrogenase PP_2476, and hypothetical protein PP_3770.

TABLE 8

Significantly upregulated genes in both GA and FPF-treated *P. putida* KT2440 cultures compared to control cultures.

| Gene | Annotation | N. $Log_2$ (GA)- N. $Log_2$ (untreated) | N. $Log_2$ (FPF-treated)- N. $Log_2$ (untreated) |
|---|---|---|---|
| PP_1395 | transcriptional regulator, AraC family | 2.66 | 3.41 |
| PP_1396 | hypothetical protein | 4.12 | 4.43 |
| PP_1397 | hypothetical protein | 3.07 | 2.94 |
| PP_2093 | response regulator receiver and ANTAR domain protein | 2.16 | 2.21 |
| PP_2213 | acyl-CoA ligase | 2.28 | 2.27 |
| PP_2425 | transcriptional regulator, AraC family | 5.67 | 4.96 |
| PP_2426 | D-isomer specific 2-hydroxyacid dehydrogenase family protein | 7.85 | 6.12 |
| PP_2427 | hypothetical protein | 3.07 | 2.02 |
| PP_2476 | alcohol dehydrogenase, zinc-containing | 3.56 | 2.19 |
| PP_2647 | major facilitator family transporter | 6.11 | 3.59 |
| PP_3425 | multidrug efflux RND membrane fusion protein MexE | 7.01 | 4.80 |
| PP_3426 | multidrug efflux RND transporter MexF | 6.51 | 4.11 |
| PP_3427 | multidrug efflux RND outer membrane protein OprN | 6.58 | 4.68 |
| PP_3519 | lipoprotein, putative | 4.31 | 2.31 |
| PP_3621 | isoquinoline 1-oxidoreductase, alpha subunit, putative | 2.48 | 3.78 |
| PP_3622 | isoquinoline 1-oxidoreductase, beta subunit, putative | 2.88 | 3.60 |
| PP_3623 | cytochrome c family protein | 2.58 | 3.41 |
| PP_3745 | glycolate oxidase, subunit GlcD | 3.77 | 3.66 |
| PP_3747 | glycolate oxidase, iron-sulfur subunit | 3.33 | 3.96 |
| PP_3748 | glcG protein | 2.08 | 2.07 |
| PP_3770 | hypothetical protein | 7.87 | 4.66 |
| PP_4087 | hypothetical protein | 3.22 | 2.25 |
| PP_4858 | hypothetical protein | 6.97 | 4.67 |
| PP_5287 | hypothetical protein | 2.35 | 2.33 |
| PP_5390 | hypothetical protein | 2.07 | 2.26 |

Overexpression of these genes show enhanced tolerance to aldehydes and FPF. These particular genes may be incorporated into the LJ015 strain to further enhance tolerance. Additionally, several functionally unknown genes that were upregulated in GA- or FPF-treated conditions may be added to increase bacterial tolerance and conversion of toxic substances (Table 8, Table 10). Accordingly, these multi-omics data are a rich source for identifying new genetic traits to further improve strain tolerance to different chemical functional groups.

TABLE 10

Gene ontologies enriched in differentially expressed proteins

| | KT2440(FPF-treated) vs KT2440(untreated) | LJ014 (untreated) vs KT2440 (untreated) | LJ014 (FPF-treated) vs KT2440 (FPF-treated) |
|---|---|---|---|
| Higher expression | Iron ion binding Gluconate dehydrogenase activity Benzoate 1,2-dioxygenase activity | No GO enrichment | Siderophore transport Receptor activity Iron ion binding |
| Lower expression | Oxidation-reduction process Oxidoreductase activity, Acting on CH—OH group of donors Flavin adenine dinucleotide binding Acetate-CoA ligase | No GO enrichment | No GO enrichment |

TABLE 10-continued

Gene ontologies enriched in differentially expressed proteins

| | KT2440(FPF-treated) vs KT2440(untreated) | LJ014 (untreated) vs KT2440 (untreated) | LJ014 (FPF-treated) vs KT2440 (FPF-treated) |
|---|---|---|---|
| | activity Acyl-CoA dehydrogenase activity Acetyl-CoA activity | | |

TABLE 10-continued

Gene ontologies enriched in differentially expressed proteins

| KT2440(FPF-treated) vs KT2440(untreated) | LJ014 (untreated) vs KT2440 (untreated) | LJ014 (FPF-treated) vs KT2440 (FPF-treated) |
|---|---|---|
| Acyltransferase activity | | |
| Metal ion transport | | |
| Sarcosine oxidase activity | | |

Microbial tolerance to chemical stressors is multigenic and complex. The clpB-groESL gene expression described herein triggers the recovery of proteins of the key stress response pathways including detoxification, transporters and efflux pumps, DNA repair, membrane integrity, and transcriptional regulators. Induction of such proteins suggest that toxicity goes beyond protein damage. For example, α-hydroxyaldehydes are known to impose direct DNA and RNA glycation, concurrent DNA mutation, DNA strand breaks, and cytotoxicity. The enhancements made to the LJ015 strain alleviate these toxic effects by increasing expression of nucleotide repair proteins including adenine glycosylase MutY and uracil-DNA glycosylase Ung. This suggests cross-talk between the ClpB-GroESL chaperones and DNA repair systems.

A two-pronged system against chemical toxicity, namely detoxification and cell protection, may provide enhanced strain robustness. Non-naturally occurring strains disclosed herein have metabolic routes to convert toxic compounds in TC wastewater streams, while protecting the cellular macromolecules via the damage-repair machineries of *P. putida*. In an embodiment, *P. putida* KT2440 can be engineered to efficiently metabolize GA, furfural, HMF, and levoglucosan. Other autologous and heterologous pathways in *P. putida* have also been identified for metabolism of acetone, acetaldehyde, formate, methanol, phenol and cresol. Stacking these pathways into LJ015 could enable utilization of nearly 100% of carbon present in the TC wastewater streams.

Several metabolic engineering strategies have been adopted to enhance mcl-PHAs production in *P. putida*, and these approaches may further improve mcl-PHA production in the LJ015 strain. Beyond mcl-PHA production, engineering the aromatic catabolic pathways in LJ015 could enable conversion of the aromatic carbons in the TC wastewater stream (e.g., which is rich in the ex-situ CFP stream) for the production of atom-efficient, high-value building blocks such as muconic acid. Given the chemical heterogeneity of TC wastewater streams, techno-economic analysis coupled with metabolic modeling will be useful for identifying products based on specific TC wastewater streams and aid in predicting which metabolic routes will require tailoring to optimize conversion.

In various embodiments, the chaperone polypeptides may be from microorganisms such as bacteria, yeast or fungi. Exemplary bacteria include species from the family Pseudonocardiaceae or species from the genera *Rhodococcus, Amycolatopsis, Acinetobacter, Pimelobacter, Gordonia, Pseudonocardia, Saccharomonospora, Corynebacterium, Actinopolyspora, Nocardia, Saccharopolyspora, Nocardioides,* or *Granulicoccus*. Though specific examples are provided herein, other examples of microbial chaperone polypeptides are within the scope of this disclosure.

Also presented are microorganisms engineered to express the chaperones disclosed herein and their use to detoxify waste streams or convert carbon-containing components such as those found in waste water to useful compounds. Bioconversion may be carried out be culturing such microorganisms with a material containing waste water or other carbon sources and allowing the microorganisms to enzymatically complete the conversion. Any microorganism capable of exhibiting increase tolerance to toxic compounds through the addition of enzymes disclosed herein may be suitable. Exemplary microorganisms include bacteria, such as those from the genus *Pseudomonas*. Specific examples include strains of *Pseudomonas putida*, such as *P. putida* KT2440.

Waste streams such as thermochemical waste water (supplemented with media or nutrients as needed) may be contacted with organisms at a concentration and a temperature for a time sufficient to achieve the desired amount of detoxification or carbon utilization. Suitable times range from a few hours to several days and may be selected to achieve a desired amount of conversion. Exemplary reaction times include 1, 2, 3, 4, 5, 6, 7, 8, 9, 10, 11, or 12 hours; and 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 days. In some embodiments, reaction times may be one or more weeks.

Methods of fractionating, isolating or purifying bioconversion products (or further upgraded products) include a variety of biochemical engineering unit operations. For example, the reaction mixture or cell culture lysate may be filtered to separate solids from products present in a liquid portion. Products may be further extracted from a solvent and/or purified using conventional methods. Exemplary methods for purification/isolation/separation of products include at least one of affinity chromatography, ion exchange chromatography, solvent extraction, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, and/or or reversed-phase HPLC.

Pyrolysis offers a straightforward approach for the deconstruction of plant cell wall polymers into pyrolysis oil or bio-oil, which may be fractionated and subsequently used in biological approaches to selectively upgrade some of the resulting fractions. Lignocellulose or lignin-containing materials may be subjected to pyrolysis processes to generate oils containing aromatic substrates. Exemplary lignocellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

The sequences disclosed herein provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library) and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning or assembling) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme or proteins disclosed herein. For example, a fragment can comprise the minimum nucleotides required to encode a functional chaperone or component thereof. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode the polypeptides that possess the enzymatic activities described herein or functional equivalents thereof. A functional equivalent includes fragments or variants of these that exhibit one or more of the enzymatic activities. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes or proteins through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Acinetobacter* (e.g., strains of *A. baylyi* such as ADP1), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium*, *Aspergillus* (e.g., *A. niger, A. nidulans, A. awamori*, or *A. aculeatus*), *Fusarium*, *Neurospora*, *Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Media may be supplemented with aromatic substrates, or components of thermochemical waste streams as needed.

The nucleic acid molecules described herein encode the enzymes with amino acid sequences such as those presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein or may include up to a certain integer number of amino acid alterations. Such protein or polypeptide variants retain enzymatic activity, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences set forth in the sequences provided herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Example 1

Strain, Media and Chemicals

*P. putida* strains used herein are listed in Table 1. Chemically competent NEB 5-alpha F'Iq *E. coli* (New England Biolabs, USA) was used for the plasmid manipulations. *E. coli* was grown in Luria-Bertani (LB) medium (Lennox) containing 10 g/L tryptone, 5 g/L yeast extract, and 5 g/L NaCl, in the presence of 50 μg/mL kanamycin. LB plates containing 50 μg/mL kanamycin were prepared by adding 15 g/L agar to LB media and used to select plasmid bearing *E. coli* and *P. putida* strains. *P. putida* strains were grown in modified M9 minimal medium (M9) containing 6.78 g/L $Na_2HPO_4$, 3.00 g/L $K_2HPO_4$, 0.50 g/L NaCl, 1.66 g/L $NH_4Cl$, 0.24 g/L $MgSO_4$, 0.01 g/L $CaCl_2$), and 0.002 g/L $FeSO_4$, supplemented with 3.60 g/L glucose and/or different concentrations of TC wastewater streams neutralized (pH 7) with NaOH. For analysis of mcl-PHA production, N-limiting M9 medium was prepared by substituting 0.24 g/L $NH_4Cl$ with 0.132 g/L of $(NH_4)_2SO_4$. All the chemicals used for the study were obtained from Sigma-Aldrich (St. Louis, Mo., USA). TC wastewater streams used for the study are listed in Table 2. FPF synthetic medium (FPF-syn) was prepared by adding the 32 most abundant compounds present in FPF at concentrations equal to those found in actual FPF (see Table 6). FPF synthetic-aldehyde, -ketones, -phenolics, and -acids media were prepared by adding subsets of those 32 compounds based on their functional groups.

TABLE 1

| Strain ID | Genotype | Strain Description |
|---|---|---|
| KT2440 | *P. putida* KT2440 | Wild-type *P. putida* KT2440 (ATCC 47054) |
| EM42 | *P. putida* KT2440 Δprophage1-4 Δflagellum ΔendA-1 ΔendA-2 ΔTn7 ΔhsdRMS ΔTn4652 | Genome reduced strain derived from *P. putida* KT2440 |
| LJ001 | KT2440 + pBTL-2 | KT2440 containing the empty control plasmid (pBTL-2) |
| LJ002 | KT2440 + pBTL-2-clpB | KT2440 containing plasmid pLJ001 for overexpression of groES |
| LJ003 | KT2440 + pBTL-2-groES | KT2440 containing plasmid pLJ002 of overexpression of groES |
| LJ004 | KT2440 + pBTL-2-groEL | KT2440 containing plasmid pLJ003 of overexpression of groEL |
| LJ005 | KT2440 + pBTL-2-groES-groEL | KT2440 containing plasmid pLJ004 of overexpression of groES and groEL |
| LJ006 | KT2440 + pBTL-2-clpB-groES-groEL | KT2440 containing plasmid pLJ005 of overexpression of groES, groEL, and clpB |
| LJ007 | KT2440 + pBTL-2-dnaJ | KT2440 containing plasmid pLJ006 of overexpression of dnaJ |
| LJ008 | KT2440 + pBTL-2-dnaK | KT2440 containing plasmid pLJ007 of overexpression of dnaK |
| LJ009 | KT2440 + pBTL-2-grpE | KT2440 containing plasmid pLJ008 of overexpression of grpE |
| LJ010 | KT2440 + pBTL-2-dnaJ-dnaK-grpE | KT2440 containing plasmid pLJ009 of overexpression of dnaJ, dnaK, and grpE |
| LJ011 | KT2440 + pBTL-2-dnaJ-dnaK-grpE-clpB | KT2440 containing plasmid pLJ010 of overexpression of dnaJ, dnaK, grpE, and clpB |
| LJ012 | KT2440 + pBTL-2-dnaJ-dnaK-grpE-groES-groEL | KT2440 containing plasmid pLJ011 of overexpression of dnaJ, dnaK, grpE, groES, and groEL |
| LJ013 | KT2440 + pBTL-2-dnaJ-dnaK-grpE-clpB-groES-groEL | KT2440 containing plasmid pLJ012 of overexpression of dnaJ, dnaK, grpE, clpB, groES, and groEL |
| LJ014 | KT2440 PP_1584:: Ptac:: clpB-groES-groEL | KT2440 with the clpB-groES-groEL chaperone expression cassette integrated within the intergenic region between PP_1584 and PP_1585 |
| LJ015 | EM42 PP_1584:: Ptac:: clpB-groES-groEL | EM42 with the clpB-groES-groEL chaperone expression cassette integrated within the intergenic region between PP_1584 and PP_1585 |

TABLE 2

| Process | Abbreviation | Derived from |
| --- | --- | --- |
| Fast pyrolysis | FP | Pine |
| Fast pyrolysis with fractionation | FPF | Pine: 5$^{th}$ fraction |
| in situ catalytic fast pyrolysis | in situ CFP | Pine |
| Ex situ catalytic fast pyrolysis | ex situ CFP | Pine: Davison circulating riser reactor with Ecat catalysis |

TABLE 6

Chemical composition of FPF

| | Compound | Concentration (g/L) | Concentration (M) | Weight % | Carbon weight (g/L) | Carbon weight % |
| --- | --- | --- | --- | --- | --- | --- |
| Acids | Acetic acid $^{a**}$ | 114.64 | 1.9091 | 33.81 | 45.86 | 31.05 |
| | Formic acid $^{a**}$ | 60.37 | 1.3117 | 17.81 | 15.75 | 10.67 |
| | Propionic acid $^{a**}$ | 3.4 | 0.0459 | 1.00 | 1.65 | 1.12 |
| | Butanoic acid $^{a}$ | 1.64 | 0.0186 | 0.48 | 0.89 | 0.61 |
| | Crotonic acid | 0.98 | 0.0114 | 0.29 | 0.55 | 0.37 |
| | Acrylic acid $^{a}$ | 7.5 | 0.1041 | 2.21 | 3.75 | 2.54 |
| | Pentanoic acid $^{a}$ | 0.11 | 0.0011 | 0.03 | 0.06 | 0.04 |
| | Itaconic acid $^{a}$ | 7.13 | 0.0548 | 2.10 | 3.29 | 2.23 |
| Aldehydes | Glycolaldehyde $^{a*}$ | 51.46 | 0.8570 | 15.18 | 20.58 | 13.94 |
| | Acetaldehyde $^{a**}$ | 4.36 | 0.0990 | 1.29 | 2.38 | 1.61 |
| | Furfural $^{a*}$ | 10.7 | 0.1114 | 3.16 | 6.69 | 4.53 |
| | Crotonaldehyde $^{a}$ | 4.38 | 0.0625 | 1.29 | 3.00 | 2.03 |
| | 5-Methylfurfural $^{a}$ | 1.05 | 0.0095 | 0.31 | 0.69 | 0.47 |
| | 5-(Hydroxymethyl)furfural $^{a*}$ | 0.54 | 0.0043 | 0.16 | 0.31 | 0.21 |
| | 2-Methyl-2-butenal $^{a}$ | 0.05 | 0.0006 | 0.01 | 0.04 | 0.02 |
| | 3-Furaldehyde $^{a}$ | 0.28 | 0.0029 | 0.08 | 0.18 | 0.12 |
| | Vanillin $^{a**}$ | 1.52 | 0.0100 | 0.45 | 0.96 | 0.65 |
| Ketones | Acetone $^{a}$ | 6.01 | 0.1035 | 1.77 | 3.73 | 2.52 |
| | Acetol $^{a*}$ | 6.89 | 0.0930 | 2.03 | 3.35 | 2.27 |
| | 2-Oxobutanol $^{a*}$ | 3.92 | 0.0445 | 1.16 | 2.14 | 1.45 |
| | Acetoin | 0.3 | 0.0034 | 0.09 | 0.16 | 0.11 |
| | Cyclopentenone $^{a*}$ | 4.08 | 0.0497 | 1.20 | 2.98 | 2.02 |
| | Cyclotene $^{a*}$ | 2.92 | 0.0260 | 0.86 | 1.88 | 1.27 |
| | 2-methylcyclopentenone $^{a*}$ | 1.38 | 0.0144 | 0.41 | 1.03 | 0.70 |
| | 1-Methyl-1-cyclopenten-3-one | 0.85 | 0.0088 | 0.25 | 0.64 | 0.43 |
| | 2,3-Dimethyl-1-cyclopenten-1-one | 0.43 | 0.0039 | 0.13 | 0.33 | 0.22 |
| | Methyl vinyl ketone | 0.09 | 0.0013 | 0.03 | 0.06 | 0.04 |
| | Butyrolactone $^{a}$ | 1.11 | 0.0129 | 0.33 | 0.62 | 0.42 |
| | Methylpropyl ketone | 0.67 | 0.0078 | 0.20 | 0.47 | 0.32 |
| | Cyclopentanone | 0.39 | 0.0046 | 0.12 | 0.28 | 0.19 |
| | 1,2-Cyclopentanedione | 0.2 | 0.0020 | 0.06 | 0.12 | 0.08 |
| | Maple lactone | 0.07 | 0.0006 | 0.02 | 0.04 | 0.03 |
| | 1,4-Cyclohexanedione | 0.15 | 0.0013 | 0.04 | 0.10 | 0.07 |
| | Biacetyl | 0.51 | 0.0059 | 0.15 | 0.28 | 0.19 |
| | Acetylpropionyl | 0.2 | 0.0020 | 0.06 | 0.12 | 0.08 |
| | 2-Acetylfuran | 0.35 | 0.0032 | 0.10 | 0.23 | 0.16 |
| | Maltol | 0.29 | 0.0023 | 0.09 | 0.17 | 0.11 |
| | 2(5H)-Furanone $^{a}$ | 24.72 | 0.2940 | 7.29 | 14.13 | 9.57 |
| | 3-Methyl-2(5H)-furanone | 0.95 | 0.0097 | 0.28 | 0.58 | 0.39 |
| | 4-Methyl-2(5H)-furanone | 0.33 | 0.0034 | 0.10 | 0.20 | 0.14 |
| | 5-Methyl-2(5H)-furanone | 0.56 | 0.0057 | 0.17 | 0.34 | 0.23 |
| Phenolics | Phenol $^{a}$ | 1.39 | 0.0148 | 0.41 | 1.06 | 0.72 |
| | Guaiacol $^{a}$ | 1.66 | 0.0134 | 0.49 | 1.12 | 0.76 |
| | Syringol $^{a}$ | 0.56 | 0.0036 | 0.17 | 0.35 | 0.24 |
| | o-Cresol $^{a}$ | 0.6 | 0.0055 | 0.18 | 0.47 | 0.32 |
| | m-Cresol $^{a}$ | 0.45 | 0.0042 | 0.13 | 0.35 | 0.24 |
| | p-Cresol $^{a}$ | 0.45 | 0.0042 | 0.13 | 0.35 | 0.24 |
| | Creosol $^{a}$ | 0.86 | 0.0062 | 0.25 | 0.60 | 0.40 |
| | 4-propylguaiacol | 0.03 | 0.0002 | 0.01 | 0.02 | 0.01 |
| | Catechol $^{a**}$ | 0.34 | 0.0031 | 0.10 | 0.22 | 0.15 |
| | 4-Ethylguaiacol | 0.29 | 0.0019 | 0.09 | 0.21 | 0.14 |
| | 4-Vinylguaiacol | 0.02 | 0.0001 | 0.01 | 0.01 | 0.01 |
| | 2,3-Xylenol | 0.02 | 0.0002 | 0.01 | 0.02 | 0.01 |

TABLE 6-continued

Chemical composition of FPF

| | Compound | Concentration (g/L) | Concentration (M) | Weight % | Carbon weight (g/L) | Carbon weight % |
|---|---|---|---|---|---|---|
| | 1,3,5-Xylenol | 0.01 | 0.0001 | 0.00 | 0.01 | 0.01 |
| | 2,6-Xylenol | 0.07 | 0.0006 | 0.02 | 0.06 | 0.04 |
| | 2,5-Xylenol $^a$ | 0.34 | 0.0028 | 0.10 | 0.27 | 0.18 |
| | Trans-isoeugenol | 0.05 | 0.0003 | 0.01 | 0.04 | 0.02 |
| | Eugenol | 0.18 | 0.0011 | 0.05 | 0.13 | 0.09 |
| | 2,5-Dimethoxytetrahydrofuran | 0.11 | 0.0008 | 0.03 | 0.06 | 0.04 |
| | 2-Ethylphenol | 0.03 | 0.0002 | 0.01 | 0.02 | 0.02 |
| | 2,3,5-Trimethylphenol | 0.06 | 0.0004 | 0.02 | 0.05 | 0.03 |
| | 2,3,4-Trihydroxybenzoic acid | 0.14 | 0.0008 | 0.04 | 0.07 | 0.05 |
| | 3,4,5-Trihydroxybenzoic acid | 0.18 | 0.0011 | 0.05 | 0.09 | 0.06 |
| | Apocynin | 0.02 | 0.0001 | 0.01 | 0.01 | 0.01 |
| Sugars | Levoglucosan | 3.68 | 0.0202 | 1.09 | 1.46 | 0.99 |
| Alcohol | 1-Propanol | 0.04 | 0.0007 | 0.01 | 0.02 | 0.02 |

For the compounds listed in Table 6, $^a$ denotes compounds that are included in the synthetic medium; and ** denotes compounds that can be completely metabolized by *P. putida* KT2440; and * denotes compounds that can be partially metabolized by *P. putida* KT2440. As depicted in Table 6, weight % was calculated based on the ratio of weight of particular compound and total weight of compounds. As depicted in Table 6, carbon % was calculated based on the ratio of carbon weight of particular compound and total carbon weight of compounds.

Table 7 depicts the $EC_{50}$ value of the most abundant compounds found in the thermochemical wastewater streams on naturally occurring *P. putida* KT2440.

TABLE 7

| Category | Compound | $EC_{50}$ (mM) | SEM |
|---|---|---|---|
| Aldehydes | Glycolaldehyde | 2.14 | 0.42 |
| | Acetaldehyde | 16.19 | 1.81 |
| | Furfural | 20.97 | 3.98 |
| | Crotonaldehyde | 17.37 | 2.81 |
| | 5-methylfufaral | 14.96 | 1.02 |
| | 5-HMF | 14.33 | 1.39 |
| | 3-Furancarboxaldehyde | 13.90 | 2.99 |
| | Vanillin | 6.34 | 0.04 |
| | Glyoxal | 3.50 | 0.28 |
| | Formaldehyde | 2.07 | 0.19 |
| Ketones | Acetone | 39.34 | 0.01 |
| | Acetol | 12.42 | 1.16 |
| | 2-Oxobutanol | 27.75 | 0.61 |
| | Methylolacetone | 28.75 | 0.31 |
| | Adipic ketone | 9.80 | 1.24 |
| | 2-Butenolide | 7.77 | 1.11 |
| | 2-Methyl-butenolide | 5.02 | 0.52 |
| Phenolics | Phenol | 9.24 | 0.15 |
| | Guaiacol | 13.27 | 2.11 |
| | Syringol | 4.21 | 0.57 |
| | o-Cresol | 3.12 | 0.01 |
| | m-Cresol | 3.46 | 0.47 |
| | p-Cresol | 2.25 | 0.44 |
| | Catechol | 42.41 | 6.47 |
| | 2,5-Xylenol | 2.52 | 0.12 |

TABLE 7-continued

| Category | Compound | $EC_{50}$ (mM) | SEM |
|---|---|---|---|
| Acids | Acetic acid | 64.06 | 5.19 |
| | Formic acid | 258.41 | 15.19 |
| | Propionic acid | 22.44 | 1.33 |
| | Butanoic acid | 35.25 | 3.03 |
| | Acrylic acid | 11.68 | 0.46 |
| | Itaconic acid | 89.40 | 16.33 |

Example 2

Plasmid Construction

Figure 21:
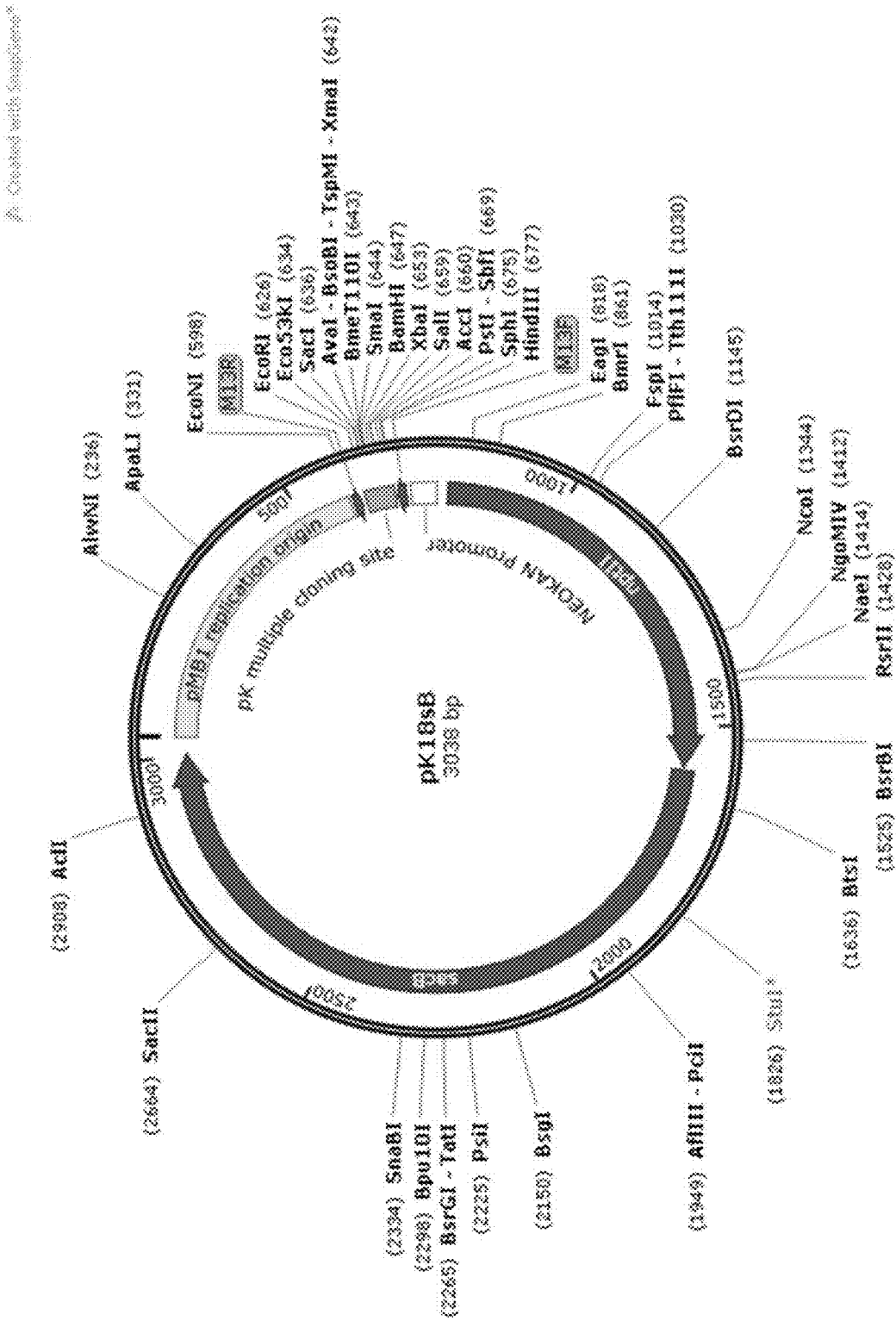
FIG. 21 depicts a plasmid map of the pK18sB vector, a smaller derivative of sacB-based genome integration vector pK18mobsacB. This plasmid is unable to replicate in *P. putida* and contains kanamycin antibiotic resistance gene to select for integration of the plasmid into the genome and sacB to counter select for recombination of the plasmid out of the genome.

Amplicons were obtained from *P. putida* KT2440 genomic DNA by performing polymerase chain reactions (PCR) with primers (see Table 3) synthesized by Integrated DNA Technologies (IDT) and Phusion High-Fidelity PCR Master Mix with HF Buffer (New England Biolabs, USA). Plasmids were constructed using NEBuilder HiFi DNA Assembly (New England Biolabs) according to the manufacturer's instructions. The vector, pBLT-2 (Addgene plasmid #22806) was used for plasmid-based overexpression of genes. A derivative of the plasmid pK18mobsacB (ATCC 87097), was constructed to exclude the mobilization factor and other extraneous DNA and named pK18sB (see FIG. 21), was used for construction of the plasmid for genome integration of the chaperone genes. The nucleotide sequence of the synthetic fragment incorporated into PK18sB is SEQ ID NO: 8. Plasmids were transformed into NEB 5-alpha F'Ig *E. coli* according to the manufacturer's instructions. Transformants were selected on LB (Lennox) plate supplemented with 50 μg/mL kanamycin grown at 37° C. Correct assembly was confirmed by restriction enzymes digestion and the sequences of all plasmid inserts were confirmed by Sanger sequencing (GENEWIZ, Inc., USA). Further descriptions about specific plasmid constructions can be found in Table 5.

TABLE 3

| Primer | Sequence [5'-3'] |
|---|---|
| LJ001 | GGAATTGTGAGCGGATAACAATTTCACACTTCCGACCTGCCCTTTAAAGGAAGGTACAC |
| LJ002 | AATTGTGGTTTTCATAGCCCCGCAAACGCGGGG |
| LJ003 | CGCGTTTGCGGGGCTATGAAAACCACAATTTGG |
| LJ006 | CGCTGGAGTCTGAGGCTCGTCCTGAATGATTTTTGATGGTGCAGGGGG |
| LJ018 | TGAGGCTCGTCCTGAATGATAGCCCCGCAAACGCGGGG |
| LJ020 | GCGGATAACAATTTCACACTGCGGCCGCATGAAAACCACAATTTGG |
| LJ021 | TGAGGCTCGTCCTGAATGATAAACTTTGGAGTAACGGG |
| LJ022 | GCGGATAACAATTTCACACTGCGGCCGCTACTCCAAAGTTTTCAAGGATTAAACG |
| LJ050 | GGAATTGTGAGCGGATAACAATTTCACACTCTACCAAATTCAAGTTTCGGGAGAG |
| LJ051 | CGCTGGAGTCTGAGGCTCGTCCTGAATGATCGGCCGACAACATGCAGG |
| LJ065 | GCGGATAACAATTTCACACTAATTGCGCAGGAGAGACC |
| LJ066 | TGAGGCTCGTCCTGAATGATCCGAAGGATTTCAAGCCTTTTC |
| LJ067 | GCGGATAACAATTTCACACTCAACAAGGTGCAAATGAC |
| LJ068 | TGAGGCTCGTCCTGAATGATCTGTTCCTTGTCAGAGATCG |
| LJ069 | CCGAAACTTGCTGTTCCTTGTCAGAGATCG |
| LJ070 | CAAGGAACAGCAAGTTTCGGGAGAGTTAACAT |
| LJ071 | CTGCGCAATTCATGCAGGGATTACTGCTTG |
| LJ072 | TCCCTGCATGAATTGCGCAGGAGAGACC |
| LJ073 | GCAGGTCGGACCGAAGGATTTCAAGCCTTTTC |
| LJ074 | AATCCTTCGGTCCGACCTGCCCTTTAAAGGAAGGTACAC |
| LJ075 | TGGTTTTCATCCGAAGGATTTCAAGCCTTTTC |
| LJ076 | AATCCTTCGGATGAAAACCACAATTTGG |
| LJ059 | TGTGAGCGGATAACAATTTCACACTTCCGACCTGCCCTTTAAAGGAAGGTACAC |
| LJ060 | GCCTCCGGTCGGAGGCTTTTGACTATTTTGATGGTGCAGGGGG |
| LJ144 | GCGGGAGATCGACGCAAAAAACCGCACCCAGGTG |
| LJ145 | GAAGATTTACGCAACAGTCAAAAGCCTCCGGTCG |
| LJ146 | GACATGATTACGAATTCGAGCTCGGTACCCTCGAGCCAGACCTACCCAGCG |
| LJ147 | TGGGTGCGGTTTTTTGCGTCGATCTCCCGCCGG |
| LJ148 | CGGAGGCTTTTGACTGTTGCGTAAATCTTCCCCAAAAT |
| LJ149 | CGGCCAGTGCCAAGCTTGCATGCCTGCAGGGCCGACCAGCTTCGACAG |
| LJ154 | CGCGGTATCCGCAACAACAA |
| LJ155 | ACGCATCGTTCATCAGTGCCT |
| CJ382 | AATTAACAGTTAACAAATAATCAGACCCCGTAGAAAAGATCAAAGGATCTTC |
| CJ384 | ATGATTGAACAAGATGGATTGCACGCAGG |
| CJ385 | AACTTTTTGATGTTCATCGTCGCTCAGAAGAACTCGTCAAGAAGGCGATAGAAG |
| CJ386 | TTCTGAGCGACGATGAACATCAAAAAGTTTGCAAAACAAGCAACAGTATTAACC |
| CJ387 | TACGGGGTCTGATTATTTGTTAACTGTTAATTGTCCTTGTTCAAGGATGCTGTC |
| CJ402 | GGCGTTTTTCCATAGGCTCCGC |

TABLE 5

| Plasmid | Purpose | Construction detail |
|---|---|---|
| pK18sB | Integration of genes into P. putida genome | From pK18mobsacB (GenBank: FJ437239.1), the pMB1 origin of replication was amplified with with oCJ382/oCJ402 (595 bp), the nptII kanamycin resistance gene was amplified with oCJ384/oCJ385 (795 bp), and the sacB levan sucrose gene was amplified with oCJ386/oCJ387 (1,422 bp), and these products were assembled with a double-stranded DNA fragment synthesized by IDT containing the pK multiple cloning site and M13 F and M13 R primer binding sites. |
| pLJ001 | Overexpressing clpB | A DNA fragment containing the clpB gene, including 30 base pairs upstream and 20 base pairs downstream, was amplified from P. putida KT2440 genomic DNA with primers oLJ001 (Fwd) and oLJ018 (Rev). This product was assembled into pBLT-2 digested with XbaI and EcoRV. |
| pLJ002 | Overexpressing groES | A DNA fragment containing the groES gene, including 30 base pairs upstream and 20 base pairs downstream, was amplified from P. putida KT2440 genomic DNA with primers oLJ020 (Fwd) and oLJ021 (Rev). This product was assembled into pBLT-2 digested with XbaI and EcoRV. |

TABLE 5-continued

| Plasmid | Purpose | Construction detail |
|---|---|---|
| pLJ003 | Overexpressing groEL | A DNA fragment containing the groEL gene, including 30 base pairs upstream and 20 base pairs downstream, was amplified from *P. putida* KT2440 genomic DNA with primers oLJ022 (Fwd) and oLJ006 (Rev). This product was assembled into pBLT-2 digested with XbaI and EcoRV. |
| pLJ004 | Overexpressing groES and groEL | A DNA fragment containing the groES and groEL genes, including 30 base pairs upstream and 20 base pairs downstream, was amplified from *P. putida* KT2440 genomic DNA with primers oLJ020 (Fwd) and oLJ006 (Rev). This product was assembled into pBLT-2 digested with XbaI and EcoRV. |
| pLJ005 | Overexpressing clpB, groES and groEL | DNA fragments containing the clpB and groES-groEL genes, both with and 30 base pairs upstream and 20 base pairs downstream, were amplified from *P. putida* KT2440 genomic DNA with primers oLJ001 (Fwd) and oLJ002 (Rev), and oLJ003 (Fwd) and oLJ006, respectively. These products were assembled into pBLT-2 digested with XbaI and EcoRV. |
| pLJ006 | Overexpressing dnaJ | A DNA fragment containing the dna' gene, including 30 base pairs upstream and 20 base pairs downstream, was amplified from *P. putida* KT2440 genomic DNA with primers oLJ067 (Fwd) and oLJ068. This product was assembled into pBLT-2 digested with XbaI and EcoRV. |
| pLJ007 | Overexpressing dnaK | A DNA fragment containing the dnaK gene, including 30 base pairs upstream and 20 base pairs downstream, was amplified from *P. putida* KT2440 genomic DNA with primers oLJ050 (Fwd) and oLJ051. This product was assembled into pBLT-2 digested with XbaI and EcoRV. |
| pLJ008 | Overexpressing grpE | A DNA fragment containing the grpE gene and 30 base pairs upstream and 20 base pairs downstream were amplified from *P. putida* KT2440 genomic DNA with primers oLJ065 (Fwd) and oLJ066. This product was assembled into pBLT-2 digested with XbaI and EcoRV. |
| pLJ009 | Overexpressing dnaJ, dnaK, and grpE | DNA fragments containing the dnaJ, dnaK, and grpE genes, all with and 30 base pairs upstream and 20 base pairs downstream, were amplified from *P. putida* KT2440 genomic DNA with primers oLJ067 (Fwd) and oLJ069 (Rev), oLJ070 (Fwd) and oLJ071 (Rev), and oLJ072 (Fwd) and oLJ066 (Rev), respectively. These products were assembled into pBLT-2 digested with XbaI and EcoRV. |
| pLJ010 | Overexpressing dnaJ, dnaK, grepE and clpB | A DNA fragment containing the clpB gene, including 30 base pairs upstream and 20 base pairs downstream, was amplified from *P. putida* KT2440 genomic DNA with primers oLJ074 (Fwd) and oLJ018 (Rev) and a fragment containing the dnaJ, dnaK, and grpE genes was amplified with primers oLJ067 (Fwd) and oLJ073 (Rev) using pLJ009 as a template. These products were assembled into pBLT-2 digested with XbaI and EcoRV. |
| pLJ011 | Overexpressing dnaJ, dnaK, grepE, groES and groEL | A DNA fragment containing the dnaJ, dnaK, and grpE genes was amplified using pLJ009 as a template with primers oLJ067 (Fwd) and oLJ075 (Rev) and a DNA fragment containing the groES and groEL genes, including 30 base pairs upstream and 20 base pairs downstream, was amplified with primers oLJ076 (Fwd) and oLJ006 (Rev) from *P. putida* KT2440 genomic DNA. These products were assembled into pBLT-2 digested with XbaI and EcoRV. |
| pLJ012 | Overexpressing dnaJ, dnaK, grepE, clpB, groES, and groEL | A DNA fragment containing the dnaJ, dnaK, and grpE genes was amplified using pLJ009 as a template with primers oLJ067 (Fwd) and oLJ073 (Rev) and a fragment contain the clpB, groES, and groEL genes was amplified with primers oLJ074 (Fwd) and oLJ006 (Rev) using pLJ005 as a template. These products were assembled into pBLT-2 digested with XbaI and EcoRV. |

TABLE 5-continued

| Plasmid | Purpose | Construction detail |
|---|---|---|
| pLJ013 | To integrate the tac promoter upstream of clpB-groES-groEL and used as a template in construction of pCJ014 | A DNA fragment containing the clpB, groES, and groEL genes was amplified using pLJ005 as a template with primers oLJ059 (Fwd) and oLJ060 (Rev), and assembled These products were assembled into pMFL160 digested with XbaI and SpeI.[11] |
| pLJ014 | Genome integration of overexpressing cassette of clpB, groES and groEL | The $T_{SoxR}$-Ptac:: clpB-groES-groEL-$T_{tonB}$ gene cassette was amplified with primers oLJ144 (Fwd) and oLJ145 (Rev) using pLJ013 as a temple. The 5' homology region was amplified from P. putida KT2440 genomic DNA with primers oLJ146 (Fwd), and oLJ147 (Rev), and 3' homology region was amplified with oLJ148 (Fwd) and oLJ149 (Rev). These products were assembled into pK18sB digested with SmaI and SalI. |

Example 3

Strain Construction

For plasmid-based gene expression, P. putida KT2440 was transformed by electroporation and selected on LB plates containing 50 µg/mL kanamycin.

Genomic integration of the tac promoter-driven chaperone genes, (clpB, groES, and groEL) in P. putida KT2440 (LJ014) and P. putida EM42 (LJ015) was accomplished using the antibiotic-sacB system of selection and counter-selection. A detailed description of the method, with modifications for P. putida KT2440, can be found in Johnson and Beckham (Metab. Eng., 2015, 28, 240-247). Following sucrose selection, single colonies were subjected to colony PCR with primers oLJ154 (Fwd) and oLJ155 (Rev) to identify those with genome integration of the chaperone genes.

Example 4

Growth Assay and Fermentation Analysis

Toxicity of the TC wastewater streams and toxic compounds present in FPS were evaluated in microplate growth assays performed in a Bioscreen C MBR analyzer (Growth Curves US, Piscataway, N.J.). Pre-cultures of the strains were prepared by inoculating 25 mL M9 medium supplemented with 20 mM glucose in a 125 mL baffled flask to an $OD_{600}$ of 0.05-0.1 and incubating shaking at 225 rpm, 30° C. At mid log phase ($OD_{600}$ 0.5-1.0), cells were harvested by centrifugation at 13,000 rpm, and the cell pellets were washed twice and resuspended in M9 medium without a carbon source. These resuspended cells were used to inoculate microplate wells containing 200 µL of M9 medium supplemented with 20 mM glucose and various concentrations of TC wastewater streams or their components to $OD_{600}$ 0.1. Microplates were then incubated at 30° C. with maximum shaking and growth was measured by reading the absorbance ($OD_{420-580}$) every 30 minutes. Growth rates were calculated according to the growth curve equation.

Figure 8:
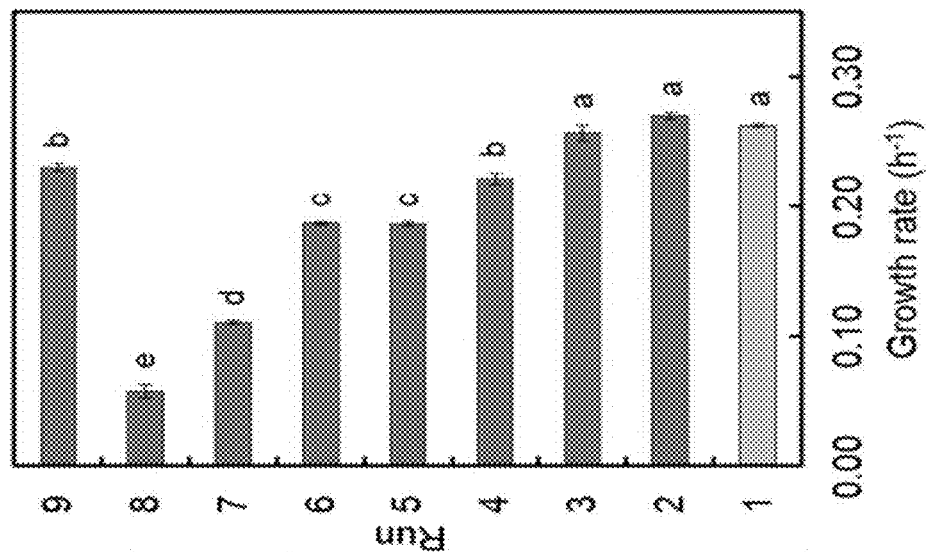
FIG. 8 depicts combinational inhibitory effects of different functional group compounds found in FPF on *P. putida* KT2440. $FPF_{SYN\_Ald}$: a synthetic medium of aldehydes, $FPF_{SYN\_Ket}$: a synthetic medium of ketones, $FPF_{SYN\_phe}$: a synthetic medium of phenols, and $FPF_{SYN\_Ace}$: a synthetic medium of acids fraction of FPF. Results are expressed as means±SEM (n=3). Bars labeled with different letters indicate statistical significance of different run (p<0.05; one-way ANOVA followed by Tukey's post hoc honest significance difference test).

For combinational inhibition assay analyses of the functional groups present in FPF, the following method was used. A three-level partial factorial growth experiment was performed using synthetic medium containing combinations of the most abundant compounds present in FPF based on their functional groups, including FPF-aldehyde, FPF-ketone, FPF-acids, and FPF-phenolics. Level 1 contained 0% (v/v), level 2 contained 0.02% (v/v), and level 3 contained 0.03% (v/v). As depicted in FIG. 8, nine interactions were tested according to Taguchi Orthogonal "L" Array design metrics. Two hundred µL of M9 medium-containing 20 mM glucose supplemented with various concentrations of FPF components was added to the wells of a Bioscreen C microplate, P. putida KT2440 cells were added to reach an initial cell density of $OD_{600}$=0.1, and the plate was incubated at 30° C. with medium shaking. The $OD_{420-580}$ was monitored using a Bioscreen C MBR analyzer (Growth Curves US, Piscataway, N.J.) every 30 minutes to generate growth curves. Growth curves were performed in triplicate and the average growth rate was obtained. The data were further subjected to partial least square regression analysis (PLS) with XLSTAT software to obtain the variable important parameter (VIP) of each component.

To assess the growth and carbon utilization of the strains in FPF, shake flask experiments were performed using 125 mL baffled flasks containing 50 mL modified M9 media supplemented with 1% (v/v) FPF (pH 7) and inoculated to $OD_{600}$ 0.2 with cells prepared as above but resuspended in M9 medium containing 1% (v/v) FPF. Cultures were incubated with shaking at 225 rpm, 30° C. 2 mL samples were collected periodically and subjected to HPLC analysis, total carbon analysis, and $OD_{600}$ growth measurement using a Beckman DU640 spectrophotometer (Beckman Coulter, Brea Calif.). The dry cell weight (DCW) of the cultures was calculated based on the $OD_{600}$ to DCW conversion equation [CDW (g/L)=0.5746 ($OD_{600}$ of sample)].

Example 5

HPLC and Total Carbon Analyses

Concentrations of acetate, glycolaldehyde, furfural, HMF, and glycolate were measured using high performance liquid chromatography (HPLC) by injecting 6 µL of 0.2-µm filter-sterilized culture supernatant onto an Agilent1100 series system (Agilent USA, Santa Clara, Calif.) equipped with a Phenomenex Rezex RFQ-Fast Fruit H+ column (Phenomenex, Torrance, Calif.) and cation H+ guard cartridge (Bio-Rad Laboratories, Hercules, Calif.) at 85° C. A mobile phase of 0.1N sulfuric acid was used at a flow rate of 1.0 mL/min. Refractive index and diode array detectors were used for compound detection. Compounds were identified by relating the retention times and spectral profiles with standard HPLC grade pure compounds (Sigma Aldrich, St. Louis, Mo., USA) and the concentration of each compound was calculated based on a calibration curves generated using pure compounds.

The total carbon of the samples was determined using a LECO TruSpec CHN module (LECO Corporation, Saint Joseph, Mich.). The sample (nominal weight of 0.1 g, encapsulated in a tin foil capsule with $Al_2O_3$) was placed in the sample loading head, sealed, and purged of any atmospheric gases. The sample was dropped into a furnace dosed with pure $O_2$ gas (99.995%) at 950° C. for combustion. The combustion products passed through the afterburner furnace (850° C.), where they succumbed to further oxidation and particulate removal. The resulting gaseous products were sent through anhydrone to remove moisture, and on to a $CO_2$ infrared detector to determine carbon content.

Example 6

Quantification of Mcl-PHA Production from FPF Carbon

To quantify mcl-PHAs as a percent of the dry cell weight in cultures growth in media containing FPF, shake-flask experiments were performed in N-limiting media as described above. mcl-PHA quantification was conducted as follows: 10-30 mg of cells were added to a glass vial and derivatized by adding about 1 mL of $BF_3$/MeOH containing 200 µL of benzoic acid dissolved in dichloromethane (10 mg/mL) as an internal surrogate to track derivatization. The vials were sealed, shaken, placed in a heating block at 80° C. overnight, then allowed to cool to room temperature. The samples were moved into a 10 mL volumetric flask and the vial residual was rinsed twice with DCM before filling the flask to 10 mL total with additional DCM. The 10 mL solution was transferred to a PTFE capped vial and about 3 mL of water was added to form a bi-phase and wash out residual $BF_3$ to the aqueous layer. The DCM layer (about 2 mL) was then transferred into another vial containing a small amount of $Na_2SO_4$ and $Na_2CO_3$ to dry and neutralize any remaining $BF_3$. The dried and neutralized solutions were syringe filtered (0.2 µm PTFE) into fresh vials for analysis. To track recovery of PHAs during sample derivatization and analysis, triplicate biomass samples of P. putida KT2440 were processed in parallel. Recovery yields during sample workup were calculated based on a cell dry weight PHA content of 24% determined by bulk sample solvent extraction.

Hydroxyacid methyl esters were identified and the distribution quantified by gas chromatography mass spectroscopy (GC-MS) using an Agilent 6890N GC equipped with a 5973 MSD (Agilent Technologies). Agilent MSD Productivity Chemstation G1701 software version D.00.00 was used to collect and quantitate analytes. 8-Hydroxyoctanoic acid, 10-hydroxydecanoic acid, 12-hydroxydodecanoic acid, and 14-hydroxytetradecanoic acids were obtained from Sigma Aldrich (98+% purity, Sigma Aldrich, St. Louis, Mo., USA), methylated as per the method used for the samples, and used to determine the GC-MS instrument response. Samples were injected at a volume of 1 µL onto a Stabilwax-DA column (30 m×0.25-mm id, 0.25-µm film) in splitless mode, with helium at 1 mL/min constant flow used as the carrier gas. The GC/MS method consisted of a front inlet temperature of 250° C., and an auxiliary transfer line temperature of 260° C. The separation used had a starting temperature of 225° C. and this was held for 2 minutes, then ramped at 15° C./min to a temperature of 250° C. and held for 5.7 minutes for a total run time of 27 minutes. Sample total ion counts were collected on the mass spectrometer at scan range from 30 to 450 m/z. Calibration curves where made by diluting the derivatized standards between a concentration of 5-175 µg/L. A minimum of six calibration levels was used resulting in an $r^2$ coefficient of 0.995 or better for each analyte and a check calibration standard (CCS) was analyzed every ten samples to insure the integrity of the initial calibration. An internal standard of 1,2-diphenylbenzene (99.9+% purity, AccuStandard, New Haven, Conn.) was added to all standards and samples at a concentration of 40 ug/L to adjust for any detector response shift.

Example 7

Microscopic Observation of P. putida.

Microscopic observation of mcl-PHAs in P. putida by epifluorescence was performed by removing 1 mL from FPF-containing shake flask cultures after 48 hours. The cells were pelleted by centrifugation at 13,000 rpm for 1 minute, washed twice with 1× phosphate buffered saline (PBS), resuspended in 1 mL PBS containing 10 µg/mL Nile Red (Molecular probes, Invitrogen Cooperation, USA), and incubated at room temperature in the dark for 30 minutes. The cells were pelleted again, washed with 1×PBS, and resuspended in 1 mL PBS. 5 µL of resuspended cells were mixed with 5 µL of 1% (w/v) low-melting-temperature agarose to immobilize the cells, which were then placed on a microscopic slide with coverslip. Nile Red fluorescence was observed with band-pass filtering between 560-590 nm using a Nikon Eclipse 80i microscope (Nikon Corp., Japan).

Example 8

Flow Cytometry

Live and dead cell counts were determined using the LIVE/DEAD™ BacLight™ Bacterial Viability Kit (ThermoFisher Scientific, USA) according to the manufacturer's instructions. Briefly, 1 mL samples were collected periodically, and culture supernatant was discarded after centrifugation at 13,000 rpm for 1 minute. Cell pellets were washed twice with 0.85% (w/v) NaCl, and resuspended in 1 mL 0.85% (w/v) NaCl solution for staining. 1.5 µL each of component A (SYTO 9) and component B (Propidium Iodide) was added to the samples and incubated at room temperature in the dark for 15 minutes. Samples were centrifuged at 13,000 rpm for 1 minute, and the supernatant was discarded. Cell pellets were washed with 0.85% (w/v) NaCl solution and resuspended in BD FACSFlow™ sheath fluid (BD Biosciences, USA) for analysis. Live and dead cell counts were monitored using a BD FACSAria™ (BD Biosciences, USA) instrument equipped with BD FACSDiva data acquisition and analytical software. The 488 nm laser coupled with B530-30A (530 nm) and B610-20A (610 nm) detection channels were used to sort the green (live) and red (dead) fluorescent cells, respectively. For each sample 30,000 events were recorded to generate scatter plots of B530-30A and B610-20A, which were used to determine the number of live and dead cells based on live and dead population regions assigned based on live and dead controls. For monitoring GFP protein fluorescence, samples were excited at 488 nm and detected at 530 nm and 20,000 events were recorded to generate each histogram.

Example 9

Statistical Analysis

All experiments were performed in triplicate or greater as indicated. Results are expressed as the mean value and error bars represent the standard error of the mean (SEM). For a pair-wise comparison of the differences between the sample averages of two groups, a one-tailed Student's t-test without known deviations was used. A one-way analysis of variance (ANOVA) followed by Tukey's post hoc honest significance difference test was used for several comparisons. Data analysis was performed using KaleidaGraph statistical program (Synergy Software, PA, USA). The Partial Least Square (PLS) regression modeling of multivariate data were performed with XLSTAT software (Addinsoft, USA). Fisher's Exact statistical test was performed with differentially expressed gene and protein datasets to identify enriched GO-terms compared to GO-terms of the entire *Pseudomonas putida* KT2440 genome determined by the standard workflow of Blast2GO 4.1.

Example 10

Baseline Toxicity of Waste Streams to *P. putida*

Figure 6:
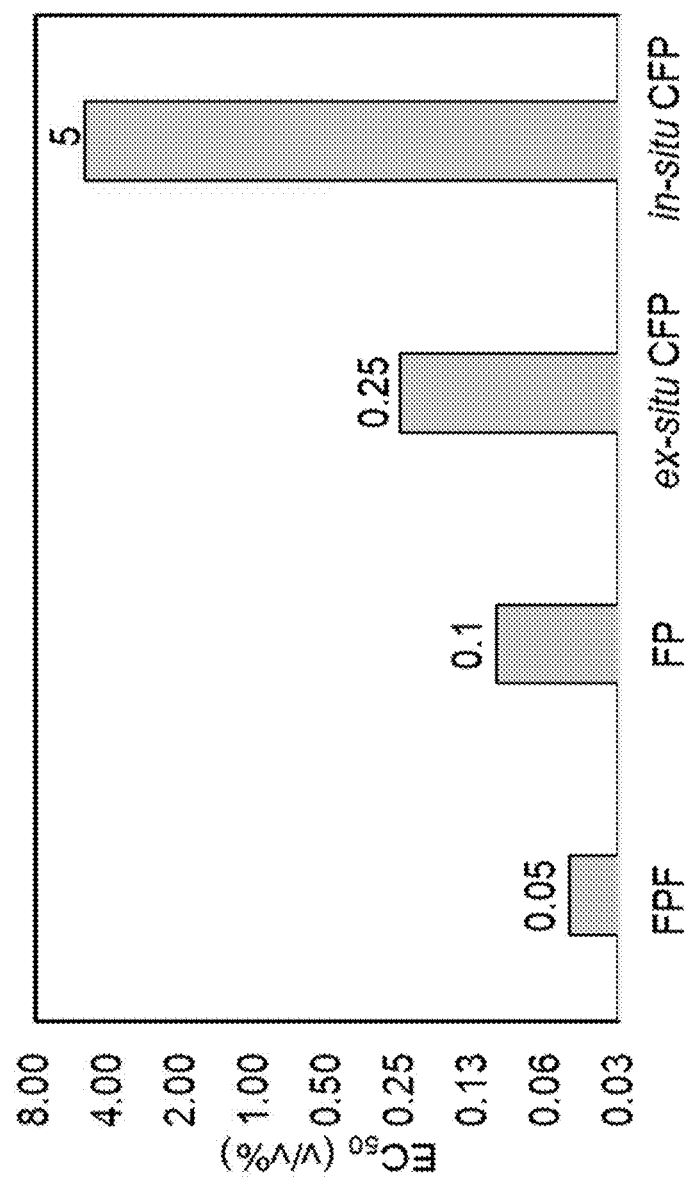
FIG. 6 depicts $EC_{50}$ values of the different thermochemical (TC) waste water streams on *P. putida* KT2440.
Figure 7:
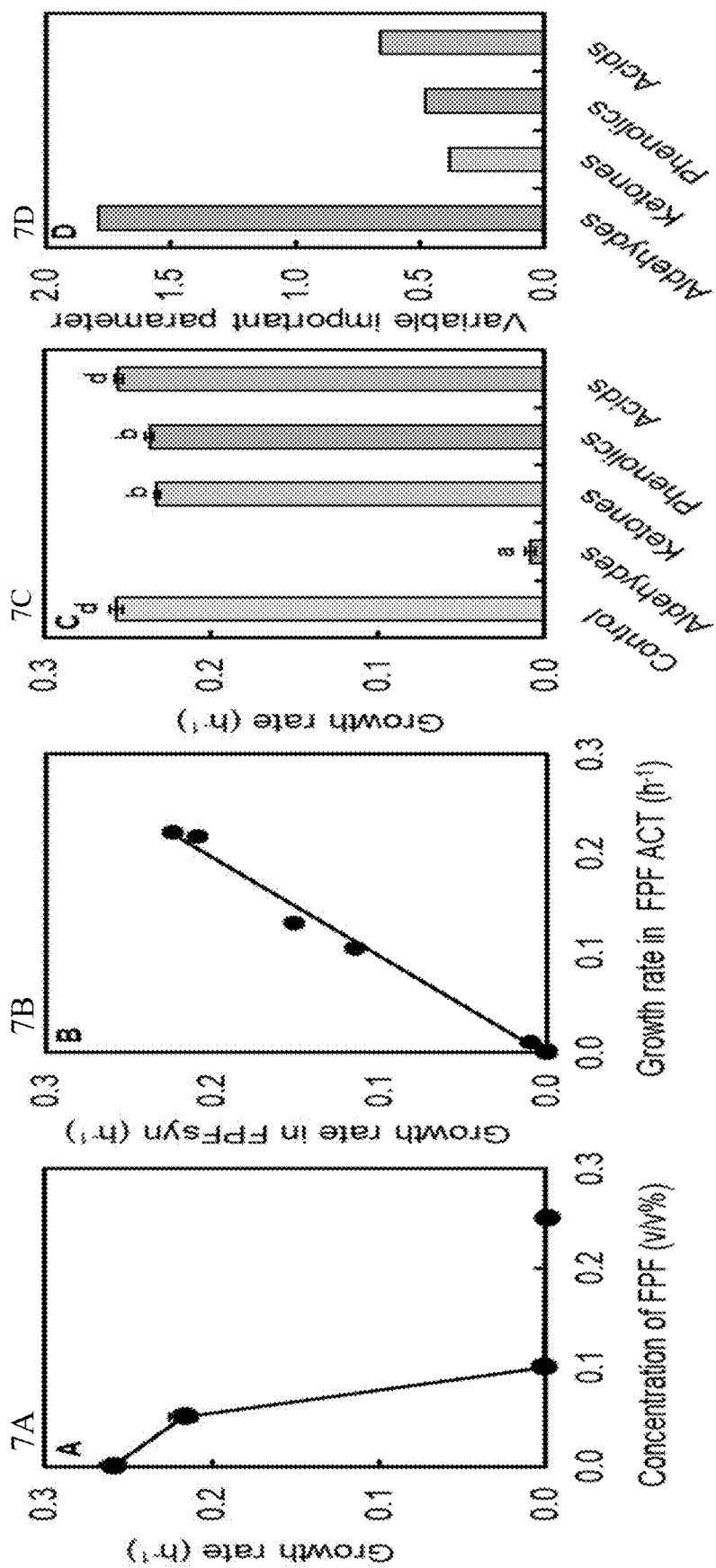
FIG. 7 depicts baseline toxicity of fast pyrolysis with fractionation (FPF) stream component to toxicity with *P. putida* KT2440.

Several exemplary TC wastewater streams from FP and CFP pilot-scale processes were evaluated for their baseline toxicity to *P. putida* KT2440 (see FIG. 6). The most toxic wastewater stream is from a FP-with-fractionation (FPF) process. This stream is lethal at a concentration of 0.1% (v/v), which translates to 0.34 g/L of organic carbon (see FIG. 7A). Compounds in the FPF stream were identified and quantified to a mass closure of 80% (see Table 6). Using these data, a synthetic FPF mixture was formulated with the 32 most abundant compounds present in FPF, and this stream accurately captures the FPF toxicity to *P. putida* (see FIG. 7B, where $R^2=0.99$). The compounds present in the FPF stream were classified according to chemical functionality, aldehydes, ketones, phenolics, or acids, and the growth rate of *P. putida* was evaluated against each class of compounds. FIG. 7C shows that of the functional group classes, aldehydes are the predominant contributor of FPF toxicity ($p<0.05$), ketones and phenols have minor effects ($p<0.05$), and acids contribute little to toxicity, at least at the concentration tested here ($p>0.05$). Given that combinational effects of these different functional groups likely contribute to the total toxicity of FPF, a fractional factorial experiment was performed, followed by partial least square (PLS) modeling to characterize the individual contributions of the functional groups to the total toxicity of the FPF stream (see FIG. 8). The variable important parameter (VIP) score of the functional groups, an indicator of the contribution of individual parameters to the total effect, confirmed that aldehydes contribute to the combinational toxicity of the FPF stream, followed by acids, phenols, and ketones (see FIG. 7D). $EC_{50}$ values (the effective concentration that decreases the growth rate by 50%) for the 32 most abundant compounds were also determined (see Table 7). The results reveal that formaldehyde and glycolaldehyde (GA) have low $EC_{50}$ values of about 2 mM for *P. putida* compared to those of ketones, phenols, and acids. Overall, these results demonstrate that aldehydes are the main contributors to the FPF stream toxicity and suggest that alleviating aldehyde toxicity contributes to the development of a strain tolerant to TC wastewater streams.

Example 11

Mechanism of FPF Stream Toxicity

Figures 9A, 9B:
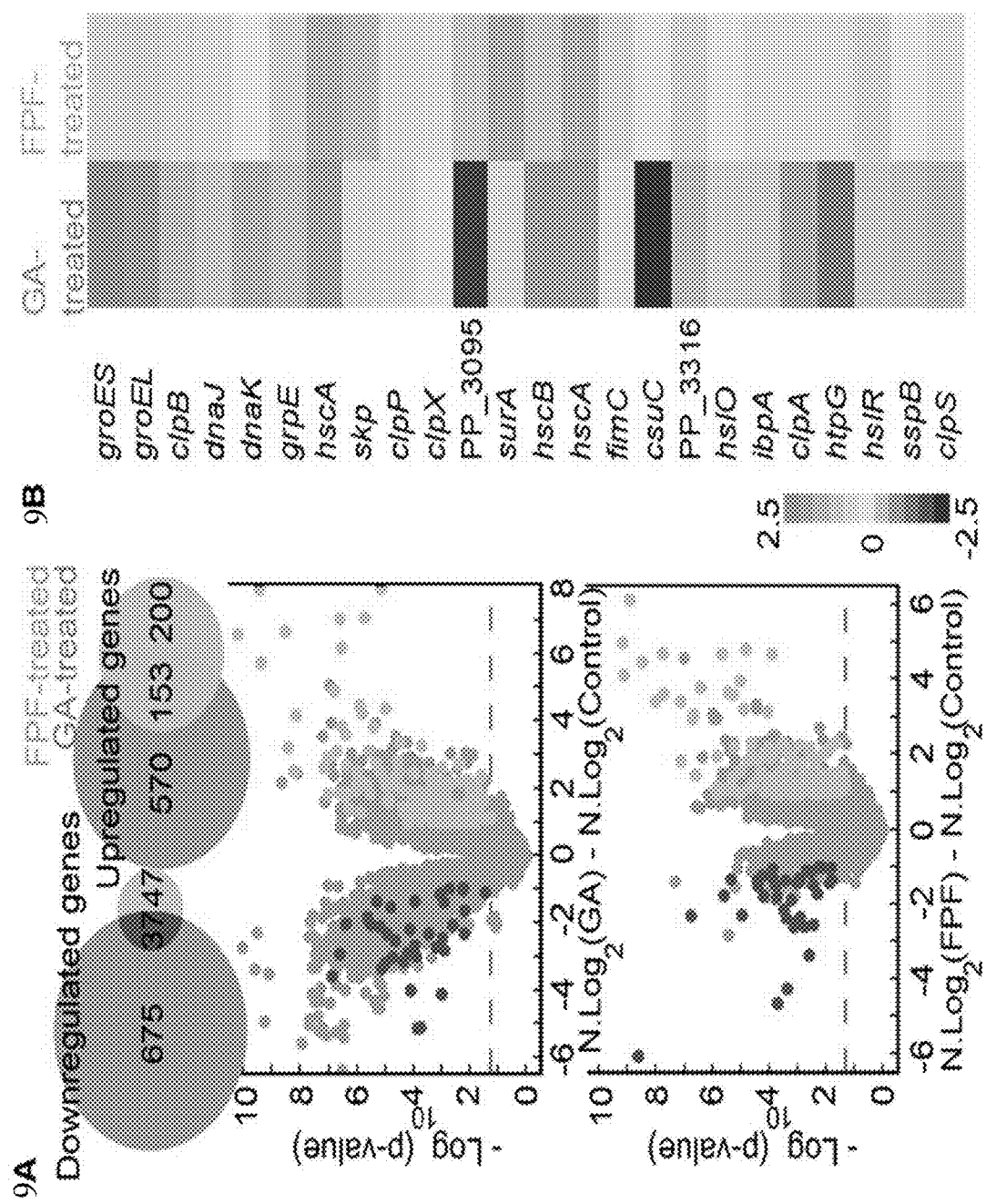
FIG. 9 represents the global transcriptional profiles of the strains under GA or FPF-induced stress.

To identify the molecular mechanism of the FPF stream toxicity to *P. putida* KT2440 and identify rational genetic targets to enhance its tolerance, RNA-seq transcriptomics and proteomics analyses were performed under FPF-induced stress. The same analyses were conducted with a single toxic aldehyde. Specifically, GA is a ubiquitous compound found in TC wastewater streams in concentrations from about 3 mM to about 850 mM, and FPF contains 785 mM of GA. Hence, it was selected as a model aldehyde for parallel multi-omics analysis. In the RNA-seq analysis, 43% of highly up-regulated and 44% of down-regulated genes in FPF-treated cells are in common with GA-treated cells (see FIG. 9A). The genes that are significantly up-regulated in *P. putida* KT2440 in both GA and FPF-treatments (see Table 8) suggest that the microbe may convert inhibitory aldehydes including GA into less toxic acids/alcohols by inducing expression of dehydrogenases (PP_2425-7, PP_2476, PP_3621-23, PP_3745-47), export the inhibitory compounds by upregulating transporters and efflux pumps (PP_3425_5-7; PP_2647), and/or alter its cell envelope (PP_2213, PP_3519). Gene ontology (GO) enrichment analysis reveals low representation of the energy and core metabolism categories including ATP synthesis, succinate-CoA ligase (ADP formation), and nitrogen-metal bond-forming complex coordination, which is consistent with decreased growth after treatment with the FPF stream compared to control cultures (see Table 9). Enrichment in iron binding and siderophore transport GO terms upon GA treatment may be a response to demand for Fe—S cofactors for the upregulated glycolate oxidase (PP_3747), coproporphyrinogen III oxidase (PP_4264), and a protein annotated as Fe—S cluster-binding (PP_4259). The glycolate oxidase encoded by glcDEFG (PP_3745-7) is responsible for detoxifying GA to the less toxic glyoxylic acid via glycolic acids. In addition, there was an enrichment of genes with the GO term for ribosome structural constituents in GA-treated cells, suggesting that GA disrupts translational machinery.

TABLE 9

Gene ontologies enriched in differentially expressed genes identified by RNA seq analysis after FPF or glycolaldehyde-treatment.

|  | FPF-treated vs untreated | GA-treated vs untreated |
| --- | --- | --- |
| Upregulated genes | No GO enrichment | Structural constituent of ribosome<br>Iron ion binding<br>Siderophore transport |
| Downregulated genes | Alginic acid biosynthesis process<br>Proton-transporting ATP synthase complex, catalytic core F(1)<br>Plasma membrane ATP synthesis coupled proton transport<br>Succinate-CoA ligase (ADP-forming) activity<br>Proton-transporting ATP synthase activity, Rotational mechanism | No GO enrichment |

TABLE 9-continued

Gene ontologies enriched in differentially expressed genes identified by
RNA seq analysis after FPF or glycolaldehyde-treatment.

| FPF-treated vs untreated | GA-treated vs untreated |
|---|---|
| Ligase activity, forming nitrogen-metal bonds, forming coordination complexes | |

Figure 22:
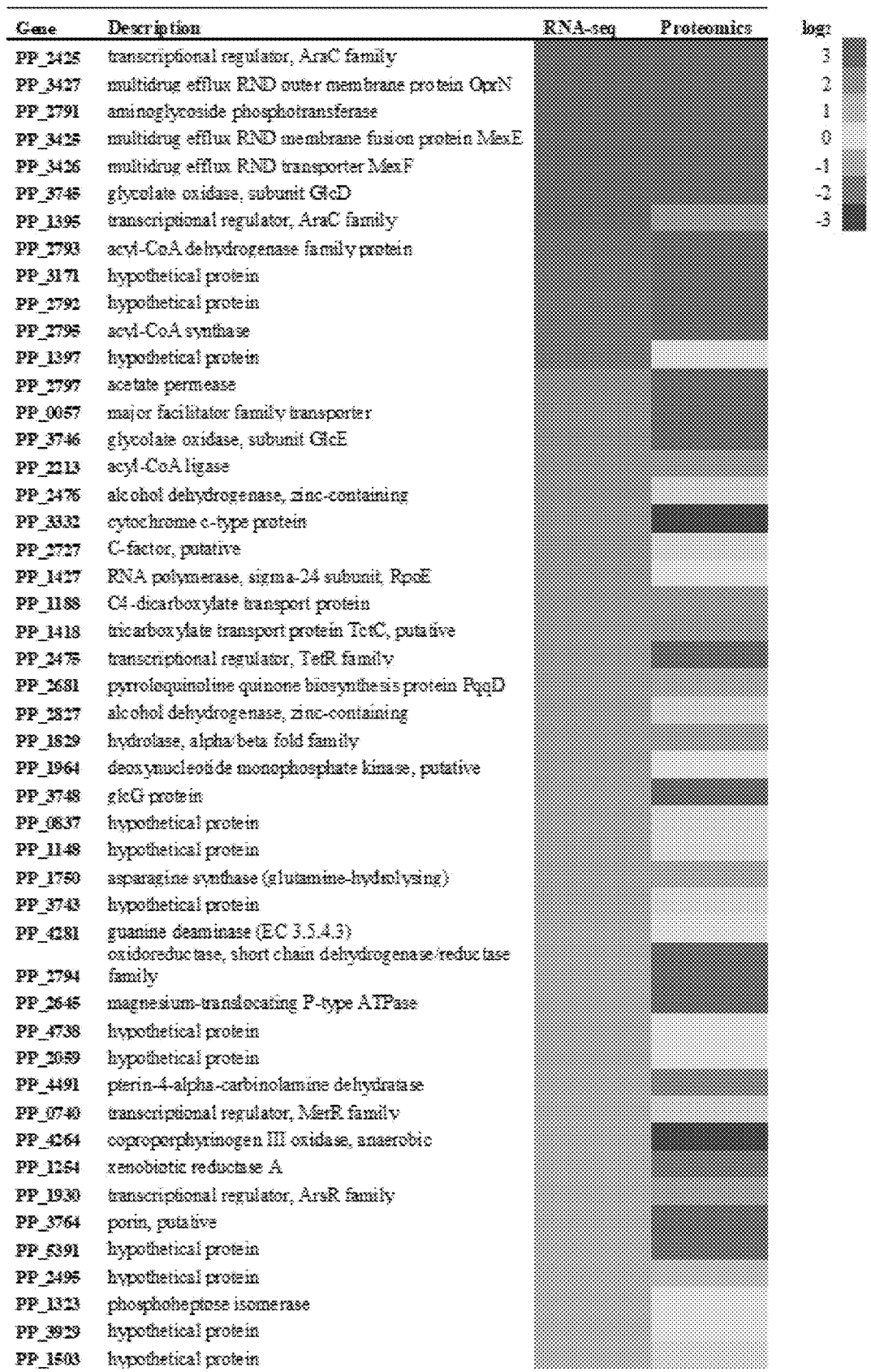
FIG. 22 depicts a comparison of the most highly expressed RNAs and protein expression in *putida* KT2440 upon FPF treatment.

In parallel to RNAseq analysis, proteomic analyses were performed to detect the stress response of P. putida KT2440 at the level of translation. The results reveal that levels of many proteins are significantly different in response to GA stress (151 proteins increased in abundance, N·log$_2$>1, p<0.05; 218 proteins decreased in abundance N·log$_2$<−1, p<0.05) and FPF (319 proteins increased in abundance, N·log$_2$>1, p<0.05; 403 proteins decreased in abundance N·log$_2$<−1, p<0.05). In agreement with GO enrichment analysis of differentially expressed genes, similar enrichment of GO-terms was detected for significantly decreased in abundance proteins after FPF treatment (see Table 10). Interestingly, a disparity between transcription and translation in FPF-treated cells was observed. Several proteins were significantly decreased in abundance after FPF treatment, although the gene expression was highly upregulated (N·log$_2$>1, p<0.05) (see FIG. 22), including PP_0149; AapP, PP_1300; TctC, PP_1418; AsnB, PP_1750; TetR, PP_2475; PP_3610; PP_3332; HemN, PP_4264; and PP_5391 (log$_2$<−1, p<0.05). None of these proteins exhibit a secretion signal peptide according to SignalP 4.1. Ab initio predictions of non-classical protein secretion using SecretomeP 2.0 Server was only positive with PP_5391. These results suggest that these proteins are subject to post-transcriptional or post-translational regulation or may have been damaged in FPF-treated cells, but that differences in protein and mRNA abundance are not likely attributed to secretion.

Aldehydes, the key toxic component of the FPF stream, can confer molecular toxicity via protein damage. Indeed, GA, the major aldehyde present in FPF is a well-known post-translational protein-damaging agent. To demonstrate the in vivo effect of GA and FPF in this system, a GFP-expressing strain of P. putida KT2440 was cultured in medium supplemented with GA (2 mM), FPF (0.05% (v/v)), or un-supplemented. Cell-free extract from these conditions was immunoblotted to detect the presence of GFP. In GA or FPF-treated cells, a band around 37 kDa was observed (see FIG. 12C), suggesting a cross-linking of GFP (28 kDa) with and an unidentified protein of around 10 kDa. GA or FPF-treated cells also exhibit significantly lower free-GFP levels compared to the untreated cells (46.8% in GA-treated cells and 18.1% in FPF-treated cells relative to the untreated controls). Furthermore, GFP inclusion bodies formed in cells treated with GA or FPF, which might be due to misfolding or cross-linking of the GFP protein. Flow cytometric analysis revealed that GA or FPF-treated cells have a weaker GFP signal relative to the control (see FIG. 12D). Together, these results suggest that FPF may be crosslinking and/or causing misfolding of GFP. Although the category was not enriched in GO ontologies analysis, we found that several chaperone proteins, which are responsible for turnover and refolding of damaged proteins, including clpB, groES, groEL, dnaK, dnaJ, grpE, and htpG were among the most highly expressed genes under the GA or FPF treatment (see FIG. 9B). Collectively, these results suggest that protein damage is a key contributor of FPF toxicity. Thus, in an embodiment, overexpression of chaperones to rescue damaged or misfolded proteins was chosen as a strategy to enhance the tolerance of P. putida to FPF.

Example 12

Strain Tolerance to FPF Stream Toxicity

Figure 10:
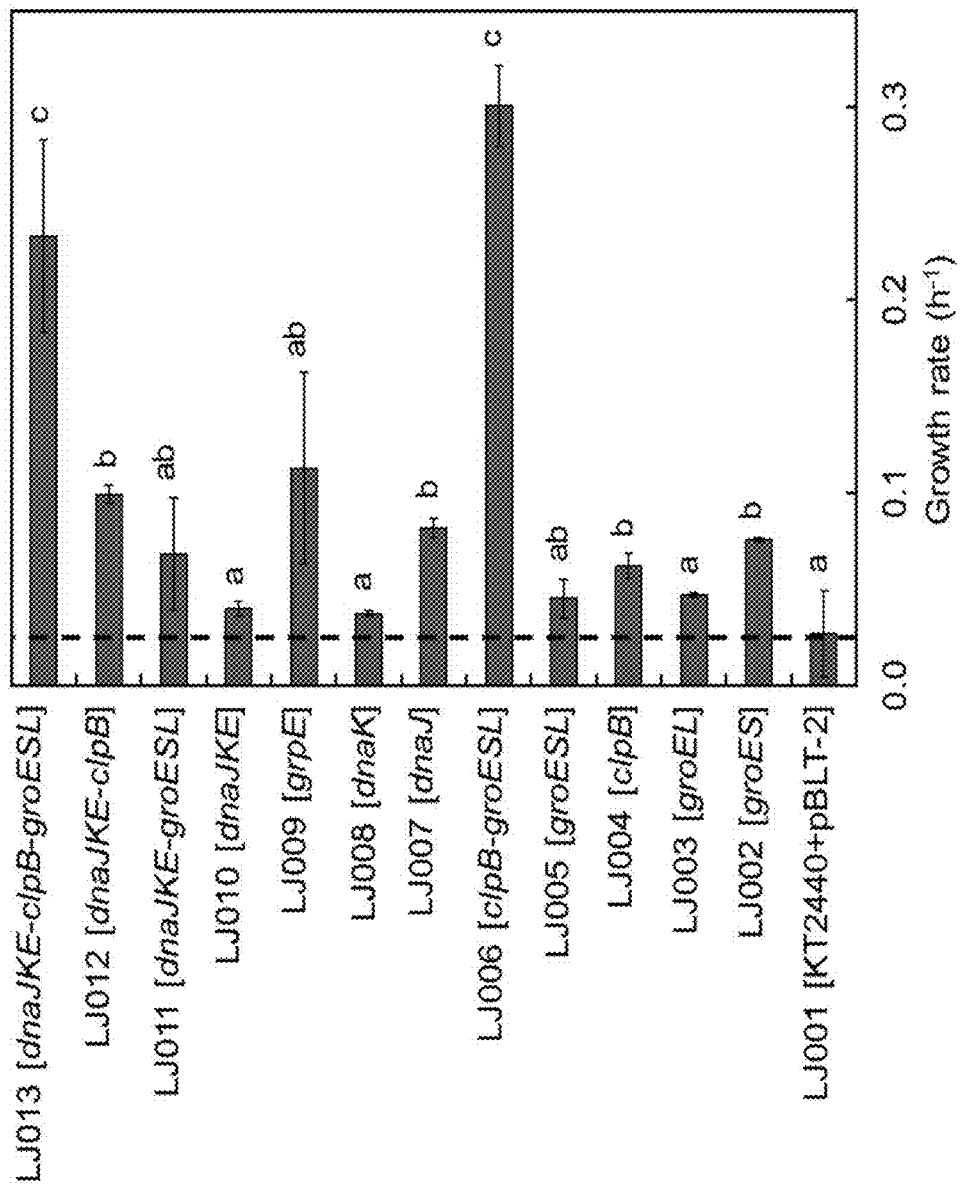
FIG. 10 depicts the growth rates of chaperone-expressing, non-naturally occurring *P. putida* KT2440 strains in FPF.
Figures 13A, 13B:
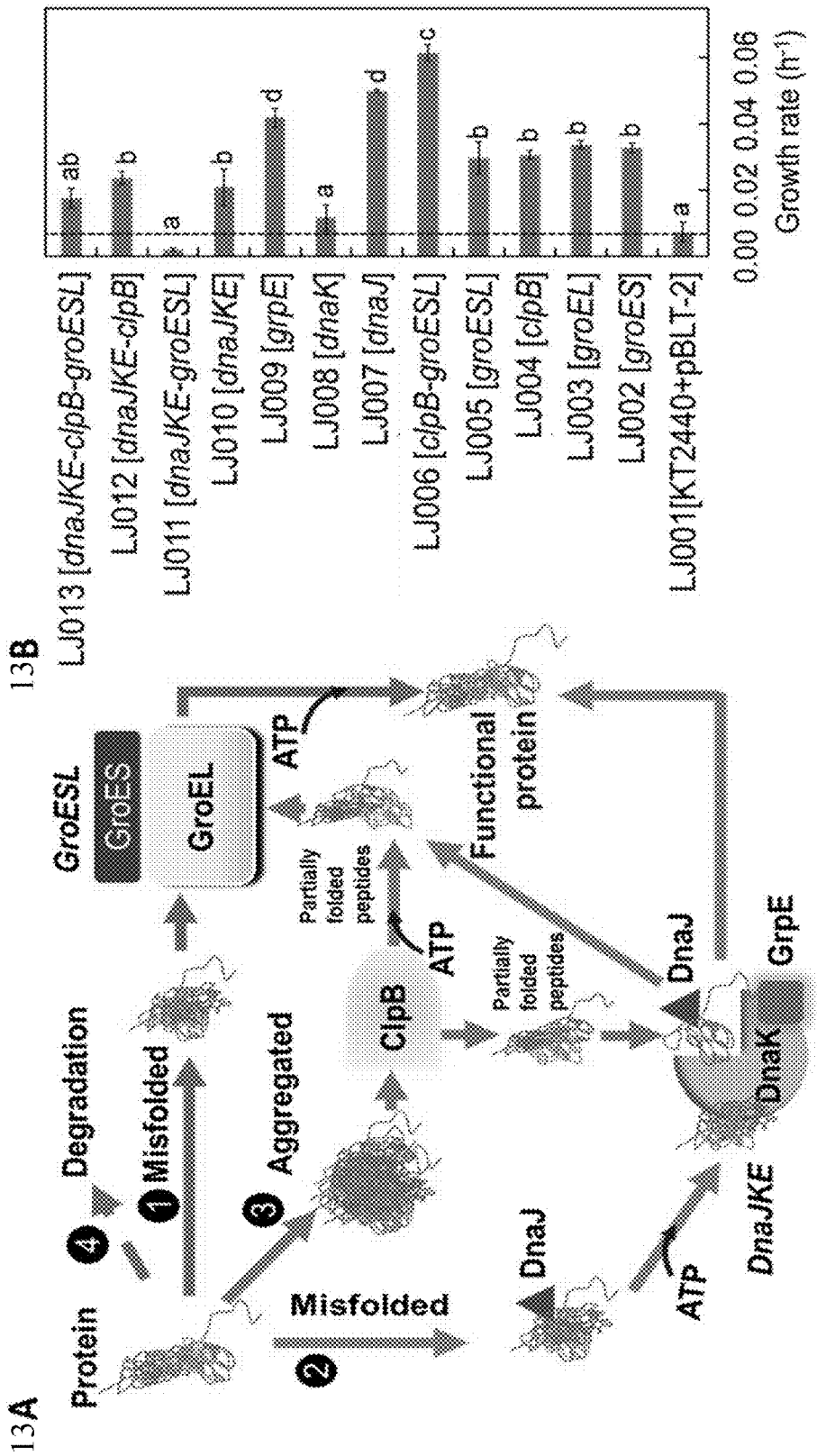
FIG. 13 depicts (A) a schematic illustration of the mechanisms of protein recovery by chaperone cascades and (B) the effect of overexpression of chaperone proteins on tolerance of *P. putida* KT2440 to glycolaldehyde.

Two major protein recovery chaperone machineries, DnaJKE and GroESL, were targeted to improve the tolerance of P. putida to FPF (see FIG. 13A). Given that protein cross-linking may also play a role, the protein disaggregating chaperone, ClpB, was also evaluated. Plasmids were constructed to overexpress combinations of these chaperone genes, and the tolerance of P. putida KT2440 containing these plasmids to GA and FPF was investigated. Co-expression of clpB, groES, and groEL chaperones had a synergistic effect on improving the tolerance of P. putida KT2440 to FPF (see FIG. 10), and an additive effect on tolerance to GA (see FIG. 13B) relative to the overexpression of those chaperone genes alone or all other combinations (p<0.05).

Figure 11:
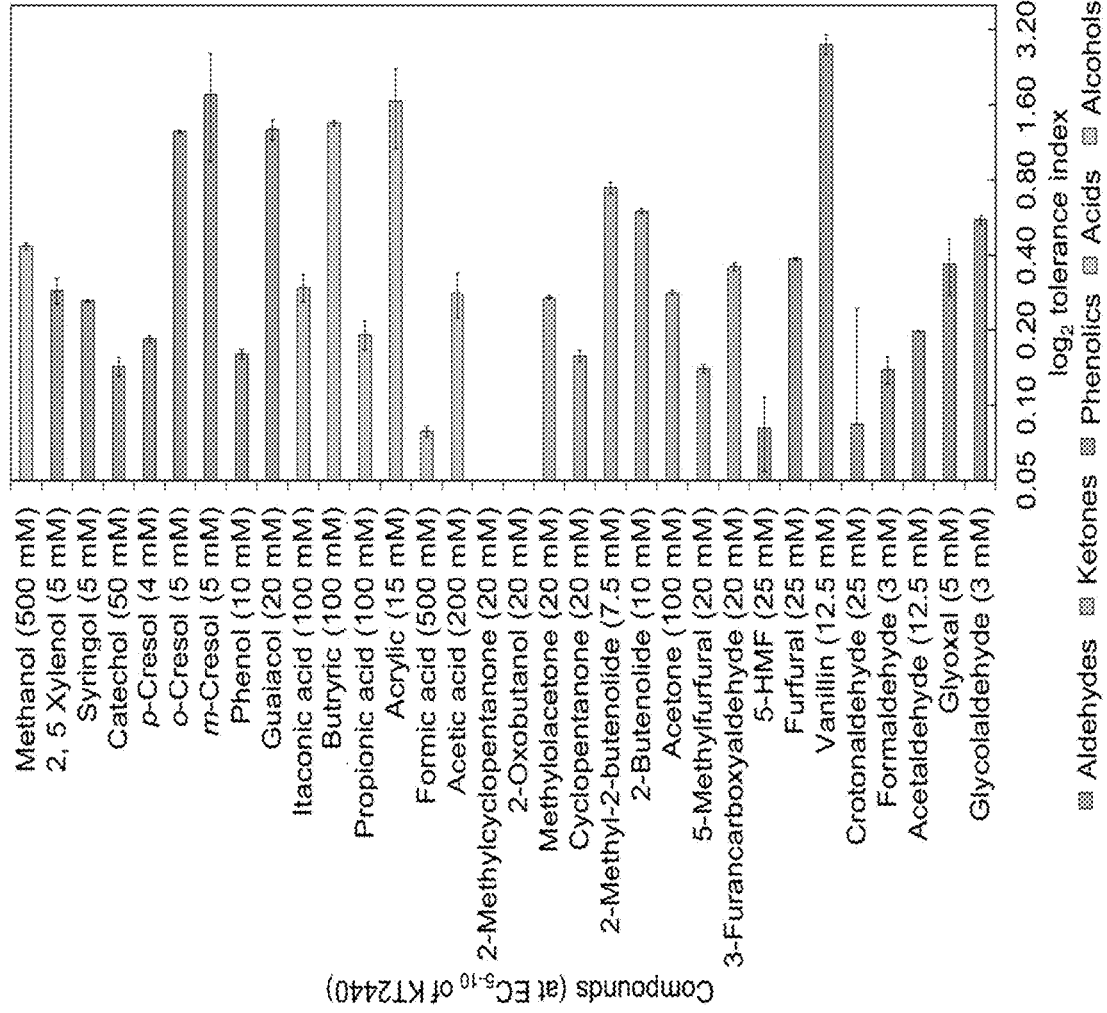
FIG. 11 depicts the tolerance improvement of a chaperone-expressing *P. putida* strain to compounds found in the TC wastewater streams.
Figure 14:
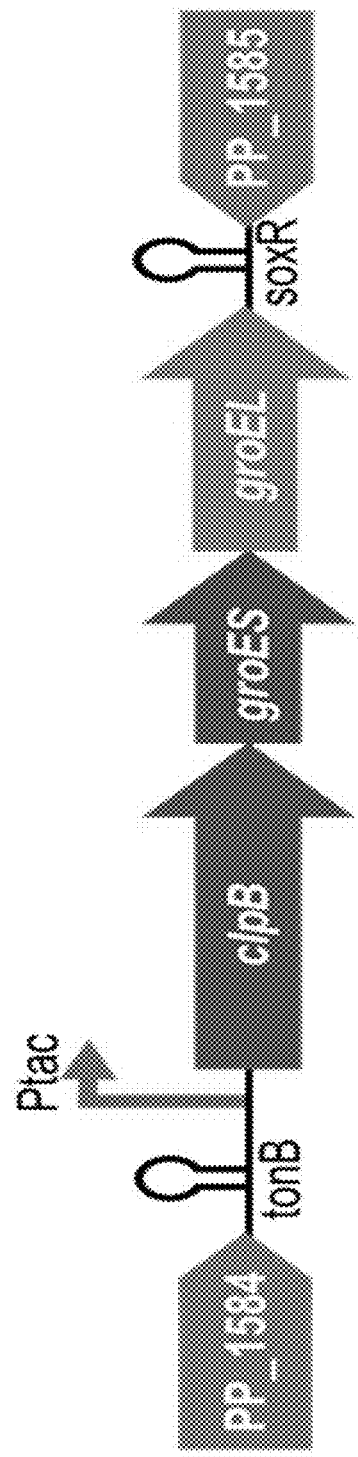
FIG. 14 is a schematic representation of the configuration of genomically integrated cassette of the synthetic chaperone operon including clpB, groES and groEL genes.

Based on these results, an industrially applicable strain that overexpresses these genes without the use of plasmids was developed. To accomplish this, a second copy of the native clpB, groES, and groEL chaperone genes was integrated into the chromosomal genome of P. putida KT2440 at intergenic site between PP_1584 and PP_1585 (see FIG. 14). The tac promoter, which is a strong, constitutive promoter in P. putida KT2440, was included to drive expression of these genes. The tolerance of this created strain, LJ014, to increasing concentrations of the 32 most abundant compounds in the TC wastewater streams was tested and the strain was found to exhibit tolerance to higher concentrations of 30 of these relative to wild-type P. putida KT2440 (all but 2-methylcylopentenone and 2-oxobutanol, see FIG. 11). These include aldehydes (vanillin by 7.5-fold and GA by 1.5-fold), ketones (2-butenolide or 3-methyl-2-butenolide by 1.5-fold), acids (acrylic acid by 3.5-fold and butyric acid by 2.5-fold), phenolics (guaiacol by 3.5-fold and m-cresol by 3.5-fold), and to the prevalent alcohol, methanol (by 1.5-fold). Since enhanced tolerance to the majority of compounds present in the TC wastewater streams analyzed here was achieved, the performance of strain LJ014 in FPF was then examined.

Example 13

Survival and Protein Recovery of Chaperone-Expressing Strains Exposed to FPF Streams.

To evaluate the viability of the GroESL and ClpB overexpression strain, LJ014, and wild-type P. putida KT2440, the cells were treated with 1% (v/v) FPF and fluorescence-based live/dead cell viability assays were performed using flow cytometry. LJ014 exhibits high cell viability after 12 hours of FPF treatment relative to KT2440 (82.9±7.5-fold higher, p<0.01, see FIG. 12A). Parallel colony-forming assays revealed that only LJ014 formed colonies on LB plates after 12 hours of exposure to FPF (FIG. 12B). These data demonstrate that strong, constitutive co-expression of the chaperones genes clpB, groES, and groEL markedly improves the cell viability and growth of P. putida KT2440 exposed to FPF.

The fate of GFP in the LJ014 strain after treatment with FPF was then examined. Immunoblot analysis revealed that the free GFP level was significantly higher in the GPF-expressing LJ014 relative to the GFP-expressing wild-type P. putida KT2440 after 3 hours of FPF treatment (48.2% vs 18.5% relative to free GFP of untreated controls). Meanwhile, the amount of cross-linked GFP protein was reduced in the GFP-expressing LJ014 strain relative to the wild-type (from 74.9% to 57.3%, relative to the free GFP level of untreated controls, see FIG. 12C).

Consistent with a larger amount of free GFP, the GFP-expressing LJ014 cells exhibit a 3-fold higher GFP fluorescent signal compared to that of the GFP-expressing wild-type strain when exposed to FPF (see FIG. 12D). Overall, these results demonstrate that the chaperone overexpression strain, LJ014, produces a larger amount of functional GFP relative to P. putida KT2440 in the FPF stream.

Example 14

Proteomic Profile of Chaperone-Expressing Strains

Figure 15:
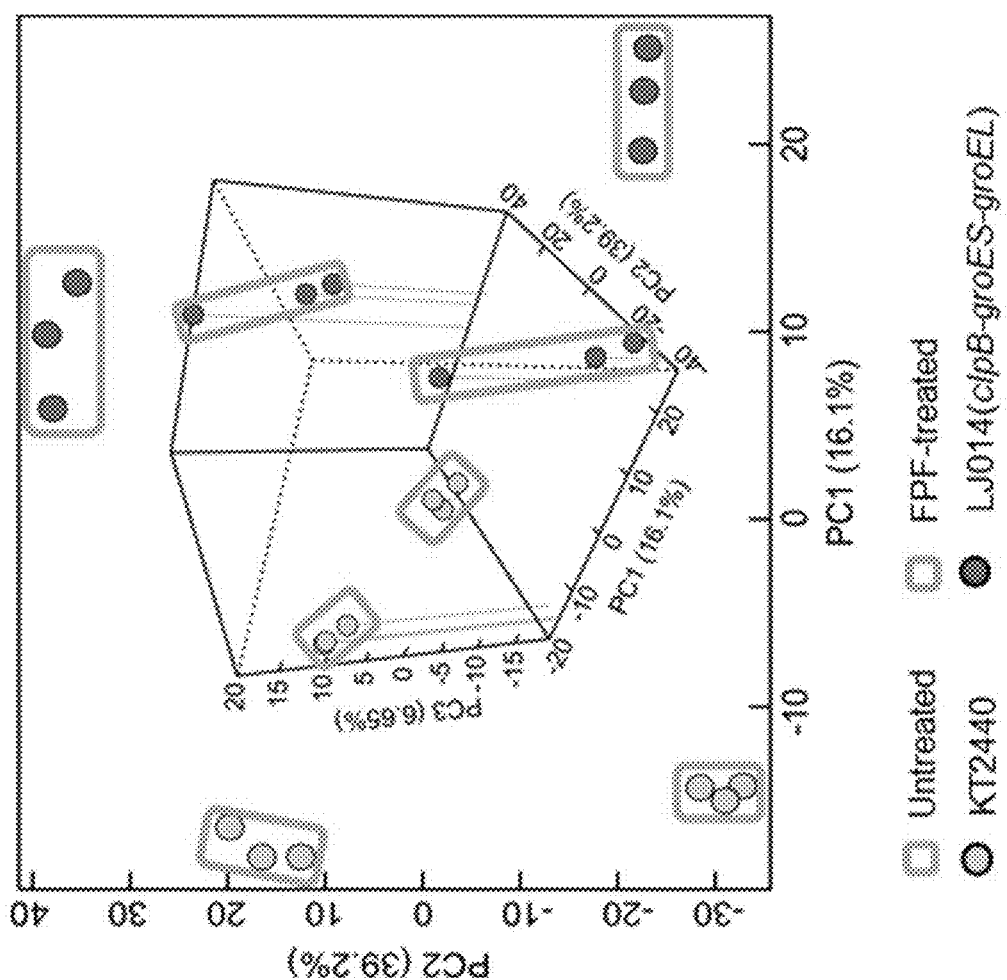
FIG. 15 depicts 2D- and 3D-PLS global proteomics plots of the strains with or without treatment of FPF at a concentration of about 0.5% v/v.
Figures 16A, 16B:
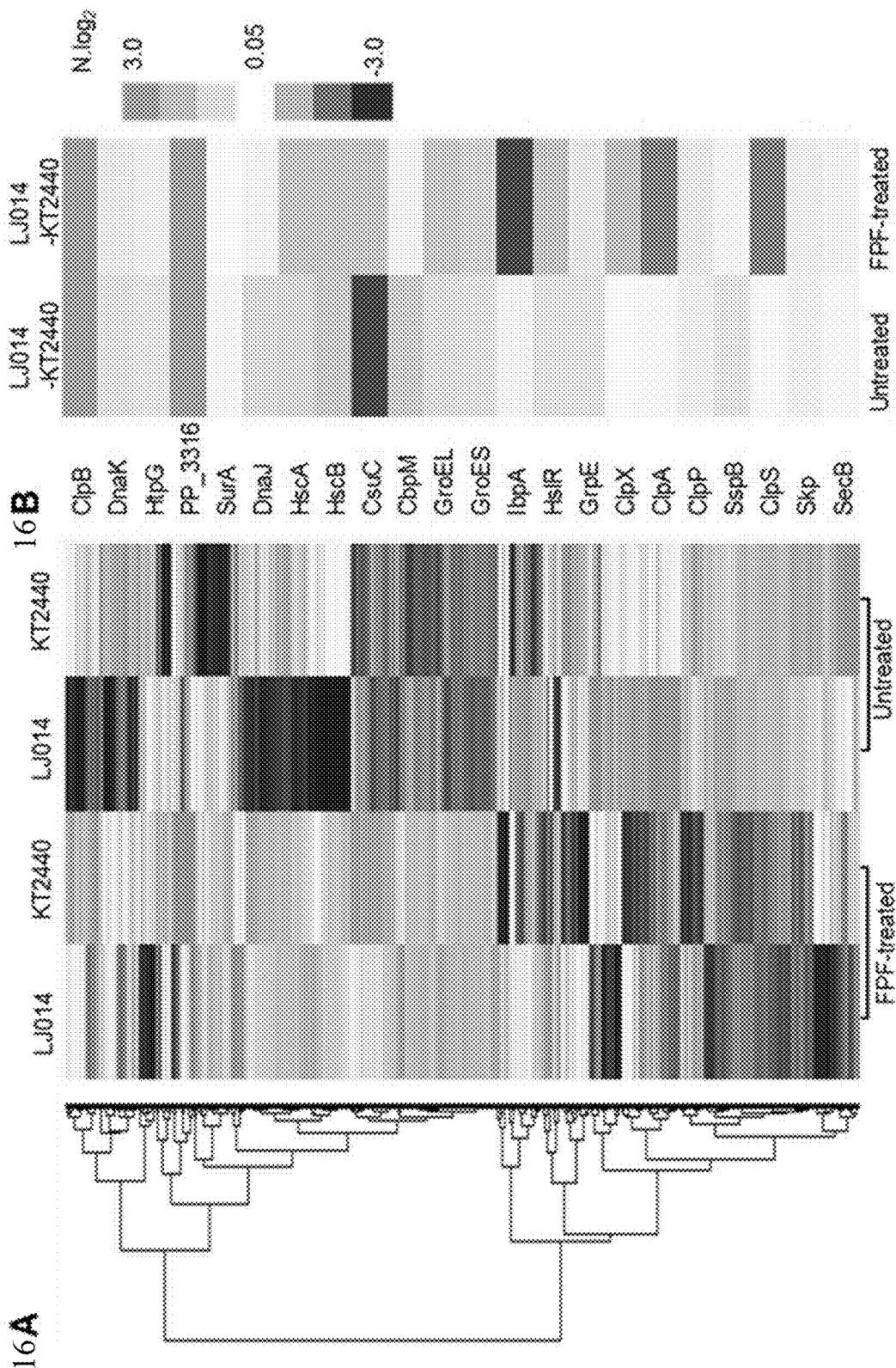
FIG. 16 depicts (A) a heat map of global proteomics profiles and (B) a heat map of the N·log 2 values of chaperone proteins of the LJ014 and the KT2440 strains in M9 medium containing 20 mM glucose with or without 0.5% (v/v) FPF.

Changes to the global proteomic profile of LJ014 were evaluated. Proteomes of treated and untreated LJ014 and KT2440 were distinct on the PLS plot see (FIG. 15). In the absence of any treatment, the overexpression of clpB, groES, and groEL in LJ0114 resulted in increased abundance of 76 proteins (N·log$_2$>1, p<0.05) and decreased abundance of 169 proteins (N·log$_2$<1, p<0.05) relative to KT2440 (see FIG. 16A). DnaJKE and HscB (a co-chaperone of maturation pathway of Fe—S proteins), and chaperone assisting ATPase protein encoded by PP_3316, were among the proteins more highly abundance in LJ014 (see FIG. 16B). The stoichiometry of chaperones affects the overall efficiency of the system, so the increase in abundance of these other chaperones may be a response to overexpression of ClpB, GroES, and GroEL in LJ014, and the whole chaperone cascade might be tuned appropriately to the stream toxicity.

However, GO enrichment analysis did not identify any GO categories among the proteins that were differentially expressed between the LJ014 and KT2440 grown in M9 medium containing 20 mM glucose. As shown in FIG. 15, the samples from LJ014 and KT2440 treated with FPF were also distantly clustered in the PLS analysis plot, reflecting a difference in their global proteomic profiles. When grown in the presence of the FPF stream, siderophore and ion binding proteins GO categories were enriched in the LJ014 strain relative to the KT2440 wild-type (see Table 10). LJ014 had 206 proteins that are increased in abundance relative to the KT2440 strain in M9 medium containing FPF (N·log$_2$>1, p<0.05; see Table 12), some of which could contribute to its enhanced tolerance. Increased protein expression of chaperones ClpB, GroES, and GroEL also resulted in increased in abundance of proteins involved in universal stress response (PP_2130), redox cofactor biosynthesis (UbiG, PP_1765; Dxr, PP_1597; GrxC, PP_5054, GloB, PP_4144) detoxification of toxic compounds (YeaE, PP_3120; PP_3248; Ttg2E, PP_0962; PP_3671), DNA repair (MutY, PP_0286; Ung, PP_1413; RecC, PP_4674), RNA processing (RnpA, PP_0008), membrane stability (OpgH, PP_5025), regulation of protein synthesis and ribosomal stability (RsfS, PP_4809), and central metabolism (ZwfB, PP_4042; GlpD, PP_1073). Notably, several proteins that were significantly decreased in abundance at the protein level despite the high expression at transcriptional level in KT2440 treated with FPF, as reported above, were highly abundance in FPF-treated LJ014 cells. These included, PP_0837 (N·log$_2$=2.22, p=0.022); TetR, PP_1387 (N·log$_2$=1.17, p=0.014); TctC, PP_1418 (N·log$_2$=1.47, p=0.009); PP_1503 (N·log$_2$=8.29, p=0.001); AsnB, PP_1750 (N·log$_2$=5.29, p=0.004); PP_2059 (N·log$_2$=4.39, p=0.013); PP_3332 (N·log$_2$=2.6, p=0.0321); PP_3610 (log 2=1.'72, p=0.014); Gad, PP_4281 (N·log$_2$=1.54, p=0.002); PP_4738 (N·log$_2$=4.95, p=0.000); and PP_5391 (N·log$_2$=3.35, p=0.001). These results indicate that overexpression of GroESL and ClpB leads to higher abundance of proteins associated with other cellular defense machineries, and recovery of protein biosynthesis under FPF stress, which overall leads to a more robust cellular defense.

TABLE 12

Proteins more highly expressed in LJ014 relative to KT2440 when treated with 0.05% FPF (V/V).

| Protein | Description | N. Log$_2$ |
|---|---|---|
| PP_1315 | 50S ribosomal protein L13 RplM | 1.26 |
| PP_3316 | Putative Chaperone-associated ATPase | 4.14 |
| PP_1911 | 50S ribosomal protein L32 RpmF | 1.19 |
| PP_0938 | Uncharacterized protein | 1.81 |
| PP_4809 | Ribosomal silencing factor RsfS | 2.84 |
| PP_3095 | Protein ClpV1 | 3.27 |
| PP_4007 | Translation initiation factor IF-1 InfA | 2.02 |
| PP_3332 | Putative cytochrome c-type protein | 1.07 |
| PP_2468 | 50S ribosomal protein L20 RplT | 1.38 |
| PP_1352 | UPF0234 protein | 1.13 |
| PP_3248 | Dyp-type peroxidase family protein | 1.02 |
| PP_5171 | Sulfate ABC transporter Sbp-II | 1.36 |
| PP_2698 | 5-methyltetrahydropteroyltriglutamate-homocysteine methyltransferase metE | 1.61 |
| PP_0472 | 50S ribosomal protein L30 RpmD | 1.36 |
| PP_3785 | Uncharacterized protein | 1.02 |
| PP_1765 | Ubiquinone biosynthesis O-methyltransferase UbiG | 1.77 |
| PP_4375 | Flagellar protein FliS | 1.61 |
| PP_3722 | Alanine racemase Alr | 2.02 |
| PP_2008 | 2,4-dienoyl-CoA reductase OS = Pseudomonas putida FadH | 4.78 |
| PP_5141 | Thymidylate synthase ThyA | 1.79 |
| PP_3335 | Uncharacterized protein | 3.15 |
| PP_4770 | Uncharacterized protein | 1.51 |
| PP_5103 | tRNA (guanine-N (7)-)-methyltransferase TrmB | 1.88 |
| PP_0046 | Tyrosine-specific outer membrane porin D OpdT-I | 1.13 |
| PP_1673 | Hydrogenobyrinate a,c-diamide synthase CobB | 1.08 |
| PP_4717 | Dihydropteroate synthase FolP | 1.21 |
| PP_4613 | Outer membrane ferric citrate porin FecA | 1.95 |
| PP_0267 | Putative Outer membrane ferric siderophore receptor | 2.73 |
| PP_4362 | Uncharacterized protein | 1.79 |
| PP_5025 | Glucans biosynthesis glucosyltransferase OpgH | 1.43 |
| PP_3321 | Uncharacterized protein | 2.27 |
| PP_1619 | tRNA pseudouridine synthase TruD | 1.11 |
| PP_1757 | DNA-binding transcriptional dual regulator BolA | 1.19 |
| PP_4601 | Transcriptional regulator, LysR family | 1.72 |
| PP_3120 | Methylglyoxal reductase YeaE | 1.50 |
| PP_2132 | Universal stress protein | 4.08 |
| PP_0845 | Co-chaperone protein HscB | 1.08 |
| PP_4144 | Hydroxyacylglutathione hydrolase GloB | 1.01 |
| PP_5097 | Homoserine O-acetyltransferase MetX | 1.79 |
| PP_3958 | Na$^+$/H$^+$ antiporter NhaA 2 | 1.27 |
| PP_0354 | CBS domain protein | 1.01 |
| PP_0529 | Exodeoxyribonuclease 7 small subunit XseB | 1.31 |
| PP_5361 | 47 kDa protein | 2.20 |
| PP_3828 | Molybdate-binding periplasmic protein ModA | 1.13 |
| PP_0879 | Dipeptide ABC transporter-putative ATP binding subunit DppD PE | 1.19 |
| PP_3948 | Nicotinate dehydrogenase subunit B NicB | 2.48 |
| PP_5212 | Oxidoreductase, iron-sulfur-binding | 1.06 |
| PP_3654 | Leucine-responsive regulatory protein | 1.92 |
| PP_0341 | ADP-heptose: LPS heptosyltransferase II WaaF | 2.07 |
| PP_0962 | Toluene-tolerance protein Ttg2E | 2.05 |
| PP_2668 | ABC efflux transporter, ATP-binding protein | 1.06 |

TABLE 12-continued

Proteins more highly expressed in LJ014 relative to KT2440 when treated with 0.05% FPF (V/V).

| Protein | Description | N. Log$_2$ |
|---|---|---|
| PP_1209 | Cold-shock protein | 1.03 |
| PP_2440 | Alkyl hydroperoxide reductase subunit F AhpF | 1.36 |
| PP_4657 | Zinc metalloprotease YpfJ | 1.32 |
| PP_5045 | tRNA sulfurtransferase ThiI | 1.42 |
| PP_3056 | Putative Pyocin R2_PP, tail fiber protein | 2.61 |
| PP_2126 | DNA-binding response regulator, LuxR family | 4.58 |
| PP_2036 | Putative 4-hydroxy-tetrahydrodipicolinate synthase | 1.50 |
| PP_4066 | Methylglutaconyl-CoA hydratase LiuC | 1.23 |
| PP_1597 | 1-deoxy-D-xylulose 5-phosphate reductoisomerase Dxr | 4.35 |
| PP_4648 | Ribosomal RNA large subunit methyltransferase G RlmG | 1.02 |
| PP_0029 | Two component heavy metal response regulator CzcR-I | 1.50 |
| PP_5054 | Glutaredoxin 3 GrxC | 1.31 |
| PP_5388 | Probable exported copper efflux protein CusF | 1.59 |
| PP_5314 | Rubredoxin-NAD$^+$ reductase AlkT | 2.01 |
| PP_5068 | UPF0061 protein | 1.47 |
| PP_1936 | Uncharacterized protein | 3.17 |
| PP_3964 | Transposase | 5.50 |
| PP_1290 | Polysaccharide deacetylase family protein | 1.06 |
| PP_5431 | Uncharacterized protein | 1.62 |
| PP_0400 | Protein ApaG | 1.66 |
| PP_0242 | Transcriptional regulator, TetR | 1.29 |
| PP_4285 | 5-hydroxyisourate hydrolase PucM | 1.06 |
| PP_0342 | ADP-heptose: LPS heptosyltransferase I WaaC | 1.08 |
| PP_4814 | ATP-dependent protease La domain protein | 1.11 |
| PP_2485 | Uncharacterized protein | 3.43 |
| PP_4943 | Putative Glycosyl transferase | 1.06 |
| PP_0052 | Beta-lactamase domain protein, putative hydrolase | 1.90 |
| PP_3575 | Outer membrane ferric siderophore receptor | 3.87 |
| PP_1395 | Transcriptional regulator, AraC | 1.00 |
| PP_2696 | DNA-binding transcriptional regulator, homocysteine-binding MetR-II | 1.06 |
| PP_2447 | Uncharacterized protein | 1.78 |
| PP_3104 | Uncharacterized protein | 1.88 |
| PP_0286 | Adenine glycosylase MutY | 1.19 |
| PP_3989 | DNA-cytosine methyltransferase | 2.71 |
| PP_5099 | Uncharacterized protein | 1.43 |
| PP_2079 | Uncharacterized protein | 1.10 |
| PP_0237 | Aliphatic sulfonate ABC transporter-periplasmic binding protein/transport of isethionate SsuA | 2.35 |
| PP_1262 | LysR family transcriptional regulator | 1.18 |
| PP_3509 | Glyoxalase family protein | 1.34 |
| PP_5274 | Uncharacterized protein | 1.45 |
| PP_3446 | L-threonine dehydratase IlvA-I | 1.11 |
| PP_1144 | Uncharacterized protein | 2.11 |
| PP_5253 | Arylesterase OS = Pseudomonas putida | 1.38 |
| PP_1128 | OmpA family protein | 2.93 |
| PP_3779 | Transcriptional regulator, LysR family | 2.78 |
| PP_3155 | Putative Outer membrane ferric siderophore receptor | 2.78 |
| PP_3008 | Uncharacterized protein | 2.65 |
| PP_1492 | Sensor histidine kinase/response regulator | 1.13 |
| PP_2016 | Uncharacterized protein | 1.16 |
| PP_2379 | Putative cytochrome oxidase biogenesis protein | 1.21 |
| PP_1073 | Glycerol-3-phosphate dehydrogenase GlpD | 2.01 |
| PP_0820 | GCN5-related N-acetyltransferase | 1.45 |
| PP_4745 | Transposase | 1.12 |
| PP_1413 | Uracil-DNA glycosylase Ung | 2.61 |
| PP_2414 | Uncharacterized protein | 1.29 |
| PP_5618 | Putative Cro/CI transcriptional regulator | 1.71 |
| PP_3573 | Putative Monooxygenase | 3.99 |
| PP_0307 | Uncharacterized protein | 1.59 |
| PP_5022 | Glutamine transport ATP-binding protein GlnQ | 1.09 |
| PP_1221 | Colicin S4 and filamentous phage transport system TolA | 1.97 |
| PP_1677 | Cobyric acid synthase CobQ | 2.66 |
| PP_2650 | Putative 4-hydroxybutyrate dehydrogenase Gbd | 3.08 |
| PP_2387 | Uncharacterized protein | 3.15 |
| PP_4042 | Glucose-6-phosphate 1-dehydrogenase ZwfB | 1.25 |
| PP_1672 | Cob(I)alamin adenolsyltransferase/cobinamide ATP-dependent adenolsyltransferase | 1.90 |
| PP_3139 | Glycosyl transferase, group 1 family protein | 1.67 |
| PP_0500 | dTDP-4-rhamnose reductase-related protein | 1.55 |
| PP_3231 | Uncharacterized protein | 1.18 |
| PP_5002 | Uncharacterized protein | 1.06 |
| PP_1078 | Putative ABC transporter, ATP-binding protein | 1.89 |
| PP_4674 | RecBCD enzyme subunit RecC | 1.28 |
| PP_1516 | RND membrane fusion protein | 1.16 |
| PP_3596 | D-lysine oxidase AmaD | 1.16 |
| PP_3795 | Uncharacterized protein | 1.55 |
| PP_4334 | ParA family protein | 1.64 |
| PP_4761 | Hydrolase, haloacid dehalogenase-like family | 2.11 |
| PP_1695 | Putative Sodium-solute symporter/sensory box histidine kinase/response regulator | 2.93 |
| PP_2912 | Uncharacterized protein | 1.94 |
| PP_3254 | Putative Nucleosidase | 1.35 |
| PP_3067 | Uncharacterized protein | 1.24 |
| PP_2443 | Serine/threonine transporter SstT | 1.22 |
| PP_2836 | Putative 2-keto-3-deoxyxylonate dehydratase | 2.44 |
| PP_2198 | Aldose sugar dehydrogenase YliI | 1.52 |
| PP_0495 | Type 1 L-asparaginase AnsA | 1.03 |
| PP_4171 | Uncharacterized protein | 1.11 |
| PP_0136 | Uncharacterized protein | 1.13 |
| PP_0976 | Ribosomal RNA large subunit methyltransferase RlmF | 1.23 |
| PP_5101 | Coproporphyrinogen/heterocyclic compound oxidase (Aerobic) yggW | 1.72 |
| PP_2005 | Uncharacterized protein | 1.31 |
| PP_0861 | Outer membrane ferric siderophore receptor | 4.30 |
| PP_3367 | Uncharacterized protein | 1.59 |
| PP_3811 | Transcriptional regulator, LysR family | 2.22 |
| PP_3116 | LexA repressor 2 | 2.18 |
| PP_2891 | Acetyltransferase, GNAT family | 1.41 |
| PP_3364 | Response regulator | 1.29 |
| PP_3563 | Uncharacterized protein | 1.28 |
| PP_3191 | Putative threonine ammonia-lyase/dehydratase | 2.49 |
| PP_0008 | Ribonuclease P protein component RnpA | 1.17 |
| PP_0619 | Branched-chain amino acid ABC transporter, periplasmic amino acid-binding protein | 1.72 |
| PP_3671 | Oxidoreductase, aldo/keto reductase family | 1.04 |
| PP_3421 | Sensor histidine kinase | 1.21 |
| PP_0076 | Putative choline betaine-binding protein | 1.25 |
| PP_5133 | Uncharacterized protein | 1.36 |
| PP_1105 | Putative DNA ligase, ATP-dependent | 1.10 |
| PP_4336 | Flagellar motor rotation protein | 1.08 |
| PP_0936 | Maf-like protein PP_0936 Maf-1 | 1.50 |
| PP_4831 | Cobalt-precorrin-5B C(1)-methyltransferase | 1.39 |
| PP_4738 | Uncharacterized protein | 1.46 |
| PP_4683 | Penicillin-binding protein 1B | 1.12 |
| PP_0238 | Alkanesulfonate monooxygenase | 2.91 |
| PP_1881 | Uncharacterized protein | 1.34 |
| PP_5464 | Uncharacterized protein | 1.04 |
| PP_1028 | Transcriptional regulator, LysR family | 1.05 |
| PP_0350 | Outer membrane ferrichrome-iron receptor | 1.33 |
| PP_3757 | Chemotaxis protein CheY | 1.47 |
| PP_5221 | UPF0178 protein PP_5221 | 1.28 |
| PP_1788 | Uncharacterized protein | 1.03 |
| PP_4109 | Uncharacterized protein | 3.34 |
| PP_4405 | Sensory box protein | 1.23 |
| PP_0561 | Thiol: disulfide interchange protein DsbD | 1.16 |
| PP_2682 | Fe-containing alcohol dehydrogenase YiaY | 1.45 |
| PP_3985 | Transposase | 1.75 |
| PP_2052 | Putative bifunctional enzyme: sugar-phosphatase/mannitol-1-phosphate 5-dehydrogenase | 1.26 |
| PP_5169 | Sulfate ABC transporter, inner membrane subunit CysW | 1.80 |
| PP_1824 | Smr domain protein | 2.02 |
| PP_4622 | Hmg transcriptional repressor | 1.54 |
| PP_0224 | Monooxygenase, DszC family | 4.07 |
| PP_3387 | Uncharacterized protein | 2.09 |
| PP_0563 | Response regulator | 2.07 |
| PP_5308 | Protein TonB | 1.76 |
| PP_2727 | Putative C-factor | 1.26 |
| PP_0180 | Putative cytochrome c family protein | 1.16 |
| PP_4555 | Uncharacterized protein | 1.85 |
| PP_2495 | Uncharacterized protein | 2.05 |
| PP_2578 | Uncharacterized protein | 1.45 |
| PP_4584 | Putative endonuclease YajD | 1.10 |
| PP_1921 | Uncharacterized protein | 1.14 |
| PP_0868 | ABC transporter ATP-binding subunit | 2.32 |

TABLE 12-continued

Proteins more highly expressed in LJ014 relative to KT2440 when treated with 0.05% FPF (V/V).

| Protein | Description | N. Log$_2$ |
|---|---|---|
| PP_2540 | Oxidoreductase, short-chain dehydrogenase/reductase family | 1.25 |
| PP_3510 | Uncharacterized protein | 1.37 |
| PP_4333 | CheW domain protein | 1.22 |
| PP_4855 | Osmotically-inducible lipoprotein OsmE | 1.43 |
| PP_1424 | Uncharacterized protein PP_1424 | 1.00 |
| PP_5140 | Transcriptional regulator, MerR family | 1.29 |
| PP_2566 | Uncharacterized protein | 1.74 |
| PP_3810 | Uncharacterized protein | 1.40 |
| PP_2877 | Putative osmotic pressure-regulated transporter YyfeH | 1.27 |
| PP_4032 | Putative Outer membrane lipoprotein Blc | 2.89 |
| PP_1350 | Sensory box histidine kinase/response regulator | 4.26 |
| PP_3142 | Putative Sugar transferase | 1.70 |
| PP_4294 | Conserved inner membrane protein YyedI | 2.14 |
| PP_0944 | Fumarate hydratase class II FumC-I | 1.14 |
| PP_1005 | Heme oxygenase HemO | 1.26 |
| PP_5659 | Uncharacterized protein | 1.24 |
| PP_3753 | Transcriptional regulator, AraC family | 2.14 |

Example 15

Bioconversion of Waste Streams with Chaperone-Expressing Strains

Figures 17A, 17B, 17C, 17D, 17E:
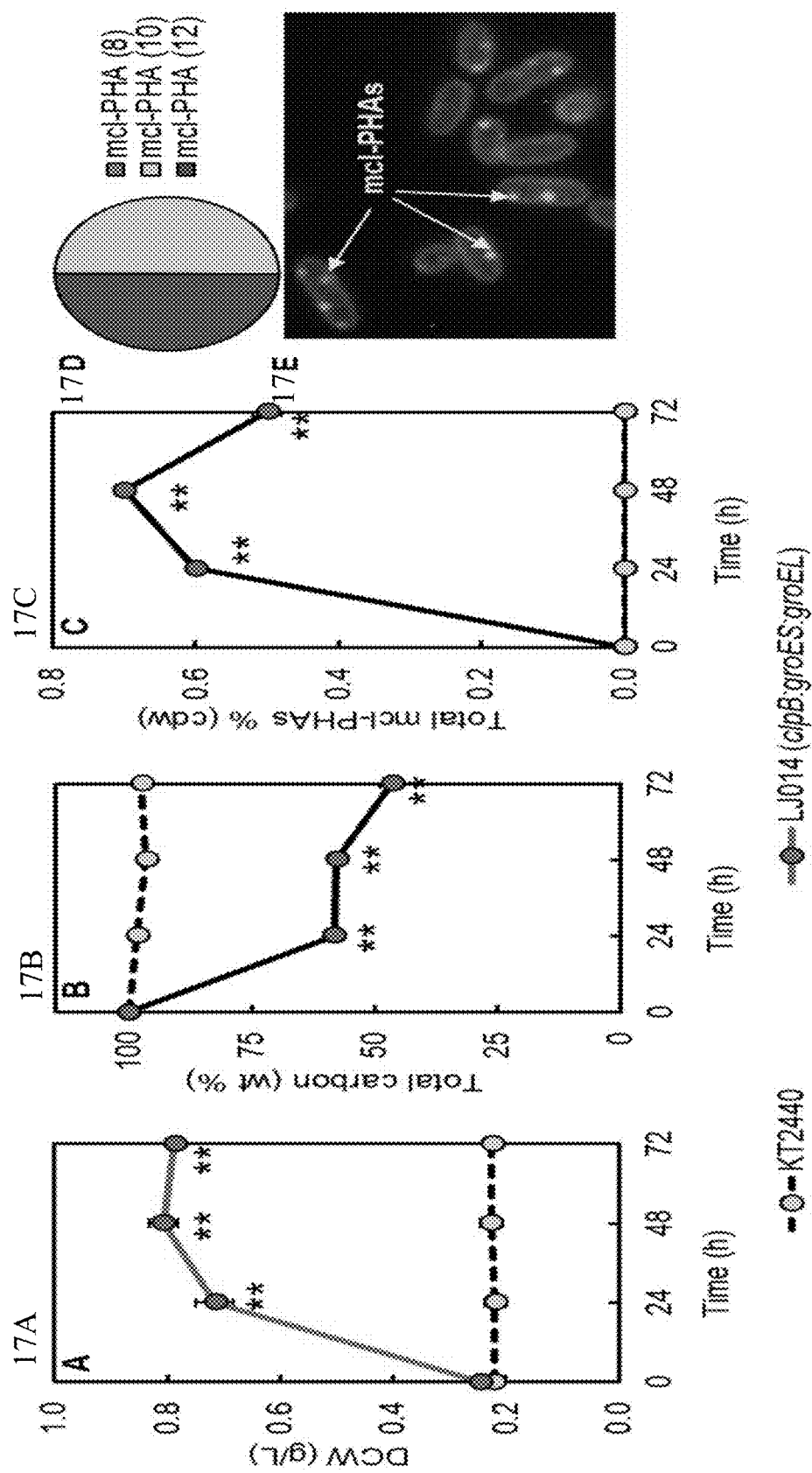
FIG. 17 depicts graphs that show the use of waste carbon in a FPF stream for growth, energy and mcl-PHA production by a chaperone overexpressing non-naturally occurring *P. putida* strain.
Figures 18A, 18B:
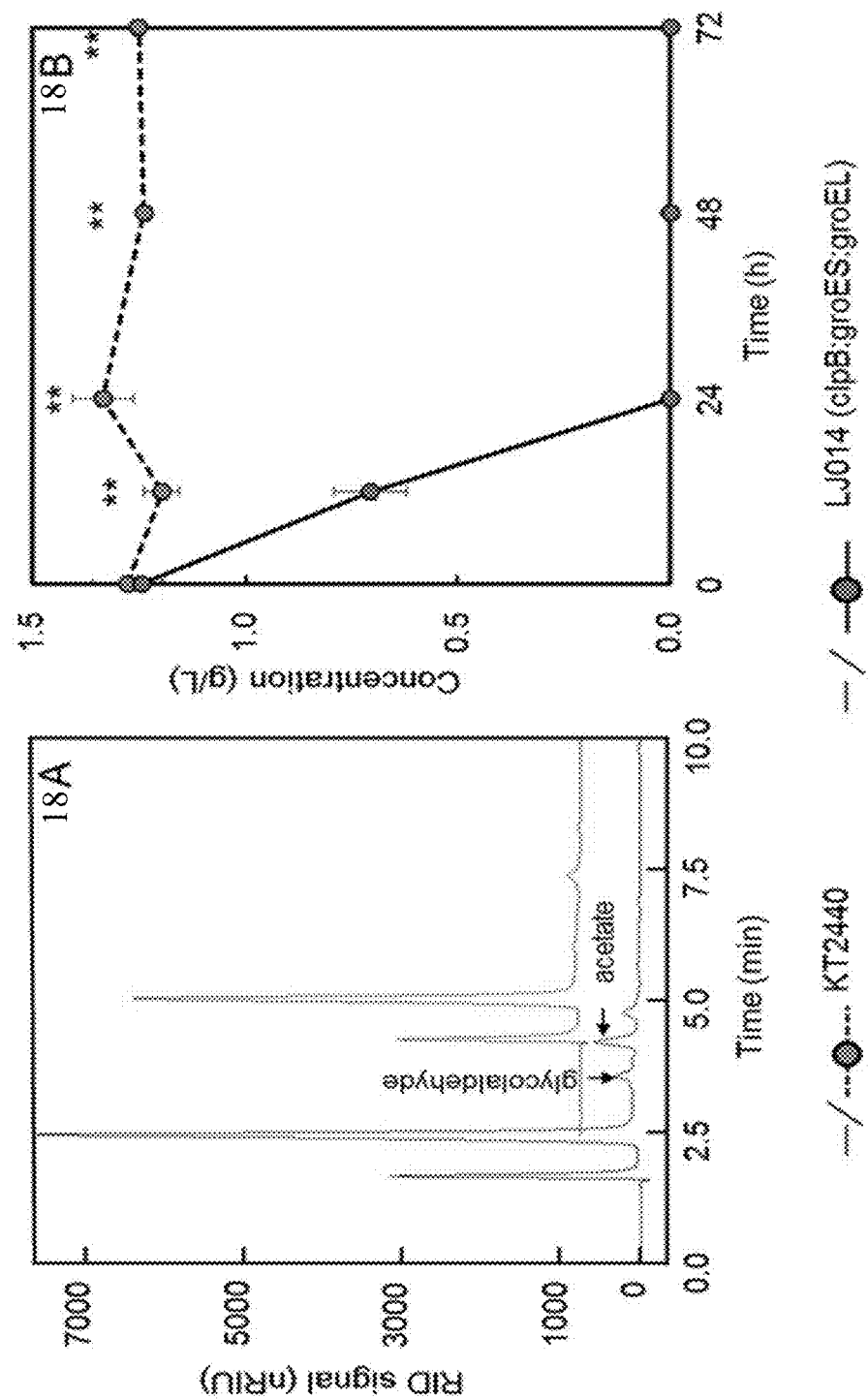
FIG. 18 depicts the consumption of acetate in FPF by the LJ014 strain.

The non-naturally occurring, engineered LJ014 strain was tested to determine if it could use FPF as a sole carbon and energy source. The LJ014 strain was grown in 50 mL of M9 medium containing 1% FPF (v/v), which is equivalent to 3.44 g/L of organic carbon as a sole carbon source in a shake flask. The LJ014 cells survived and grew using FPF carbon, but the KT2440 strain did not (see FIG. 17A). HPLC analysis showed that acetate and GA are the major carbon components consumed within 24 hours by LJ014 (see FIG. 18). LJ014 used 52.27±1.12% of total carbon in FPF by the end of the cultivation at 72 hours, while KT2440 was unable to use carbon in FPF (see FIG. 17B). Native P. putida KT2440 metabolism theoretically allows complete conversion of 45.25% (e.g. acetic, formic, propionic, vanillin, and catechol) of carbon present in FPF for growth and energy and partial metabolism of 18.62% (e.g. glycolaldehyde, furfural, 5-HMF). Thus, LJ014 converted approximately 82% of theoretically accessible carbon in the FPF medium within 72 hours (see Table 6).

The capability of the LJ014 strain to convert FPF waste-carbon into the native carbon storage product for P. putida, namely medium-chain-length polyhydroxyalkanoates (mcl-PHAs) was tested. The cells were grown in nitrogen-limited M9 medium supplemented with 1% (v/v) FPF to induce mcl-PHA production. mcl-PHA accumulation was observed microscopically (see FIG. 17E), and quantitative analysis revealed that the LJ014 strain accumulated mcl-PHAs around 0.7% of dry cell weight (see FIG. 17C), which accounted for a yield of 0.42±0.04 g mcl-PHAs per liter of FPF. As expected in P. putida KT2440, the mcl-PHA profiles are mainly of chain lengths 10 and 12, with some 8-carbon chain-length mcl-PHA detected in the samples, but below the quantification range (see FIG. 17D). Based on the growth and carbon analysis, these results show that expression of groES, groEL, and clpB enabled P. putida to metabolize available carbon by partially overcoming the FPF stream toxicity.

Example 16

Improved Tolerance of Chaperone-Expressing Strains

Figures 19A, 19B:
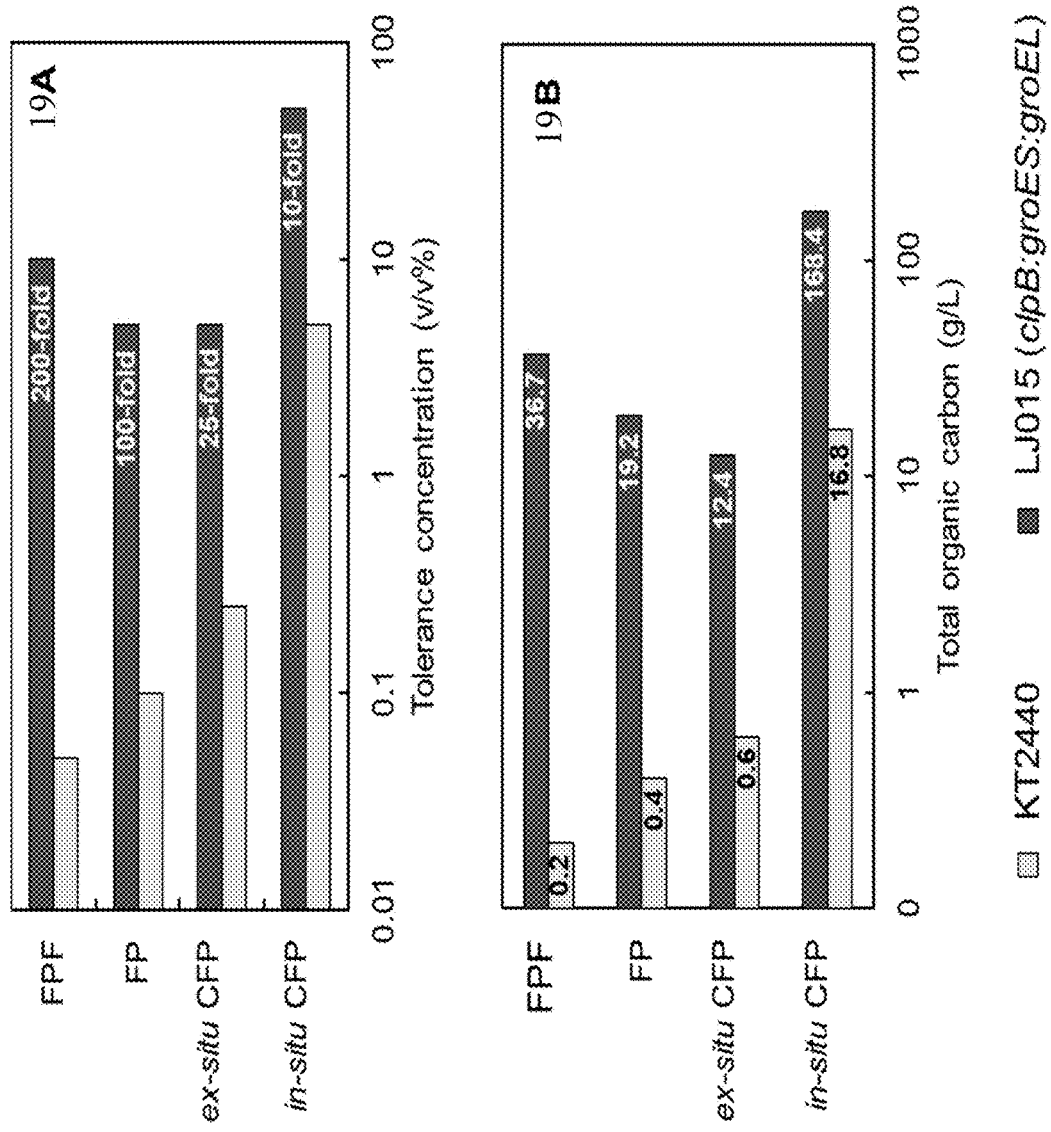
FIG. 19 depicts tolerance thresholds of a chaperone-overexpressing *P. putida* strain to different TC wastewater streams.

Given that the chaperone-dependent machinery requires significant ATP to function, the P. putida EM42 strain, which is a reduced-genome strain derived from P. putida KT2440, could provide further tolerance improvements, as it exhibits a higher ATP level relative to the wild-type KT2440 strain. Of note, the EC$_{50}$ value of FPF on the wild-type EM42 strain is 0.1% (v/v), a 2-fold tolerance improvement over the parental KT2440 strain. Thus, the LJ015 strain was developed by integrating an extra copy of tac promoter-driven chaperone genes clpB, groES, and groEL into the P. putida EM42 genome rather than the KT2440 genome as with LJ014. The LJ015 strain substantially improved the cell survival and colony forming capability under FPF stress (see FIG. 20). The maximum tolerable FPF concentration of the LJ014 and LJ015 strains are 2.5% and 10% (v/v), respectively. Thus, the LJ015 exhibits 4-fold tolerance improvement over the LJ014 strain to FPF, and the overall tolerance of the LJ015 strain to FPF is improved by 200-fold relative to the KT2440 strain (see FIG. 19).

The FPF stream represents only one pyrolysis-derived wastewater stream, and the waste stream composition depends significantly on the upstream process configuration. To determine the general applicability of this chaperone overexpression strategy, the LJ015 strain tolerance in TC waste streams from FP, ex-situ CPF, and in-situ CFP was evaluated. LJ015 exhibits substantially higher cell survival than KT2440, with colony-forming units up by 5% (v/v) FP, 50% (v/v) in-situ CFP, and 5% (v/v) ex-situ CFP in M9 medium (see FIG. 20). These results account for the remarkable tolerance improvements of the LJ015 strain to TC wastewater streams (see FIG. 19A). Thus, the LJ015 strain can access greater than about 12 g/L of carbon in all classes of TC wastewater streams, an industrially-relevant range of carbon that could be used in a fed-batch cultivation process for valorizing these waste carbon streams, which would otherwise be impossible with the wild-type P. putida strain (see FIG. 19B). The LJ015 strain is thus a base or chassis strain for transforming process-specific TC wastewater streams.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A non-naturally occurring *Pseudomonas* cell that is capable of metabolizing at least 82% of the available carbon within 72 hours in a waste stream resulting from the pyrolysis of biomass wherein the *Pseudomonas* cell overexpresses active chaperone enzymes selected from the group consisting of GroES, GroEL and ClpB wherein the gene encoding for ClpB is operably linked to a tac promoter and has a nucleotide sequence that is greater than 85% identity to SEQ ID NO: 1 and encodes for an active ClpB enzyme having an amino acid sequence that is greater than 90% identity to SEQ ID NO: 2; and wherein the gene encoding for GroES is operably linked to a tac promoter and has a nucleotide sequence that is greater than 85% identity to SEQ ID NO: 3 and encodes for an active GroES enzyme having an amino acid sequence that is greater than 90% identity to SEQ ID NO: 4; and wherein the gene encoding for GroEL is operably linked to a tac promoter and has a nucleotide sequence that is greater than 85% identity to SEQ ID NO: 5 and encodes for an active GroEL enzyme having an amino acid sequence that is greater than 90% identity to SEQ ID NO: 6.

2. The cell of claim 1 wherein the genes are incorporated into the genome of the *Pseudomonas* cell.

3. The cell of claim 1 capable of an 83 fold or greater survival rate in comparison to the naturally occurring *Pseudomonas* from which it is derived after 12 hours of growth in a waste stream from the pyrolysis of biomass.

4. The cell of claim 1 able to grow in waste stream solutions containing concentrations of compounds that do not allow for the growth of the naturally occurring *Pseudomonas* from which it is derived from; the concentrations of compounds selected from the group consisting of greater than 7.5 times the concentration of aldehydes, 1.5 times the concentration of ketones, 3.5 times the concentration of acids, 3.5 times the concentration of phenolics, and 1.5 times the concentration of alcohols.

5. A method for metabolizing waste stream products from the pyrolysis of biomass comprising treating the waste stream products with the *Pseudomonas* cell of claim 1.

* * * * *

SEQUENCE LISTING

```
<160> NUMBER OF SEQ ID NOS: 8

<210> SEQ ID NO 1
<211> LENGTH: 2562
<212> TYPE: DNA
```

<213> ORGANISM: Pseudomonas putida

<400> SEQUENCE: 1

```
atgcgaatag accgtttaac cagcaagctg caacttgcaa tatccgatgc ccagtctttg      60
gccgttggca tggaccaccc tgccatcgag cccgtgcacc tgttacaggc gctgctcgaa     120
cagcagggcg gctccatcaa accgctgctg atgcaggtag gcttcgacat caatggcctg     180
cgccaggggc tggtgaaaga gctcgaccaa ctgccgaaaa tacagaaccc taccggcgac     240
gtgaacatgt cgcaggactt ggcacgtctg cttaaccagg cagaccgcct ggcacagcag     300
aagggcgacc agttcatttc cagcgagctg gtgctgttgg ccgccatgga cgaaaacagc     360
aagctcggca agctgctgct gagccagggc gtgagcaaga aagcgctgga aaatgccatc     420
aacaacctgc gtggcggcgc ggcagtgaat gacgccaacg ccgaggaatc gcgccaggcg     480
ctggacaaat acaccgtcga cctgaccaag cgtgccgaag agggcaagct ggacccggtc     540
attggccgtg acgatgaaat ccgccgtacc gtgcaggtgc tgcaacgccg taccaagaac     600
aacccggtgc tgatcggtga gcctggcgtg ggtaaaaccg ccatcgccga aggcctggcc     660
cagcgcatca tcaatggtga agtgcccgac ggcctcaaag gcaagcgcct gttggcgctg     720
gacatgggcg cgctaattgc cggtgccaag taccgcggtg agttcgaaga gcgcttgaaa     780
agcctgctga cgaactgtc caagcaggaa ggccagatca tcctgttcat cgacgaactg     840
cacaccatgt tcggcgccgg caaggcgag gcgccatgg acgccggcaa catgctcaag     900
ccggccctgg cccgcggcga gctgcattgc gtaggtgcca ccacgctgaa cgagtaccgc     960
cagttcatcg aaaaggacgc cgccctggag cgccgtttcc agaaggtgct ggtcgaggag    1020
ccgagcgagg aagacaccat cgccatcctg cgtggcctga agagcgcta tgaagtgcac    1080
cacaaggtgg ccatcaccga cggtgcaatc atcgctgcgg ccaagctcag ccatcgctac    1140
atcaccgacc gccagctgcc ggacaaggcc attgacctga tcgacgaagc ggccagccgc    1200
atccgcatgg agatcgactc caagccgaa gtgctcgacc gccttgatcg ccgcctgatc    1260
cagctgaagg tggagtcgca ggcgctgaag aaagaagaag acgaagcggc gaaaaagcgc    1320
ctggagaagc tgaccgagga aatcgagcgg ctggagcgtg agtattccga cctggaagaa    1380
atctgggctt cggagaaagc tgaagtgcag ggctcggcgc agatccagca aagatcgag    1440
cagtctcgcc aggagctgga agccgcccgt cgcaaaggcg acctgaaccg catggccgaa    1500
ctgcagtacg gggtgatccc ggacctggag cgcagcctgc agatggtcga ccagcacggc    1560
aagaccgaca accagttgct gcgcaacaag gtcaccgagg aagaaattgc cgaagtggta    1620
tcgaaatgga ccggcattcc tgtggccaag atgctcgaag gcgagcgtga agctgctg    1680
aagatggaag agctgctgca ccagcgcgtg attggccaga gcgaggcggt aaccgccgta    1740
gccaacgccg tacgccgctc gcgtgccggg ctgtccgacc gaaccggcc aagtggttcg    1800
ttcctgttcc tcggcccgac cggtgtgggc aagaccgaac tgtgcaaggc gctggccgag    1860
ttcctgttcg acaccgaaga ggcgatggtg cgcatcgaca tgtccgaatt catggagaag    1920
cactccgtcg cgcgcctgat cggtgcacca ccaggctatg tagggtatga agagggcggt    1980
tacctgaccg aggccgtgcg cgcgcaagcct tactcggtgg tgctgctgga cgaggtggaa    2040
aaagcccacc cggatgtgtt caacgtgctg ttgcaggtgc tggaagacgg ccgcctgacc    2100
gacagccacg gcgcaccgt ggacttccgc aacaccgtga tcgtgatgac ctccaacctg    2160
ggctcggcgc agattcagga actggtgggt gaccgcgagg cacagcgtgc ggcagtgatg    2220
gatgcggtgg gggcgcactt ccgtccggaa ttcatcaacc gcatcgacga agtggtggtg    2280
```

```
ttcgagcctt tgggccgcga gcagattgcc ggtattacag aaatccagct cggccgcctg    2340
cgcagccgcc tgctggagcg cgaactgtcg ttgagcctga gcccagaggc gttggacaag    2400
ctgattgccg tgggttatga cccggtgtac ggcgcgcggc cgctgaagcg tgcgatccag    2460
cgctggatcg agaacccgct ggcgcagctg attctggccg gcaagttcct gcccggtacg    2520
gcgatcaccg ccaaggtgga aggcgacgaa atcgtctttg gc                      2562
```

<210> SEQ ID NO 2
<211> LENGTH: 854
<212> TYPE: PRT
<213> ORGANISM: Pseudomonas putida

<400> SEQUENCE: 2

```
Met Arg Ile Asp Arg Leu Thr Ser Lys Leu Gln Leu Ala Ile Ser Asp
1               5                   10                  15

Ala Gln Ser Leu Ala Val Gly Met Asp His Pro Ala Ile Glu Pro Val
            20                  25                  30

His Leu Leu Gln Ala Leu Leu Glu Gln Gln Gly Gly Ser Ile Lys Pro
        35                  40                  45

Leu Leu Met Gln Val Gly Phe Asp Ile Asn Gly Leu Arg Gln Gly Leu
    50                  55                  60

Val Lys Glu Leu Asp Gln Leu Pro Lys Ile Gln Asn Pro Thr Gly Asp
65                  70                  75                  80

Val Asn Met Ser Gln Asp Leu Ala Arg Leu Leu Asn Gln Ala Asp Arg
                85                  90                  95

Leu Ala Gln Gln Lys Gly Asp Gln Phe Ile Ser Ser Glu Leu Val Leu
            100                 105                 110

Leu Ala Ala Met Asp Glu Asn Ser Lys Leu Gly Lys Leu Leu Leu Ser
        115                 120                 125

Gln Gly Val Ser Lys Lys Ala Leu Glu Asn Ala Ile Asn Asn Leu Arg
    130                 135                 140

Gly Gly Ala Ala Val Asn Asp Ala Asn Ala Glu Glu Ser Arg Gln Ala
145                 150                 155                 160

Leu Asp Lys Tyr Thr Val Asp Leu Thr Lys Arg Ala Glu Glu Gly Lys
                165                 170                 175

Leu Asp Pro Val Ile Gly Arg Asp Asp Glu Ile Arg Arg Thr Val Gln
            180                 185                 190

Val Leu Gln Arg Arg Thr Lys Asn Asn Pro Val Leu Ile Gly Glu Pro
        195                 200                 205

Gly Val Gly Lys Thr Ala Ile Ala Glu Gly Leu Ala Gln Arg Ile Ile
    210                 215                 220

Asn Gly Glu Val Pro Asp Gly Leu Lys Gly Lys Arg Leu Leu Ala Leu
225                 230                 235                 240

Asp Met Gly Ala Leu Ile Ala Gly Ala Lys Tyr Arg Gly Glu Phe Glu
                245                 250                 255

Glu Arg Leu Lys Ser Leu Leu Asn Glu Leu Ser Lys Gln Glu Gly Gln
            260                 265                 270

Ile Ile Leu Phe Ile Asp Glu Leu His Thr Met Val Gly Ala Gly Lys
        275                 280                 285

Gly Glu Gly Ala Met Asp Ala Gly Asn Met Leu Lys Pro Ala Leu Ala
    290                 295                 300

Arg Gly Glu Leu His Cys Val Gly Ala Thr Thr Leu Asn Glu Tyr Arg
305                 310                 315                 320
```

-continued

```
Gln Phe Ile Glu Lys Asp Ala Ala Leu Glu Arg Arg Phe Gln Lys Val
                325                 330                 335

Leu Val Glu Glu Pro Ser Glu Asp Thr Ile Ala Ile Leu Arg Gly
            340                 345                 350

Leu Lys Glu Arg Tyr Glu Val His His Lys Val Ala Ile Thr Asp Gly
            355                 360                 365

Ala Ile Ile Ala Ala Ala Lys Leu Ser His Arg Tyr Ile Thr Asp Arg
        370                 375                 380

Gln Leu Pro Asp Lys Ala Ile Asp Leu Ile Glu Ala Ala Ser Arg
385                 390                 395                 400

Ile Arg Met Glu Ile Asp Ser Lys Pro Glu Val Leu Asp Arg Leu Asp
                405                 410                 415

Arg Arg Leu Ile Gln Leu Lys Val Glu Ser Gln Ala Leu Lys Lys Glu
            420                 425                 430

Glu Asp Glu Ala Ala Lys Lys Arg Leu Glu Lys Leu Thr Glu Glu Ile
        435                 440                 445

Glu Arg Leu Glu Arg Glu Tyr Ser Asp Leu Glu Glu Ile Trp Ala Ser
            450                 455                 460

Glu Lys Ala Glu Val Gln Gly Ser Ala Gln Ile Gln Gln Lys Ile Glu
465                 470                 475                 480

Gln Ser Arg Gln Glu Leu Glu Ala Ala Arg Arg Lys Gly Asp Leu Asn
                485                 490                 495

Arg Met Ala Glu Leu Gln Tyr Gly Val Ile Pro Asp Leu Glu Arg Ser
            500                 505                 510

Leu Gln Met Val Asp Gln His Gly Lys Thr Asp Asn Gln Leu Leu Arg
        515                 520                 525

Asn Lys Val Thr Glu Glu Ile Ala Glu Val Val Ser Lys Trp Thr
530                 535                 540

Gly Ile Pro Val Ala Lys Met Leu Glu Gly Glu Arg Glu Lys Leu Leu
545                 550                 555                 560

Lys Met Glu Glu Leu Leu His Gln Arg Val Ile Gly Gln Ser Glu Ala
                565                 570                 575

Val Thr Ala Val Ala Asn Ala Val Arg Arg Ser Arg Ala Gly Leu Ser
            580                 585                 590

Asp Pro Asn Arg Pro Ser Gly Ser Phe Leu Phe Leu Gly Pro Thr Gly
            595                 600                 605

Val Gly Lys Thr Glu Leu Cys Lys Ala Leu Ala Glu Phe Leu Phe Asp
        610                 615                 620

Thr Glu Glu Ala Met Val Arg Ile Asp Met Ser Glu Phe Met Glu Lys
625                 630                 635                 640

His Ser Val Ala Arg Leu Ile Gly Ala Pro Pro Gly Tyr Val Gly Tyr
                645                 650                 655

Glu Glu Gly Gly Tyr Leu Thr Glu Ala Val Arg Arg Lys Pro Tyr Ser
            660                 665                 670

Val Val Leu Leu Asp Glu Val Glu Lys Ala His Pro Asp Val Phe Asn
        675                 680                 685

Val Leu Leu Gln Val Leu Glu Asp Gly Arg Leu Thr Asp Ser His Gly
        690                 695                 700

Arg Thr Val Asp Phe Arg Asn Thr Val Ile Val Met Thr Ser Asn Leu
705                 710                 715                 720

Gly Ser Ala Gln Ile Gln Glu Leu Val Gly Asp Arg Glu Ala Gln Arg
                725                 730                 735

Ala Ala Val Met Asp Ala Val Gly Ala His Phe Arg Pro Glu Phe Ile
```

```
                    740                 745                 750
Asn Arg Ile Asp Glu Val Val Phe Glu Pro Leu Gly Arg Glu Gln
            755                 760                 765
Ile Ala Gly Ile Thr Glu Ile Gln Leu Gly Arg Leu Arg Ser Arg Leu
        770                 775                 780
Leu Glu Arg Glu Leu Ser Leu Ser Leu Ser Pro Glu Ala Leu Asp Lys
785                 790                 795                 800
Leu Ile Ala Val Gly Tyr Asp Pro Val Tyr Gly Ala Arg Pro Leu Lys
                805                 810                 815
Arg Ala Ile Gln Arg Trp Ile Glu Asn Pro Leu Ala Gln Leu Ile Leu
            820                 825                 830
Ala Gly Lys Phe Leu Pro Gly Thr Ala Ile Thr Ala Lys Val Glu Gly
        835                 840                 845
Asp Glu Ile Val Phe Gly
    850

<210> SEQ ID NO 3
<211> LENGTH: 321
<212> TYPE: DNA
<213> ORGANISM: Pseudomonas putida

<400> SEQUENCE: 3
atgaaaacca caatttggga gagatcgaca atgaaacttc gtcctctgca tgaccgcgta      60
gtcatccgtc gcagcgaaga agaatcgaaa accgctggcg gtatcgtcct gccgggttcg     120
gccgctgaaa aaccaaaccg cggcgaagtt gtagccgtcg gcaccggtcg cgtcctggac     180
aacggcgaag ttcgcgcgct ggccgtgaaa gtgggtgaca aagtggtttt cggcccgtac     240
tcgggcagca acaccgtgaa agtcgatggc gaagacctgc tggtcatggc cgagaacgaa     300
atcctcgccg ttgtcgaagg c                                              321

<210> SEQ ID NO 4
<211> LENGTH: 107
<212> TYPE: PRT
<213> ORGANISM: Pseudomonas putida

<400> SEQUENCE: 4

Met Lys Thr Thr Ile Trp Glu Arg Ser Thr Met Lys Leu Arg Pro Leu
1               5                   10                  15
His Asp Arg Val Val Ile Arg Arg Ser Glu Glu Ser Lys Thr Ala
            20                  25                  30
Gly Gly Ile Val Leu Pro Gly Ser Ala Ala Glu Lys Pro Asn Arg Gly
        35                  40                  45
Glu Val Val Ala Val Gly Thr Gly Arg Val Leu Asp Asn Gly Glu Val
    50                  55                  60
Arg Ala Leu Ala Val Lys Val Gly Asp Lys Val Val Phe Gly Pro Tyr
65                  70                  75                  80
Ser Gly Ser Asn Thr Val Lys Val Asp Gly Glu Asp Leu Leu Val Met
                85                  90                  95
Ala Glu Asn Glu Ile Leu Ala Val Val Glu Gly
            100                 105

<210> SEQ ID NO 5
<211> LENGTH: 1638
<212> TYPE: DNA
<213> ORGANISM: Pseudomonas putida

<400> SEQUENCE: 5
```

```
atggctgcta agacgtaaa atttggtgat ccgctcgta agaaaatgct ggttggtgtc      60
aacgttctgg ctgacgcggt aaaagcgacc ctgggcccga aaggccgtaa cgtggtactg     120
gccaagagct tcggcgcgcc gaccatcacc aaggacggcg tttccgtcgc caagaaatc     180
gagctgaaag acgctttcga aacatgggc gcccagctgg tcaaggaagt tgcttccaag     240
gccaacgacg ctgccggtga cggcaccacc accgctaccg ttctggctca ggccatcgtc     300
aacgaaggcc tgaaagccgt cgctgccggc atgaacccga tggacctgaa cgcgggatc     360
gacaaggcca ctgctgccgt cgttgccgaa ctgaagaacc tgtccaagcc atgcgccgac     420
tccaaggcca tcgcccaggt aggtaccatc tctgccaact ccgacaactc catcggtgaa     480
atcatcgccg aagccatgga aaagtcggt aagaaggcg tgatcaccgt gaagaaggc      540
tcgggcctgg aaaacgaact gtccgtcgta aaggcatgc agttcgaccg cggctacctg     600
tcgccgtact cgtcaacaa gccggacacc atggttgccg agctggaagg cccgctgctg     660
ctgctggtcg acaagaaaat ctccaacatc cgtgagctgc tgccagttct ggaagccgtt     720
gccaaggccg ccgcccact gctgatcgtt gccgaagacg ttgaaggtga agcgctggct     780
accctggtag tcaacaacat gcgcggcatc gtcaaggttg ctgcagtcaa ggctccgggc     840
ttcggcgatc gccgcaaggc catgctgcag acatcgctg tcctgactgg cggccaggtc     900
atctccgaag aaatcggcct gtccctggaa accgctaccc tggagcacct gggtaacgcc     960
aagcgcgtca tcctgtccaa ggaaaacacc accatcatcg acggtgctgg cgctgacacc    1020
gagatcgaag cacgcgtcaa gcagatccgt gcccagatcg aagaaacttc ctcggactac    1080
gaccgtgaga gctgcaaga gcgtctggcc aagctggctg gcggtgttgc cgtgatcaag    1140
gtcggtgccg caccgaagt tgaaatgaaa gagaagaaag cccgcgttga agacgccctg    1200
cacgctaccc gtgcagccgt tgaagaaggc gtggtgcctg gcggtggtgt tgccctggtt    1260
cgcgccctgg cagccatcat cgacctgaaa ggcgacaacg aagaccagaa cgtcggtatc    1320
gcgctgctgc gtcgcgctgt tgaatccccg ctgcgccaga tcactgccaa cgccggtgat    1380
gagccaagcg tggttgctga aaggtcaag caaggttcgg caacttcgg ctacaacgcc     1440
gctaccggtg aatacggcga catgatcgag atgggtatcc tggacccagc caaggtcact    1500
cgctcggcgc tgcaagctgc tgcttcgatc ggcggtctga tgatcaccac cgaagccatg    1560
gttgccgacc tgccggaaga caagccagct gctggcatgc ctgatatggg tggcatgggt    1620
ggcatgggcg gcatgatg                                                   1638

<210> SEQ ID NO 6
<211> LENGTH: 546
<212> TYPE: PRT
<213> ORGANISM: Pseudomonas putida

<400> SEQUENCE: 6

Met Ala Ala Lys Asp Val Lys Phe Gly Asp Ser Ala Arg Lys Lys Met
1               5                   10                  15

Leu Val Gly Val Asn Val Leu Ala Asp Ala Val Lys Ala Thr Leu Gly
                20                  25                  30

Pro Lys Gly Arg Asn Val Val Leu Ala Lys Ser Phe Gly Ala Pro Thr
            35                  40                  45

Ile Thr Lys Asp Gly Val Ser Val Ala Lys Glu Ile Glu Leu Lys Asp
        50                  55                  60

Ala Phe Glu Asn Met Gly Ala Gln Leu Val Lys Glu Val Ala Ser Lys
65                  70                  75                  80
```

-continued

```
Ala Asn Asp Ala Ala Gly Asp Gly Thr Thr Thr Ala Thr Val Leu Ala
                85                  90                  95

Gln Ala Ile Val Asn Glu Gly Leu Lys Ala Val Ala Ala Gly Met Asn
            100                 105                 110

Pro Met Asp Leu Lys Arg Gly Ile Asp Lys Ala Thr Ala Ala Val Val
            115                 120                 125

Ala Glu Leu Lys Asn Leu Ser Lys Pro Cys Ala Asp Ser Lys Ala Ile
        130                 135                 140

Ala Gln Val Gly Thr Ile Ser Ala Asn Ser Asp Asn Ser Ile Gly Glu
145                 150                 155                 160

Ile Ile Ala Glu Ala Met Glu Lys Val Gly Lys Glu Gly Val Ile Thr
                165                 170                 175

Val Glu Glu Gly Ser Gly Leu Glu Asn Glu Leu Ser Val Val Glu Gly
            180                 185                 190

Met Gln Phe Asp Arg Gly Tyr Leu Ser Pro Tyr Phe Val Asn Lys Pro
        195                 200                 205

Asp Thr Met Val Ala Glu Leu Glu Gly Pro Leu Leu Leu Leu Val Asp
        210                 215                 220

Lys Lys Ile Ser Asn Ile Arg Glu Leu Leu Pro Val Leu Glu Ala Val
225                 230                 235                 240

Ala Lys Ala Gly Arg Pro Leu Leu Ile Val Ala Glu Asp Val Glu Gly
                245                 250                 255

Glu Ala Leu Ala Thr Leu Val Val Asn Asn Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Val Leu Thr Gly Gly Gln Val Ile Ser Glu Glu
        290                 295                 300

Ile Gly Leu Ser Leu Glu Thr Ala Thr Leu Glu His Leu Gly Asn Ala
305                 310                 315                 320

Lys Arg Val Ile Leu Ser Lys Glu Asn Thr Thr Ile Ile Asp Gly Ala
                325                 330                 335

Gly Ala Asp Thr Glu Ile Glu Ala Arg Val Lys Gln Ile Arg Ala Gln
            340                 345                 350

Ile Glu Glu Thr Ser Ser Asp Tyr Asp Arg Glu Lys Leu Gln Glu Arg
        355                 360                 365

Leu Ala Lys Leu Ala Gly Gly Val Ala Val Ile Lys Val Gly Ala Gly
        370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Pro Gly Gly Gly
                405                 410                 415

Val Ala Leu Val Arg Ala Leu Ala Ala Ile Ile Asp Leu Lys Gly Asp
            420                 425                 430

Asn Glu Asp Gln Asn Val Gly Ile Ala Leu Leu Arg Arg Ala Val Glu
        435                 440                 445

Ser Pro Leu Arg Gln Ile Thr Ala Asn Ala Gly Asp Glu Pro Ser Val
        450                 455                 460

Val Ala Asp Lys Val Lys Gln Gly Ser Gly Asn Phe Gly Tyr Asn Ala
465                 470                 475                 480

Ala Thr Gly Glu Tyr Gly Asp Met Ile Glu Met Gly Ile Leu Asp Pro
                485                 490                 495
```

```
Ala Lys Val Thr Arg Ser Ala Leu Gln Ala Ala Ser Ile Gly Gly
            500                 505                 510

Leu Met Ile Thr Thr Glu Ala Met Val Ala Asp Leu Pro Glu Asp Lys
        515                 520                 525

Pro Ala Ala Gly Met Pro Asp Met Gly Gly Met Gly Gly Met Gly Gly
        530                 535                 540

Met Met
545

<210> SEQ ID NO 7
<211> LENGTH: 10251
<212> TYPE: DNA
<213> ORGANISM: Artificial Sequence
<220> FEATURE:
<223> OTHER INFORMATION: pK18sB- PP_1584: Ptac-clpB-groES-groEL

<400> SEQUENCE: 7
ttgagatcct ttttttctgc gcgtaatctg ctgcttgcaa acaaaaaaac caccgctacc      60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttgtgat gctcgtcagg ggggcggagc ctatggaaaa acgcctcaca    600
caggaaacag ctatgacatg attacgaatt cgagctcggt accctcgagc cagacctacc    660
cagcgcccgc catgagcggg ctttttttcg cctggagtaa acccatgact gcacgcggta    720
tccgcaacaa caacccgggg aacatcgatt tcaatccacg caacgcctgg cagggtcagc    780
tcgggctgga ggtgggcgtg ggcaagccgc gtttcgcccg attcgaccaa gccgagaacg    840
gtatccgagc cctgggcaag ctgttgctca actaccgggg caaggatggg atgcctggcg    900
ttggtcggcc tggcatcgac actccgctgg agttcataaa ccgctgggca ccggcgagtg    960
agaacgacac caatgcctac gcgcaggcca ttgccaagcg cctaggcgtc ggcgtgcgtg   1020
actcgatcga catttccacg ccgcagatcc tgcgcgagtc ggtggtgggc atcatcgtgc   1080
atgagaacgg cggtaacccg tatccgtccg cgctgatcga tgagggcatc aggcgggccc   1140
tggcatgagc ccttgggttg gcttagcggc tgccgtggtc ctggtggcca gccactgggg   1200
cgcctacgag cacggccgga gtgtagaaca ggcgcaggct ggccaagtgt cggccaagcg   1260
cgatagcggc gaccgtcttg ccgaggttat cggtgagcgc ggcgcccgtc agcaggaaca   1320
tcaacgcgcc caggcgcagg aggaggcgag ggtccatggt catgaagaaa gatcgattgc   1380
gagtgctggc gctgatggtg ccgatgctgc tggccagcgg ctgcgcgacg aaggcgccaa   1440
gctcgccgcc gccgtcagtt gccccggcgc ggataccgcc gctgtcgccc gaggccaggc   1500
agccacccgc gccgccatgg tgctctccga cctgctcaca cggtctgtcg aaacgaatcg   1560
agagctggcg aaggcttatg accaatcccg aatagcaggg gagcagtgcc ggcgagagta   1620
cgatgcgctt ctgccatccg gctgagttgg attgctcggc gccggttgtt atgagtagga   1680
tactgttttt atatacagta atggtgagct atggccatcc tactccctcc agcgtgggtc   1740
```

```
gctgaacttg atgatcgttt tgcgctggtg accgatccgg acggccgctc ggctgtgctg    1800
gcagagatgg cgaaggcggc tcaccgccgg cgggagatcg acgcaaaaaa ccgcacccag    1860
gtgcggtttt ttgaattcga gctgttgaca attaatcatc ggctcgtata atgtgtggaa    1920
ttgtgagcgg ataacaattt cacacttccg acctgccctt aaaggaagg tacaccatgc     1980 gaatagaccg tttaaccagc aagctgcaac ttgcaatatc cgatgcccag tctttggccg    2040
ttggcatgga ccaccctgcc atcgagcccg tgcacctgtt acaggcgctg ctcgaacagc    2100
agggcggctc catcaaaccg ctgctgatgc aggtaggctt cgacatcaat ggcctgcgcc    2160
aggggctggt gaaagagctc gaccaactgc cgaaaataca gaaccctacc ggcgacgtga    2220
acatgtcgca ggacttggca cgtctgctta accaggcaga ccgcctggca cagcagaagg    2280
gcgaccagtt catttccagc gagctggtgc tgttggccgc catggacgaa acagcaagc    2340 tcggcaagct gctgctgagc cagggcgtga gcaagaaagc gctggaaaat gccatcaaca    2400
acctgcgtgg cggcgcggca gtgaatgacg ccaacgccga ggaatcgcgc caggcgctgg    2460
acaaatacac cgtcgacctg accaagcgtg ccgaagaggg caagctggac ccggtcattg    2520
gccgtgacga tgaaatccgc cgtaccgtgc aggtgctgca acgccgtacc aagaacaacc    2580
cggtgctgat cggtgagcct ggcgtgggta aaaccgccat cgccgaaggc ctggcccagc    2640
gcatcatcaa tggtgaagtg cccgacggcc tcaaaggcaa gcgcctgttg cgctggaca    2700 tgggcgcgct aattgccggt gccaagtacc gcggtgagtt cgaagagcgc ttgaaaagcc    2760
tgctgaacga actgtccaag caggaaggcc agatcatcct gttcatcgac gaactgcaca    2820
ccatggtcgg cgccggcaaa ggcgagggcg ccatggacgc cggcaacatg ctcaagccgg    2880
ccctggcccg cggcgagctg cattgcgtag tgccaccac gctgaacgag taccgccagt    2940
tcatcgaaaa ggacgccgcc ctggacgcc gttttccagaa ggtgctggtc gaggagccga    3000
gcgaggaaga caccatcgcc atcctgcgtg gcctgaaaga gcgctatgaa gtgcaccaca    3060
aggtggccat caccgacggt gcaatcatcg ctgcggccaa gctcagccat cgctacatca    3120
ccgaccgcca gctgccggac aaggccattg acctgatcga cgaagcggcc agccgcatcc    3180
gcatggagat cgactccaag ccggaagtgc tcgaccgcct tgatcgccgc ctgatccagc    3240
tgaaggtgga gtcgcaggcg ctgaagaaag aagaagacga agcggcgaaa aagcgcctgg    3300
agaagctgac cgaggaaatc gagcggctgg agcgtgagta ttccgacctg aagaaatct     3360 gggcttcgga gaaagctgaa gtgcagggct cggcgcagat ccagcaaaag atcgagcagt    3420
ctcgccagga gctggaagcc gcccgtcgca aaggcgacct gaaccgcatg ccgaactgc     3480 agtacggggt gatcccggac ctggagcgca gcctgcagat ggtcgaccag cacggcaaga    3540
ccgacaacca gttgctgcgc aacaaggtca ccgaggaaga aattgccgaa gtggtatcga    3600
aatggaccgg cattcctgtg gccaagatgc tcgaaggcga gcgtgagaag ctgctgaaga    3660
tggaagagct gctgcaccag cgcgtgattg gccagagcga ggcggtaacc gccgtagcca    3720
acgccgtacg ccgctcgcgt gccgggctgt ccgacccgaa ccggccaagt ggttcgttcc    3780
tgttcctcgg cccgaccggt gtgggcaaga ccgaactgtg caaggcgctg gccgagttcc    3840
tgttcgacac cgaagaggcg atggtgcgca tcgacatgtc cgaattcatg gagaagcact    3900
ccgtcgcgcg cctgatcggt gcaccaccag gctatgtagg gtatgaagag ggcggttacc    3960
tgaccgaggc cgtgcggcgc aagccttact cggtggtgct gctggacgag gtggaaaaag    4020
cccacccgga tgtgttcaac gtgctgttgc aggtgctgga agacggccgc ctgaccgaca    4080
```

```
gccacgggcg caccgtggac ttccgcaaca ccgtgatcgt gatgacctcc aacctgggct    4140
cggcgcagat tcaggaactg gtgggtgacc gcgaggcaca gcgtgcggca gtgatggatg    4200
cggtgggggc gcacttccgt ccggaattca tcaaccgcat cgacgaagtg gtggtgttcg    4260
agcctttggg ccgcgagcag attgccggta ttacagaaat ccagctcggc cgcctgcgca    4320
gccgcctgct ggagcgcgaa ctgtcgttga gcctgagccc agaggcgttg acaagctga    4380 ttgccgtggg ttatgacccg gtgtacggcg cgcggccgct gaagcgtgcg atccagcgct    4440
ggatcgagaa cccgctggcg cagctgattc tggccggcaa gttcctgccc ggtacggcga    4500
tcaccgccaa ggtggaaggc gacgaaatcg tctttggctg attgtgttgc accatgagcc    4560
ccgcgtttgc ggggctatga aaccacaat ttgggagaga tcgacaatga aacttcgtcc    4620
tctgcatgac cgcgtagtca tccgtcgcag cgaagaagaa tcgaaaaccg ctggcggtat    4680
cgtcctgccg ggttcggccg ctgaaaaacc aaaccgcggc gaagttgtag ccgtcggcac    4740
cggtcgcgtc ctggacaacg gcgaagttcg cgcgctggcc gtgaaagtgg gtgacaaagt    4800
ggttttcggc ccgtactcgg gcagcaacac cgtgaaagtc gatggcgaag acctgctggt    4860
catggccgag aacgaaatcc tcgccgttgt cgaaggctga tttccccgac ttcccgttac    4920
tccaaagttt tactccaaag ttttactcca agttttcaa ggattaaacg atcatggctg    4980
ctaaagacgt aaaatttggt gattccgctc gtaagaaaat gctggttggt gtcaacgttc    5040
tggctgacgg ggtaaaagcg accctgggcc cgaaaggccg taacgtggta ctggccaaga    5100
gcttcggcgc gccgaccatc accaaggacg gcgtttccgt cgccaaagaa atcgagctga    5160
aagacgcttt cgaaaacatg gcgcccagc tggtcaagga agttgcttcc aaggccaacg    5220
acgctgccgg tgacggcacc accaccgcta ccgttctggc tcaggccatc gtcaacgaag    5280
gcctgaaagc cgtcgctgcc ggcatgaacc cgatggacct gaagcgcggt atcgacaagg    5340
ccactgctgc cgtcgttgcc gaactgaaga acctgtccaa gccatgcgcc gactccaagg    5400
ccatcgccca ggtaggtacc atctctgcca actccgacaa ctccatcggt gaaatcatcg    5460
ccgaagccat ggaaaaagtc ggtaaagaag gcgtgatcac cgttgaagaa ggctcgggcc    5520
tggaaaacga actgtccgtc gtagaaggca tgcagttcga ccgcggctac ctgtcgccgt    5580
acttcgtcaa caagccggac accatggttg ccgagctgga aggcccgctg ctgctgctgg    5640
tcgacaagaa aatctccaac atccgtgagc tgctgccagt tctggaagcc gttgccaagg    5700
ccggccgccc actgctgatc gttgccgaag acgttgaagg tgaagcgctg gctaccctgg    5760
tagtcaacaa catgcgcggc atcgtcaagg ttgctgcagt caaggctccg ggcttcggcg    5820
atcgccgcaa ggccatgctg caggacatcg ctgtcctgac tggcggccag gtcatctccg    5880
aagaaatcgg cctgtccctg gaaaccgcta ccctggagca cctgggtaac gccaagcgcg    5940
tcatcctgtc caaggaaaac accaccatca tcgacggtgc tggcgctgac accgagatcg    6000
aagcacgcgt caagcagatc cgtgcccaga tcgaagaaac ttcctcggac tacgaccgtg    6060
agaagctgca agagcgtctg gccaagctgg ctggcggtgt tgccgtgatc aaggtcggtg    6120
ccggcaccga agttgaaatg aaagagaaga agcccgcgt tgaagacgcc ctgcacgcta    6180
cccgtgcagc cgttgaagaa ggcgtggtgc ctggcggtgg tgttgccctg gttcgcgccc    6240
tggcagccat catcgacctg aaaggcgaca acgaagacca gaacgtcggt atcgcgctgc    6300
tgcgtcgcgc tgttgaatcc ccgctgcgcc agatcactgc caacgccggt gatgagccaa    6360
gcgtggttgc tgacaaggtc aagcaaggtt cgggcaactt cggctacaac gccgctaccg    6420
gtgaatacgg cgacatgatc gagatgggta tcctggaccc agccaaggtc actcgctcgg    6480
```

```
cgctgcaagc tgctgcttcg atcggcggtc tgatgatcac caccgaagcc atggttgccg     6540
acctgccgga agacaagcca gctgctggca tgcctgatat gggtggcatg ggtggcatgg     6600
gcggcatgat gtaagccagc cttacccccc tgcaccatca aaatagtcaa aagcctccga     6660
ccggaggctt ttgactgttg cgtaaatctt ccccaaaatg catccgtaaa cacctgattc     6720
tattggggtc gaaacgaaca aaaaaggcgc aattccgatg cgccatattt gctttaaggc     6780
attgatttaa ctgggcttta gtcggtttaa cttggcgtcc caggctttga tgccgtagag     6840
cgtgtaggtc attgtgtaca ttggggttgc aagtagcccc aatctctccg ttttcgatg     6900 tcagtcgcgg gattatgcgg gaacgatcct cgcggcgcca cgcccgtggc gccctgttt     6960 attgatcagg atgtgttcaa gcgaccagac gctggaccga cccgatgatc tcatcgccgt     7020
gttgctgttc ggctgtgcgc agatcgaagg ccgtctgcag gttgagccag aactcagggg     7080
tggtgtccag gcagatggac aggcgcagtg ccatgtcggc ggaaacaccg ccccgttcgc     7140
gcaggatgtt gttgacggtt ggcgttgcta cacccaacgc cctggccaga gccgcggcgc     7200
tgaagcccat ttccttctgg aactcctccc gcaggatttc acccggatgg attggacgca     7260
taccgttctt gagcatgatg cacctcagtg gtaatcgaca atttcaacgt taactggccc     7320
gtgctctgtc caggtgaagc acaaccgcca ttggtcattt acacggatac tgtgctggtc     7380
ggcgcggttg ccgctcagtg actcgaggcg attgccaggt ggcgacctaa ggtctcgcaa     7440
ctctgttgcg gcatcgagca tggccagctt gcgctccgcg actgacttga tatctgaccc     7500
gcgccgtgtc tttcccgttg tgaagagcgc ttccgtgtcg gcacagctaa agcttcgaat     7560
catgagctga atgcttaacg ttattcgtta atttcgatta tacgacggga tcgctgtagt     7620
tcaagtcttc aataacgggc acgcgactcg caagctccgg tcacatctgc tgggtatcat     7680
catgttacat attccccgt cacctgcgac tatcgtgcag cggccccgaa ccgccggtcg     7740
ccgctaacat attgttccaa tggcgatgtt tcgccttgct atcgtttctg gttcacaaag     7800
gaagctttcc cggatgcagt ccgcctacac cgttctcatc ctgctgacgc tggtcagcct     7860
gtcgaagctg gtcggccctg caggcatgca agcttggcac tggccgtcgt tttacaacgt     7920
cgtgaccgga attgccagct ggggcgccct ctggtaaggt tgggaagccc tgcaaacagg     7980
atgaggatcg tttcgcatga ttgaacaaga tggattgcac gcaggttctc cggccgcttg     8040
ggtggagagg ctattcggct atgactgggc acaacagaca atcggctgct ctgatgccgc     8100
cgtgttccgg ctgtcagcgc aggggcgccc ggttcttttt gtcaagaccg acctgtccgg     8160
tgccctgaat gaactccaag acgaggcagc gcggctatcg tggctggcca cgacgggcgt     8220
tccttgcgca gctgtgctcg acgttgtcac tgaagcggga agggactggc tgctattggg     8280
cgaagtgccg gggcaggatc tcctgtcatc tcaccttgct cctgccgaga agtatccat     8340 catggctgat gcaatgcggc ggctgcatac gcttgatccg gctacctgcc cattcgacca     8400
ccaagcgaaa catcgcatcg agcgagcacg tactcggatg gaagccggtc ttgtcgatca     8460
ggatgatctg gacgaagagc atcaggggct cgcgccagcc gaactgttcg ccaggctcaa     8520
ggcgcggatg cccgacggcg aggatctcgt cgtgacccat ggcgatgcct gcttgccgaa     8580
tatcatggtg gaaaatggcc gcttttctgg attcatcgac tgtggccggc tgggtgtggc     8640
ggaccgctat caggacatag cgttggctac ccgtgatatt gctgaagagc ttggcggcga     8700
atgggctgac cgcttcctcg tgctttacgg tatcgccgct cccgattcgc agcgcatcgc     8760
cttctatcgc cttcttgacg agttcttctg agcgacgatg aacatcaaaa agtttgcaaa     8820
```

```
acaagcaaca gtattaacct ttactaccgc actgctggca ggaggcgcaa ctcaagcgtt    8880
tgcgaaagaa acgaaccaaa agccatataa ggaaacatac ggcatttccc atattacacg    8940
ccatgatatg ctgcaaatcc ctgaacagca aaaaaatgaa aaatatcaag tttctgaatt    9000
tgattcgtcc acaattaaaa atatctcttc tgcaaaaggc ctggacgttt gggacagctg    9060
gccattacaa aacgctgacg gcactgtcgc aaactatcac ggctaccaca tcgtctttgc    9120
attagccgga gatcctaaaa atgcggatga cacatcgatt tacatgttct atcaaaaagt    9180
cggcgaaact tctattgaca gctggaaaaa cgctggccgc gtcttaaag acagcgacaa     9240 attcgatgca aatgattcta tcctaaaaga ccaaacacaa gaatggtcag gttcagccac    9300
atttacatct gacggaaaaa tccgtttatt ctacactgat ttctccggta aacattacgg    9360
caaacaaaca ctgacaactg cacaagttaa cgtatcagca tcagacagct ctttgaacat    9420
caacggtgta gaggattata aatcaatctt tgacggtgac ggaaaaacgt atcaaaatgt    9480
acagcagttc atcgatgaag gcaactacag ctcaggcgac aaccatacgc tgagagatcc    9540
tcactacgta gaagataaag gccacaaata cttagtattt gaagcaaaca ctggaactga    9600
agatggctac caaggcgaag aatctttatt taacaaagca tactatggca aaagcacatc    9660
attcttccgt caagaaagtc aaaaacttct gcaaagcgat aaaaaacgca cggctgagtt    9720
agcaaacggc gctctcggta tgattgagct aaacgatgat tacacactga aaaagtgat     9780 gaaaccgctg attgcatcta acacagtaac agatgaaatt gaacgcgcga acgtctttaa    9840
aatgaacggc aaatggtacc tgttcactga ctcccgcgga tcaaaaatga cgattgacgg    9900
cattacgtct aacgatattt acatgcttgg ttatgtttct aattctttaa ctggcccata    9960
caagccgctg aacaaaactg gccttgtgtt aaaaatggat cttgatccta acgatgtaac   10020
ctttacttac tcacacttcg ctgtacctca agcgaaagga aacaatgtcg tgattacaag   10080
ctatatgaca aacagaggat tctacgcaga caaacaatca acgtttgcgc cgagcttcct   10140
gctgaacatc aaaggcaaga aaacatctgt tgtcaaagac agcatccttg aacaaggaca   10200
attaacagtt aacaaataat cagaccccgt agaaaagatc aaaggatctt c            10251

<210> SEQ ID NO 8
<211> LENGTH: 248
<212> TYPE: DNA
<213> ORGANISM: Artificial Sequence
<220> FEATURE:
<223> OTHER INFORMATION: synthetic fragment incorporated into PK18sB

<400> SEQUENCE: 8 tcagggggc ggagcctatg gaaaaacgcc tcacacagga aacagctatg acatgattac         60
gaattcgagc tcggtacccg gggatcctct agagtcgacc tgcaggcatg caagcttggc       120
actggccgtc gttttacaac gtcgtgaccg gaattgccag ctggggcgcc ctctggtaag       180
gttgggaagc cctgcaaaca ggatgaggat cgtttcgcat gattgaacaa gatggattgc       240
acgcaggt                                                                248
```